US008273550B2

(12) United States Patent
Cizeau et al.

(10) Patent No.: US 8,273,550 B2

(45) Date of Patent: Sep. 25, 2012

(54) ANTIBODIES AGAINST A CANCER-ASSOCIATED EPITOPE OF VARIANT HNRNPG AND USES THEREOF

(75) Inventors: Jeannick Cizeau, Winnipeg (CA); Francina C. Chahal, Winnipeg (CA)

(73) Assignee: Viventia Biotechnologies Inc., Mississauga, Ontario (CA)

( * ) Notice: Subject to any disclaimer, the term of this patent is extended or adjusted under 35 U.S.C. 154(b) by 161 days.

(21) Appl. No.: 12/738,883

(22) PCT Filed: Oct. 23, 2008

(86) PCT No.: PCT/CA2008/001878

§ 371 (c)(1), (2), (4) Date: Jul. 14, 2010

(87) PCT Pub. No.: WO2009/052628

PCT Pub. Date: Apr. 30, 2009

(65) Prior Publication Data

US 2010/0303814 A1 Dec. 2, 2010

Related U.S. Application Data

(60) Provisional application No. 60/982,575, filed on Oct. 25, 2007.

(51) Int. Cl.
*C12P 21/08* (2006.01)

(52) U.S. Cl. ................. 435/69.1; 530/387.1; 530/387.3; 530/387.9; 530/388.2; 530/388.8; 530/391.3; 530/391.7; 536/23.5; 435/320.1; 435/325

(58) Field of Classification Search ............... 530/387.1, 530/387.3, 387.9, 388.2, 388.8, 391.3, 391.7; 536/23.5; 435/69.1, 320.1, 325
See application file for complete search history.

(56) References Cited

U.S. PATENT DOCUMENTS

2006/0269557 A1 11/2006 Sherman et al.

FOREIGN PATENT DOCUMENTS

| | | |
|---|---|---|
| CA | 2532781 | 1/2005 |
| WO | 2004030615 A2 | 4/2004 |
| WO | 2005014780 A2 | 2/2005 |

OTHER PUBLICATIONS

Martinez-Arribas et al. "Positive Correlation Between the Expression of X-Chromosome RBM Genes (RBMX, RBM3, RBM10) and the Proapoptotic Bax Gene in Human Breast Cancer", J. Cell. Biochem. Apr. 15, 2006, 97 (6):1275-1282.

Soulard et al. "hnRNP G: sequence and characterization of a glycosylated RNA-binding protein" Nucleic Acids Res. Sep. 11, 1993, 21(18):4210-4217.

Soulard et al. "Autoimmune Antibodies to hnRNPG Protein in Dogs with Systemic Lupus Erythematosus: Epitope Mapping of the Antigen", J. Autoimmune, May 2002, 18(3):221-229.

Database Genbank [Online] May 4, 1999, "*Homo sapiens* isolate 1396 immunoglobulin light chain variable region gene, partial cds", retrieved from NCBI accession No. AF116543, Database accession No. AF116543.

Laune et al. "Systemic Exploration of the Antigen Binding Activity of Synthetic Peptides isolated from the Variable Regions of Immunoglobulins", The Journal of Biological Chemistry, vol. 272, No. 49, pp. 30937-30944, 1997.

Qiu et al. "Small Antibody Mimetics Comprising Two Complementary-Determining Regions and a Framework Region for Tumor Targeting", Nature Biotechnology, vol. 25, No. 8, pp. 921-929, Aug. 2007.

Gao, et al. "Molecular Cloning of a Proteolytic Antibody Light Chain", The Journal of Biological Chemistry, vol. 269, No. 51, Dec. 23, 1994, pp. 32389-32393.

Monnet et al. "Synthetic Peptides Derived from the Variable Regions of an Anti-CD4 Monoclonal Antibody Bind to CD4 and Inhibit HIV-1 Promoter Activation in Virus-Infected Cells", The Journal of Biological Chemistry, vol. 274, No. 6, Feb. 5, 1999, pp. 3789-3796.

Quiocho, "Making of the Minibody", Nature Publishing Group, vol. 362, Mar. 25, 1993, pp. 293-294.

Bianchi et al. "High Level Expression and Rational Mutagenesis of a Designed Protein, the Minibody From an Insoluble to a Soluble Molecule", J. Mol. Biol., 1994, vol. 236, pp. 649-659.

Vaughan et al. "Of Minibody, Camel and Bacteriophage", Combinatorial Chemistry & High Throughput Screening, 2001, vol. 4, pp. 417-430.

Ladner, "Antibodies Cut Down to Size", Nature Biotechnology, vol. 25, No. 8, Aug. 2007, pp. 875-877.

Pessi et al. "A Designed Metal-Binding Protein with a Novel Fold", Nature, vol. 362, Mar. 25, 1993, pp. 367-369.

Nicaise et al "Affinity Transfer by CDR Grafting on a Nonimmunoglobulin Scaffold", Protein Science, 2004, vol. 13, pp. 1882-1891.

Heap et al. "Analysis of a 17-Amino Acid Residue, Virus-Neutralizing Microantibody", Journal of General Virology, 2005, vol. 86, pp. 1791-1800.

Ross et al. "Prostate Stem Cell Antigen As Therapy Target: Tissue Expression and in vivo Efficacy of an Immunoconjugate", Cancer Research, American Association for Cancer Research, US, vol. 62, No. 9, p. 2546-2553, 2002.

Elsamman et al. "The expression of prostate stem cell antigen in human clear cell renal cell carcinoma: a quantitative reverse transcriptase-polymerase chain reaction analysis". BJU International, vol. 98, No. 3, p. 668-673, 2006.

Database UniProt [Online] Uniprot; Database accession No. 043653, 1998.

Thomas-Kaskel et al. "Vaccination of advanced prostate cancer patients with PSCA and PSA peptide-loaded dendritic cells induces DTH responses that correlate with superior overall survival", International Journal of Cancer, vol. 119, No. 10, p. 2428-2434, 2006.

Zhang et al. "Vaccination with a DNA vaccine based on human PSCA and HSP70 adjuvant enhances the antigen-specific CD8(+) T-cell response and inhibits the PSCA(+) tumors growth in mice", Journal of Gene Medicine, John Wiley & Sons, Inc., US, vol. 9, No. 8, p. 715-726, 2007.

Shin et al. "Heterogeneous nuclear ribonucleoprotein G shows tumor suppressive effect against oral squamous cell carcinoma cells", Clinical Cancer Research: An Official Journal of the American Association for Cancer Research, vol. 12, No. 10, p. 3222-3228, 2006.

*Primary Examiner* — Stephen Rawlings

(74) *Attorney, Agent, or Firm* — Bereskin & Parr LLP/S.E.N.C.R.L., s.r.l.; Micheline Gravelle

(57) ABSTRACT

The present application provides the amino acid and nucleic acid sequences of heavy and light chain complementarity determining regions of a cancer specific antibody directed to an epitope of variant Heterogeneous Ribonucleoprotein G (HnRNPG). In addition, the application provides cancer specific antibodies and immunoconjugates comprising the cancer specific antibody attached to a toxin or label, and methods of uses thereof. The application also relates to diagnostic methods and kits using the cancer specific antibodies disclosed herein. Further, the application provides novel cancer-associated epitopes and antigens of variant HnRNPG, and uses thereof.

39 Claims, 38 Drawing Sheets

Figure 1:

VB1-213 VH Nucleotide and Amino Acid Sequence

```
GAG GTG CAG CTG TTG GAG TCT GGG GGA GGC TTG GTA CAG CCT GGG GGG TCC CTG AGA
 E   V   Q   L   L   E   S   G   G   G   L   V   Q   P   G   G   S   L   R

CTC TCC TGT GCA GCC TCG GGA TTC ACC TTT AGA AGC TAT GCC ATG AGC TGG GTC CGC
 L   S   C   A   A   S   G   F   T   F   R   S   Y   A   M   S   W   V   R
                                            |--    CDR 1    --|

CAG GCT CCA GGG AAG GGG CTG GAA TGG GTC TCA ACT ATT AGT GGT CGT GGT GTT ACC
 Q   A   P   G   K   G   L   E   W   V   S   T   I   S   G   R   G   V   T
                                            |------------------------ CDR 2

ACA TAC TAC GCA GAC TCC GTG AAG GGC CGG TTC ACC ATC TCC AGA GAC AAT TCC AAG
 T   Y   Y   A   D   S   V   K   G   R   F   T   I   S   R   D   N   S   K
-----------------------------------|

AAC ACA CTG TAT TTG CAA ATG AAC AGC CTG AGA GCC GAC GAC ACG GCC CTA TAT TAC TGT
 N   T   L   Y   L   Q   M   N   S   L   R   A   D   D   T   A   L   Y   Y   C

GCG AAA GAT CGT ACC CGC TAC TAC GGT ATG GAC GTC TGG GGC CAA GGG ACC ACG GTC
 A   K   D   R   T   R   Y   Y   G   M   D   V   W   G   Q   G   T   T   V
        |--         CDR 3         --------|

ACC GTC TCC TCA  (SEQ ID NO:13)
 T   V   S   S   (SEQ ID NO:14)
```

Figure 2:

VB1-213 VL Nucleotide and Amino Acid Sequence

```
TCC TAT GAG CTG ACT CAG CCA CCC TCA GTG TCC GTG TCC CCA GGA CAG ACA GCC AGC
 S   Y   E   L   T   Q   P   P   S   V   S   V   S   P   G   Q   T   A   S

ATC ACC TGC TCT GGA AAT AAA TTG GGG GAT AAA TAT GCT TGC TGG TAT CAG CAG AAG TCA
 I   T   C   S   G   N   K   L   G   D   K   Y   A   C   W   Y   Q   Q   K   S
            |-------------------- CDR 1 ----------------|

GGC CAG TCC CCT GTG CTG GTC ATC TAT CAA GAT TCC AAG CGG CCC TCA GGG ATC CCT
 G   Q   S   P   V   L   V   I   Y   Q   D   S   K   R   P   S   G   I   P
                                    |-------- CDR 2 --------|

GAG CGA TTC TCT GGC TCC AAC TCT GGG AAC ACA GCC ACT CTG ACC ATC AGC GGG ACC
 E   R   F   S   G   S   N   S   G   N   T   A   T   L   T   I   S   G   T

CAG GCT TTG GAT GAG GCT GAC TAT TAC TGT CAG GCG TGG GAC AAC AGC ACT GCG GTA
 Q   A   L   D   E   A   D   Y   Y   C   Q   A   W   D   N   S   T   A   V
                                        |----------- CDR 3 -------------|

TTC GGC GGA GGG ACC AAG CTG ACC GTC CTA GGT   (SEQ ID NO:15)
 F   G   G   G   T   K   L   T   V   L   G    (SEQ ID NO:16)
```

A B

Figure 9-A
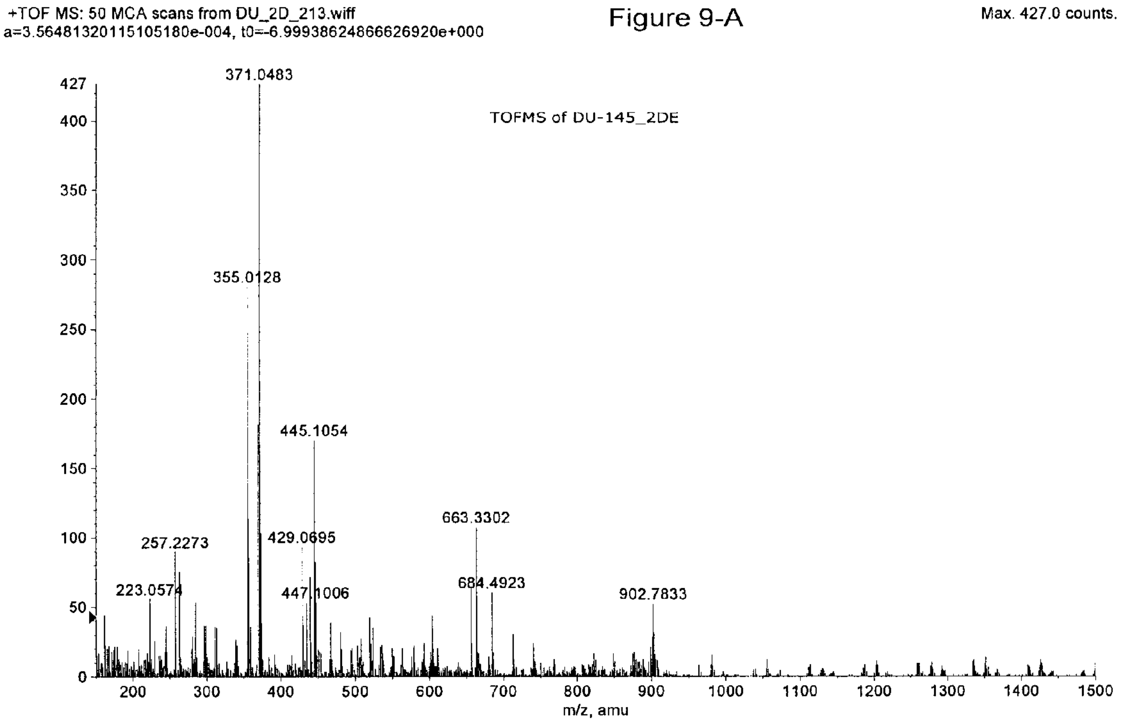
Figure 9-B
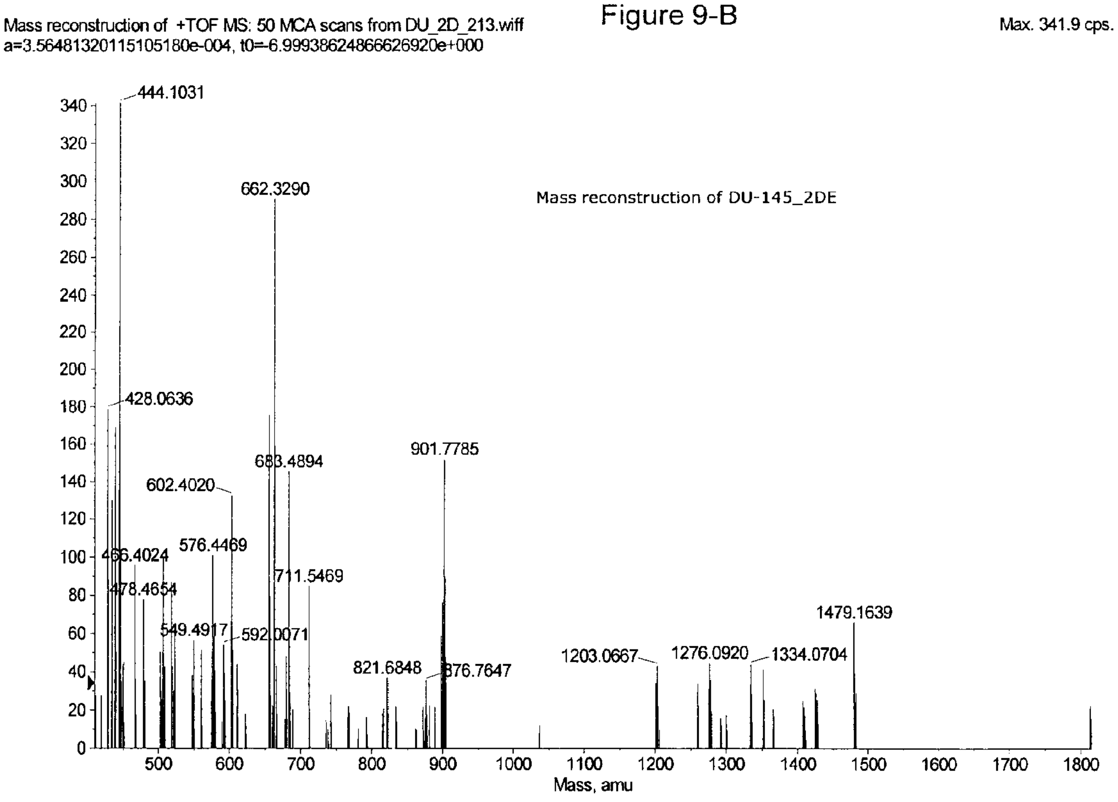

Figure 11:

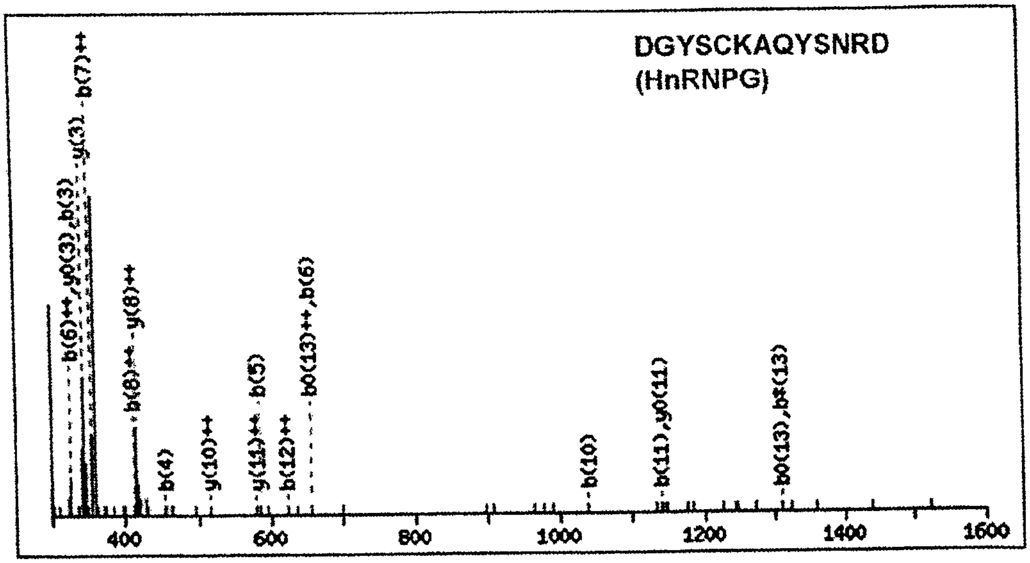

Monoisotopic mass of neutral peptide Mr(calc): 1481.81Ions Score: 48 Expect: 4e+03 Matches (Bold Red): 19/120 fragment ions using 58 most intense peaks

Figure 12:

A: HnRNPG variant (SEQ ID NO: 71)

```
1    MVEADRPGKL FIGGLNTETN EKALEAVFGK YGRIVEVLLM KDRETNKSRG
51   FAFVTFESPA DAKDAARDMN GKSLDGKAIK VEQATKPSFE SGRRGPPPPP
101  RSRGPPRGLR GGRGGSGGTR GPPSRGGHMD DGGYSMNFNM SSSRGPLPVK
151  RGPPPRSGGP PPKRSAPSGP VRSSSGMGGR APVSRGRDSY GGPPRREPLP
201  SRRDVYLSPR DDGYSCKAQY SNRDYPSSRD TRDYAPPPRD YTYRDYGHSS
251  SRDDYPSRGY SDRDGYGRDR DYSDHPSGGS YRDSYESYGN SRSAPPTRGP
301  PPSYGGSSRY DDYSSSRDGY GGSRDSYSSS RSDLYSSGRD RVGRQERGLP
351  PSMERGYLLH VIPTAVQAAD SQEVVAVEEA DLIEGEAEAD TRNKQNFGPK
401  SQFKETKSGN YSIITTQGLL KGKIVLLFLN SLLSSPP
```

B:normal HnRNPG Gi: 3258007 (SEQ ID NO: 113)

```
1    MVEADRPGKL FIGGLNTETN EKALEAVFGK YGRIVEVLLM KDRETNKSRG
51   FAFVTFESPA DAKDAARDMN GKSLDGKAIK VEQATKPSFE SGRRGPPPPP
101  RSRGPPRGLR GGRGGSGGTR GPPSRGGHMD DGGYSMNFNM SSSRGPLPVK
151  RGPPPRSGGP PPKRSAPSGP VRSSSGMGGR APVSRGRDSY GGPPRREPLP
201  SRRDVYLSPR DDGYSTKDSY SSRDYPSSRD TRDYAPPPRD YTYRDYGHSS
251  SRDDYPSRGY SDRDGYGRDR DYSDHPSGGS YRDSYESYGN SRSAPPTRGP
301  PPSYGGSSRY DDYSSSRDGY GGSRDSYSSS RSDLYSSGRD RVGRQERGLP
351  PSMERGYPPP RDSYSSSSRG APRGGGRGGS RSDRGGGRSR Y
```

+TOF MS: Experiment 1, 0.017 to 9.842 min from DataSET1.wiff
a=3.56481320115105180e-004, t0=-6.99938624866626920e+000
Figure 13-A
Max. 262.9 counts.
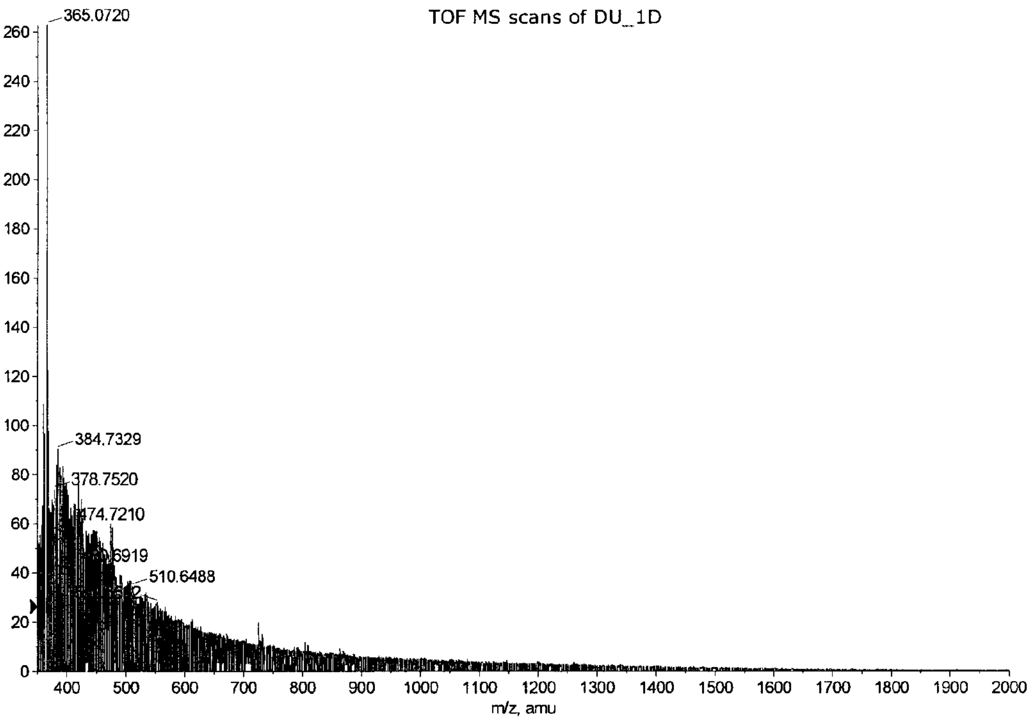
Mass reconstruction of +TOF MS: Experiment 1, 0.017 to 9.842 min from DataSET1.wiff
a=3.56481320115105180e-004, t0=-6.99938624866626920e+000
Figure 13-B
Max. 298.8 cps.
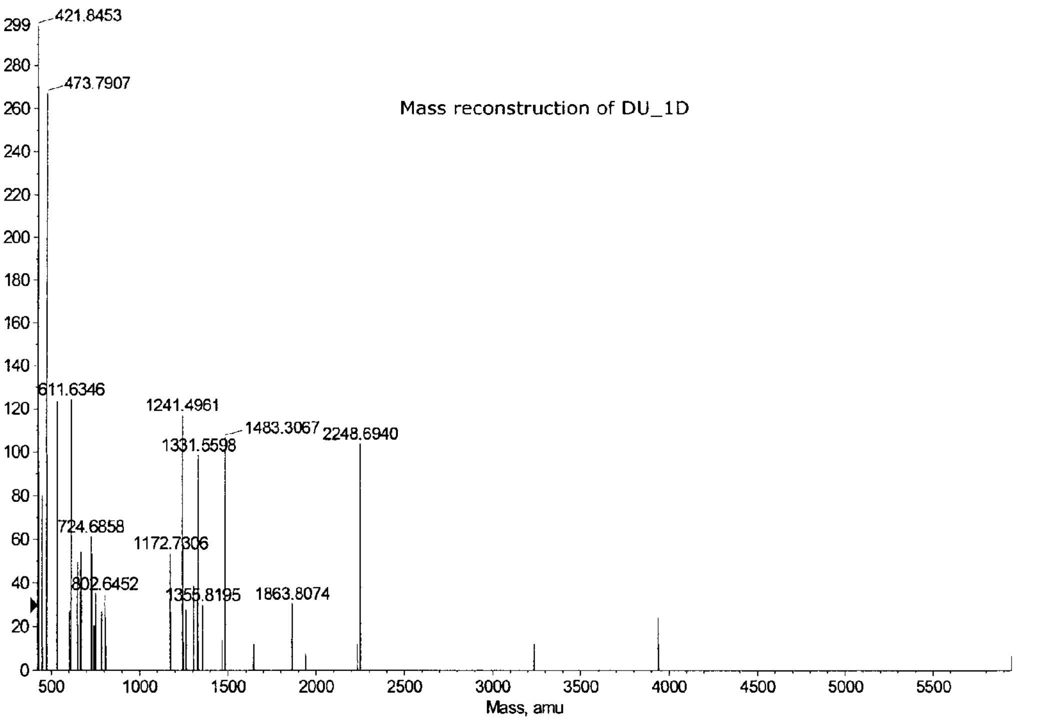

Mass reconstruction of +TOF MS: 300 MCA scans from Sample 4 (tofms) of gel_SKBR-3.wiff
a=3.56481320115105180e-004, t0=-6.99938624866626920e+000
Figure 14-A
Max. 1.8e4 cps.
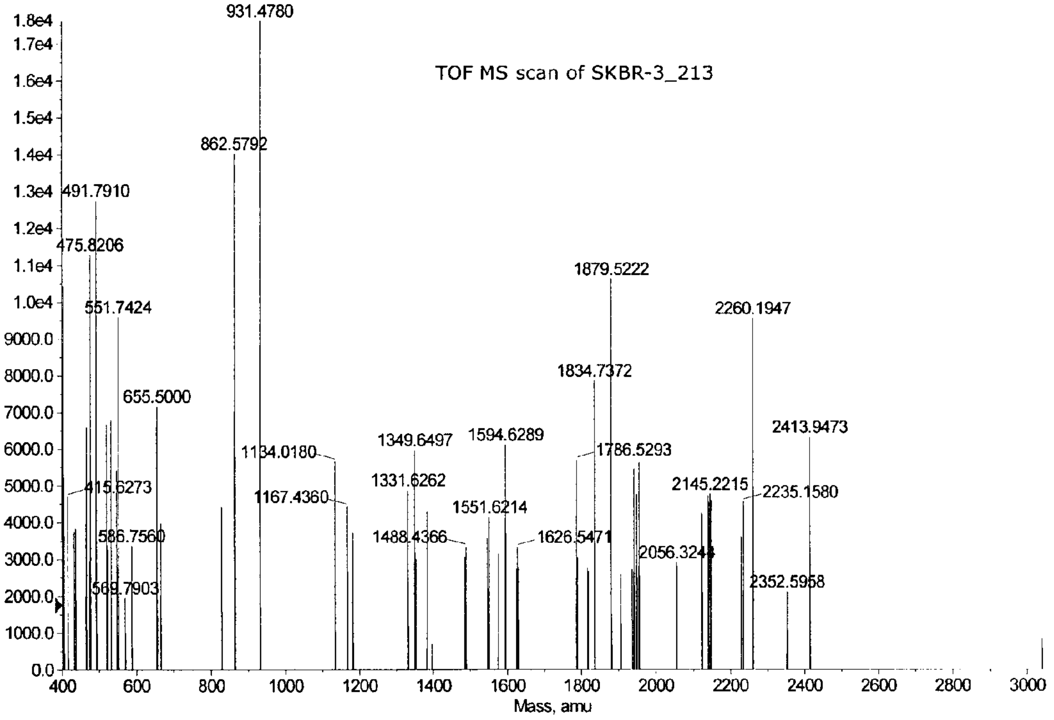
Mass reconstruction of +TOF MS: 300 MCA scans from Sample 4 (tofms) of gel_SKBR-3.wiff
a=3.56481320115105180e-004, t0=-6.99938624866626920e+000
Figure 14-B
Max. 1.8e4 cps.
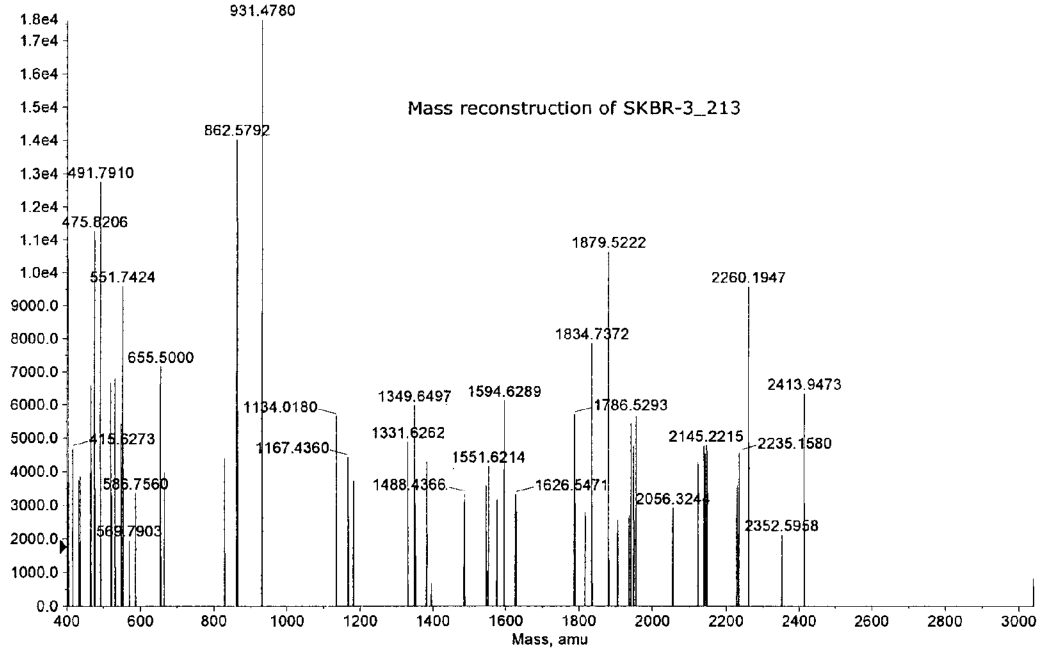

Figure 15-A
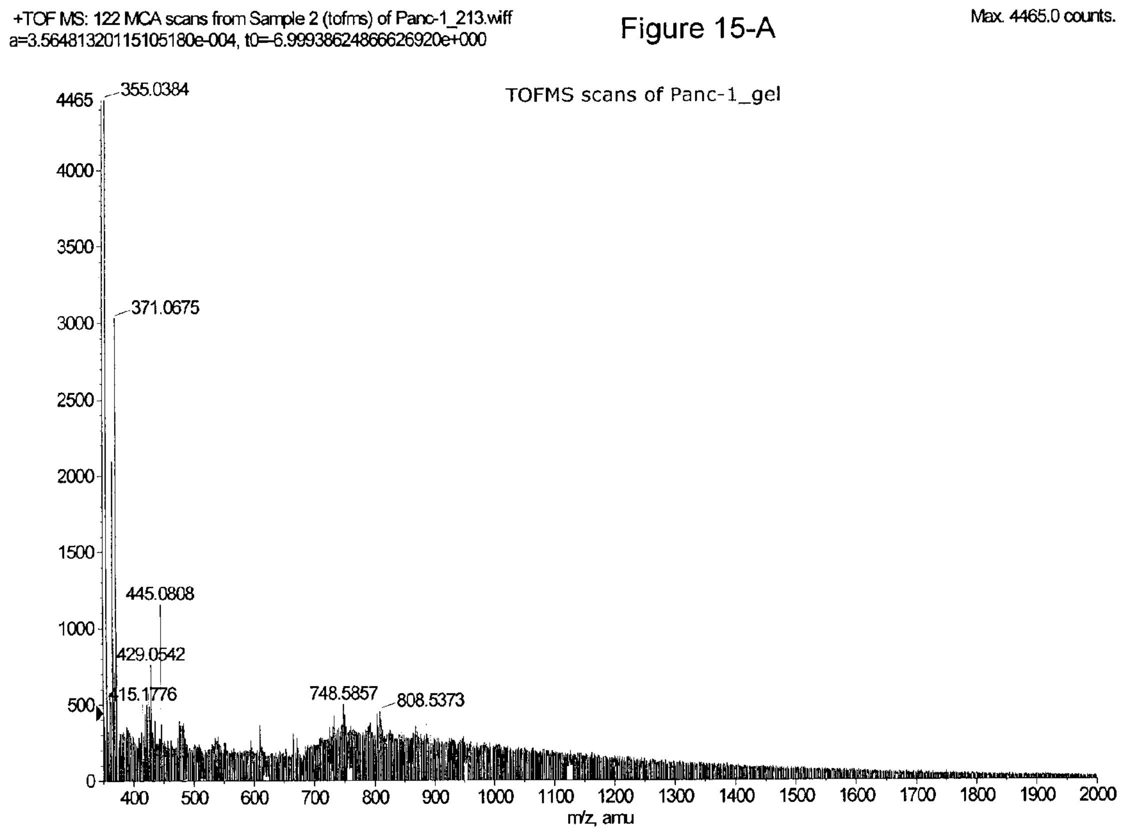
Figure 15-B
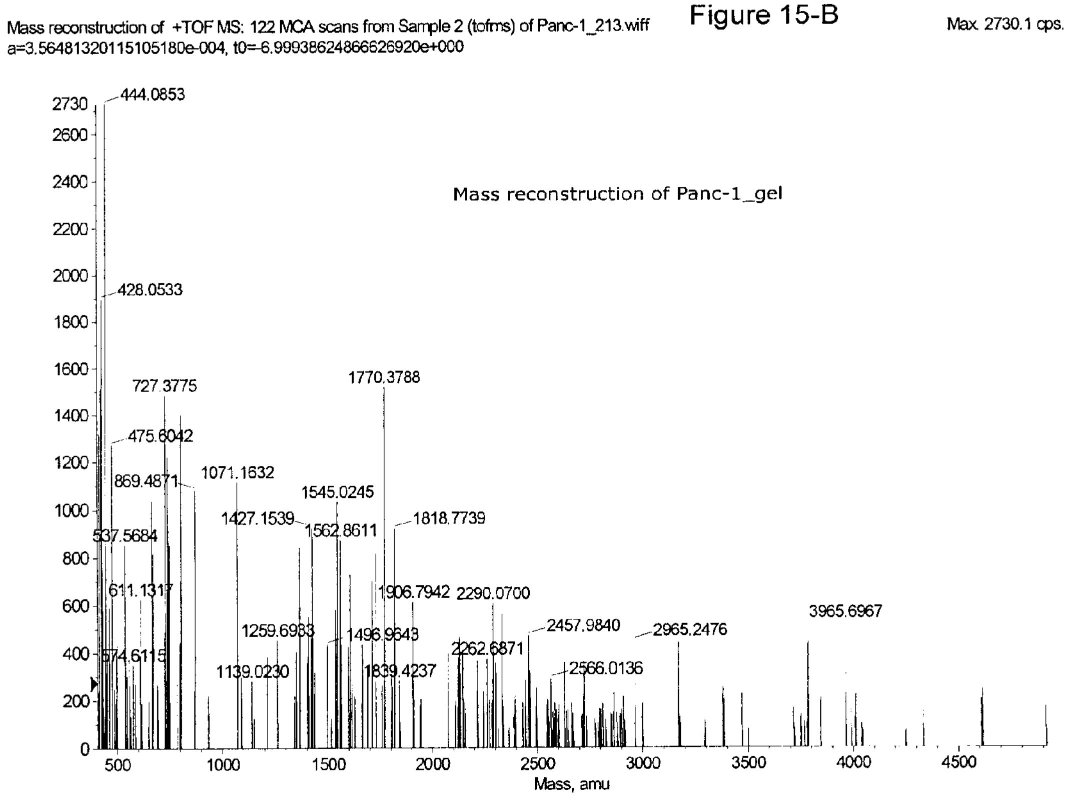

Figure 18

Gi|9367212 Prostate stem cell antigen – 95% coverage (SEQ ID NO 17)

```
1    MKAVLLALLM AGLALQPGTA LLCYSCKAQV SNEDCLQVEN CTQLGEQCWT
51   ARIRAVGLLT VISKGCSLNC VDDSQDYYVG KKNITCCDTD LCNASGAHAL
101  QPAAAILALL PALGLLLWGP GQL
```

Figure 19

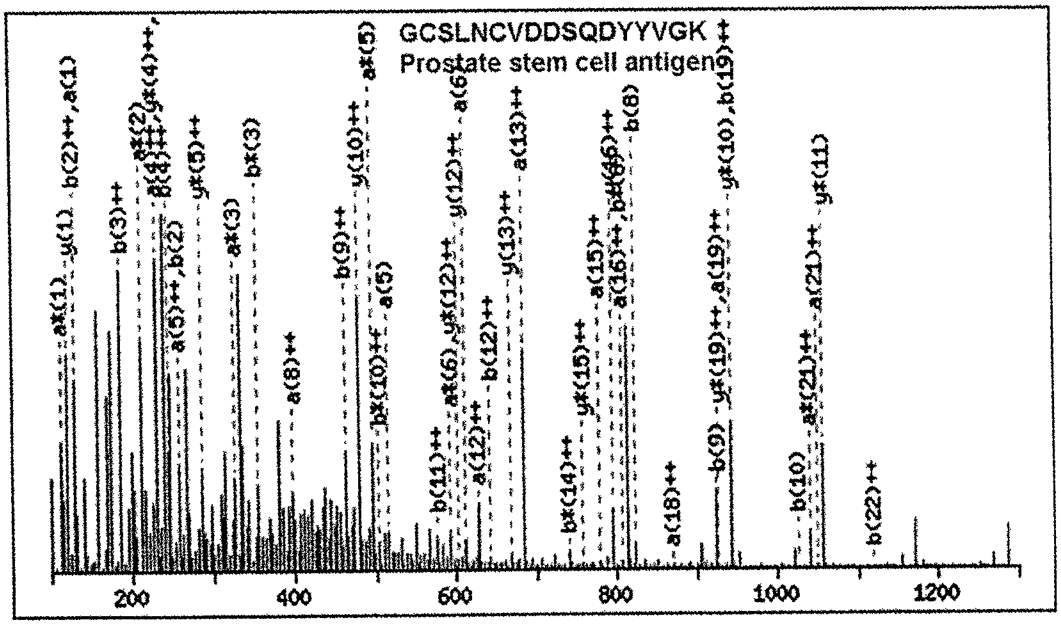

Monoisotopic mass of neutral peptide Mr(calc): 1866.00
Fixed modifications: Carbamidomethyl (C)Ions Score: 81 Expect: 1.9e+03 Matches (Bold Red): 80/222 fragment ions using 120 most intense peaks

Figure 20

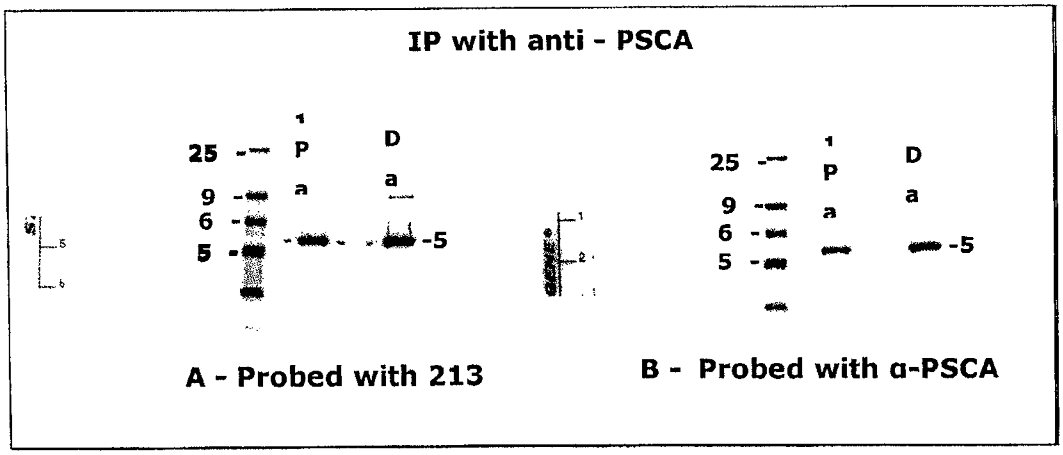

Figure 23
VB6-213-CL-de-bouganin nucleotide sequence (SEQ ID NO:42)

*GAA TTC* CTG CAG GTC TAT GGA ACG ATA AAT GCC CAT GAA AAT TCT ATT TCA AGG AGA
*EcoRI*

CAG TCA TA ATG AAA TAC CTA TTG CCT ACG GCA GCC GCT GGA TTG TTA TTA CTC GCT GCC
|________________ PelB Leader Sequence ________________

CAA CCA GCG ATG GCG CAC CAT CAT CAC CAT CAC GAG GTG CAG CTG TTG GAG TCT GGG
______________| 6xHis |---------- $V_H$ Start
GGA GGC TTG GTA CAG CCT GGG GGG TCC CTG AGA CTC TCC TGT GCA GCC TCG GGA TTC

ACC TTT AGA AGC TAT GCC ATG AGC TGG GTC CGC CAG GCT CCA GGG AAG GGG CTG GAA

TGG GTC TCA ACT ATT AGT GGT CGT GGT GTT ACC ACA TAC TAC GCA GAC TCC GTG AAG GGC

CGG TTC ACC ATC TCC AGA GAC AAT TCC AAG AAC ACA CTG TAT TTG CAA ATG AAC AGC CTG

AGA GCC GAC GAC ACG GCC CTA TAT TAC TGT GCG AAA GAT CGT ACC CGC TAC TAC GGT ATG

GAC GTC TGG GGC CAA GGG ACC ACG GTC ACC GTC TCC TCA GCT TCC ACC AAG GGC CCA
$V_H$ End ------------||---------- $C_H$ Start
TCG GTC TTC CCC CTG GCA CCC TCC TCC AAG AGC ACC TCT GGG GGC ACA GCG GCC CTG

GGC TGC CTG GTC AAG GAC TAC TTC CCC GAA CCG GTG ACG GTG TCG TGG AAC TCA GGC

GCC CTG ACC AGC GGC GTG CAC ACC TTC CCG GCT GTC CTA CAG TCC TCA GGA CTC TAC

TCC CTC AGC AGC GTG GTG ACC GTG CCC TCC AGC AGC TTG GGC ACC CAG ACC TAC ATC

TGC AAC GTG AAT CAC AAG CCC AGC AAC ACC AAG GTG GAC AAG AAA GTT GAG CCC AAA TCT

TGT TAG TGA TCT AGA GTC GAC CTG CAG GTC TAT GGA ACG ATA AAT GCC CAT GAA AAT TCT
$C_H$ end -------|

ATT TCA AGG AGA CAG TCA TA ATG AAA TAC CTA TTG CCT ACG GCA GCC GCT GGA TTG TTA
|________________ PelB Leader Sequence ______

TTA CTC GCT GCC CAA CCA GCG ATG GCG TCC TAT GAG CTG ACT CAG CCA CCC TCA GTG
________________________||---------- $V_L$ Start
TCC GTG TCC CCA GGA CAG ACA GCC AGC ATC ACC TGC TCT GGA AAT AAA TTG GGG GAT AAA

TAT GCT TGC TGG TAT CAG CAG AAG TCA GGC CAG TCC CCT GTG CTG GTC ATC TAT CAA GAT

TCC AAG CGG CCC TCA GGG ATC CCT GAG CGA TTC TCT GGC TCC AAC TCT GGG AAC ACA

GCC ACT CTG ACC ATC AGC GGG ACC CAG GCT TTG GAT GAG GCT GAC TAT TAC TGT CAG

GCG TGG GAC AAC AGC ACT GCG GTA TTC GGC GGA GGG ACC AAG CTG ACC GTC CTA GGT
$V_L$ end -------|
CAG CCC AAG GCT GCC CCC TCG GTC ACT CTG TTC CCG CCC TCC TCT GAG GAG CTC CAA

Figure 23 (cont'd)

|---------- $C_L$ Start
GCC AAC AAG GCC ACA CTA GTG TGT CTG ATC AGT GAC TTC TAC CCG GGA GCT GTG ACA

GTG GCC TGG AAG GCA GAT AGC AGC CCC GTC AAG GCG GGA GTG GAG ACC ACC ACA CCC

TCC AAA CAG AGC AAC AAC AAG TAC GCG GCC AGC AGC TAC CTG AGC CTG ACG CCC GAG

CAG TGG AAG TCC CAC AGA AGC TAC AGC TGC CAG GTC ACG CAT GAA GGG AGC ACC GTG

GAG AAG ACA GTG GCC CCT ACA GAA TGT TCA ACC AGG CAC AGG CAG CCC AGA GGC TGG
$C_L$ End -------| |------------------------------- Furin linker ---------------
GAG CAG CTC TAC AAC ACC GTG TCA TTT AAC CTT GGA GAA GCT TAT GAG TAC CCC ACT TTT
------------------| |------- de-bouganin Start
ATA CAA GAT TTG CGC AAT GAA TTG GCT AAG GGC ACA CCA GTA TGT CAA CTT CCA GTG ACA

CTA CAA ACC ATA GCC GAT GAC AAG CGA TTT GTT CTA GTT GAT ATC ACT ACG ACC TCG AAG

AAA ACA GTT AAG GTT GCT ATA GAT GTG ACA GAT GTG TAT GTT GTG GGT TAT CAA GAC AAA

TGG GAT GGC AAA GAT CGA GCT GTT TTC CTT GAC AAG GTT CCT ACT GTT GCA ACT AGT AAA

CTT TTC CCA GGG GTG ACT AAT CGT GTA ACG TTA ACA TTT GAT GGC AGC TAT CAG AAA CTT

GTG AAT GCT GCC AAA GCT GAT AGA AAG GCT CTC GAA CTG GGG GTT AAC AAA TTG GAA TTT

TCC ATT GAA GCA ATC CAT GGT AAA ACG ATA AAT GGT CAA GAG GCA GCC AAG TTC TTT CTT

ATT GTC ATC CAA ATG GTT TCA GAG GCA GCT CGG TTC AAA TAT ATT GAG ACT GAG GTG GTT

GAT AGA GGA TTA TAT GGA TCA TTC AAA CCT AAT TTT AAA GTA TTG AAC TTG GAG AAC AAT

TGG GGC GAC ATC TCT GAT GCC ATT CAC AAA TCA TCC CCA CAA TGT ACC ACT ATT AAT CCG

GCA CTT CAG TTG ATA AGC CCC TCA AAT GAC CCA TGG GTT GTA AAT AAA GTG AGT CAA ATT

AGT CCC GAT ATG GGT ATC CTT AAG TTT AAA AGC TCC AAA TAG TGA *CTC GAG*
de-bouganin End -------| *XhoI*

Figure 24
VB6-213-Fab-PE nucleotide sequence (SEQ ID NO:43)

*GAA TTC* CTG CAG GTC TAT GGA ACG ATA AAT GCC CAT GAA AAT TCT ATT TCA AGG
*EcoRI*

AGA CAG TCA TA ATG AAA TAC CTA TTG CCT ACG GCA GCC GCT GGA TTG TTA TTA
|________ PelB Leader Sequence ________

CTC GCT GCC CAA CCA GCG ATG GCG GAG GTG CAG CTG TTG GAG TCT GGG GGA
________| |----------- $V_H$ Start

GGC TTG GTA CAG CCT GGG GGG TCC CTG AGA CTC TCC TGT GCA GCC TCG GGA TTC

ACC TTT AGA AGC TAT GCC ATG AGC TGG GTC CGC CAG GCT CCA GGG AAG GGG CTG

GAA TGG GTC TCA ACT ATT AGT GGT CGT GGT GTT ACC ACA TAC TAC GCA GAC TCC

GTG AAG GGC CGG TTC ACC ATC TCC AGA GAC AAT TCC AAG AAC ACA CTG TAT TTG

CAA ATG AAC AGC CTG AGA GCC GAC GAC ACG GCC CTA TAT TAC TGT GCG AAA GAT

CGT ACC CGC TAC TAC GGT ATG GAC GTC TGG GGC CAA GGG ACC ACG GTC ACC GTC

TCC TCA GCT TCC ACC AAG GGC CCA TCG GTC TTC CCC CTG GCA CCC TCC TCC AAG
$V_H$ End --||----------- $C_H$ Start

AGC ACC TCT GGG GGC ACA GCG GCC CTG GGC TGC CTG GTC AAG GAC TAC TTC

CCC GAA CCG GTG ACG GTG TCG TGG AAC TCA GGC GCC CTG ACC AGC GGC GTG

CAC ACC TTC CCG GCT GTC CTA CAG TCC TCA GGA CTC TAC TCC CTC AGC AGC GTG

GTG ACC GTG CCC TCC AGC AGC TTG GGC ACC CAG ACC TAC ATC TGC AAC GTG AAT

CAC AAG CCC AGC AAC ACC AAG GTG GAC AAG AAA GTT GAG CCC AAA TCT TGT GAA
$C_H$ end -------||------

TTT GGT GGC GCG CCG GAG TTC CCG AAA CCG TCC ACC CCG CCG GGT TCT TCT GGT
-------------------- Linker 2 --------------------

CTT GAG GGC GGC AGC CTG GCC GCG CTG ACC GCG CAC CAG GCC TGC CAC CTG
-----||----------- ETA $_{252\text{-}608}$

CCG CTG GAG ACT TTC ACC CGT CAT CGC CAG CCG CGC GGC TGG GAA CAA CTG

GAG CAG TGC GGC TAT CCG GTG CAG CGG CTG GTC GCC CTC TAC CTG GCG GCG

CGA CTG TCA TGG AAC CAG GTC GAC CAG GTG ATC CGC AAC GCC CTG GCC AGC

CCC GGC AGC GGC GGC GAC CTG GGC GAA GCG ATC CGC GAG CAG CCG GAG CAG

Figure 24 (cont'd)

GCA CGT CTC GCT CTG ACC CTG GCC GCC GCC GAG AGC GAG CGC TTC GTC CGG

CAG GGC ACC GGC AAC GAC GAG GCA GGC GCT GCA AGC GCC GAC GTG GTG AGC

CTG ACC TGC CCG GTC GCC GCC GGT GAA TGC GCG GGC CCG GCG GAC AGC GGC

GAC GCC CTG CTG GAG CGC AAC TAT CCC ACT GGC GCG GAG TTC CTC GGC GAC

GGT GGC GAC GTC AGC TTC AGC ACC CGC GGC ACG CAG AAC TGG ACG GTG GAG

CGG CTG CTC CAG GCG CAC CGC CAA CTG GAG GAG CGC GGC TAT GTG TTC GTC

GGC TAC CAC GGC ACC TTC CTC GAA GCG GCG CAA AGC ATC GTC TTC GGC GGG

GTG CGC GCG CGC AGC CAG GAT CTC GAC GCG ATC TGG CGC GGT TTC TAT ATC

GCC GGC GAT CCG GCG CTG GCC TAC GGC TAC GCC CAG GAC CAG GAA CCC GAC

GCG CGC GGC CGG ATC CGC AAC GGT GCC CTG CTG CGG GTC TAT GTG CCG CGC

TCC AGC CTG CCG GGC TTC TAC CGC ACC GGC CTG ACC CTG GCC GCG CCG GAG

GCG GCG GGC GAG GTC GAA CGG CTG ATC GGC CAT CCG CTG CCG CTG CGC CTG

GAC GCC ATC ACC GGC CCC GAG GAG GAA GGC GGG CGC CTG GAG ACC ATT CTC

GGC TGG CCG CTG GCC GAG CGC ACC GTG GTG ATT CCC TCG GCG ATC CCC ACC

GAC CCG CGC AAC GTC GGT GGC GAC CTC GAC CCG TCC AGC ATC CCC GAC AAG

GAA CAG GCG ATC AGC GCC CTG CCG GAC TAC GCC AGC CAG CCC GGC AAA CCG

CCG CAT CAC CAC CAT CAC CAT AAA GAC GAA CTG TAG TGA CTC GAC CTG CAG GTC
|-------------- 6xHis --------------| end of ETA -------|

TAT GGA ACG ATA AAT GCC CAT GAA AAT TCT ATT TCA AGG AGA CAG TCA TA ATG AAA
|______

TAC CTA TTG CCT ACG GCA GCC GCT GGA TTG TTA TTA CTC GCT GCC CAA CCA
________________________PelB Leader Sequence _______ ___________________________

GCG ATG GCG CAT CAC CAT CAC CAT CAC TCC TAT GAG CTG ACT CAG CCA CCC TCA
____________| |------------- 6xHis -------------| |----------- $V_L$ Start

GTG TCC GTG TCC CCA GGA CAG ACA GCC AGC ATC ACC TGC TCT GGA AAT AAA TTG

GGG GAT AAA TAT GCT TGC TGG TAT CAG CAG AAG TCA GGC CAG TCC CCT GTG CTG

GTC ATC TAT CAA GAT TCC AAG CGG CCC TCA GGG ATC CCT GAG CGA TTC TCT GGC

TCC AAC TCT GGG AAC ACA GCC ACT CTG ACC ATC AGC GGG ACC CAG GCT TTG GAT

GAG GCT GAC TAT TAT TGT CAG GCG TGG GAC AAC AGC ACT GCG GTA TTC GGC GGA

Figure 24 (cont'd)

GGG ACC AGG CTG ACC GTC CTA GGT CAG CCC AAG GCT GCC CCC TCG GTC ACT CTG
$V_L$ End ----| |---------- $C_L$ Start

TTC CCG CCC TCC TCT GAG GAG CTC CAA GCC AAC AAG GCC ACA CTA GTG TGT CTG

ATC AGT GAC TTC TAC CCG GGA GCT GTG ACA GTG GCC TGG AAG GCA GAT AGC AGC

CCC GTC AAG GCG GGA GTG GAG ACC ACC ACA CCC TCC AAA CAG AGC AAC AAC AAG

TAC GCG GCC AGC AGC TAC CTG AGC CTG ACG CCC GAG CAG TGG AAG TCC CAC

AGA AGC TAC AGC TGC CAG GTC ACG CAT GAA GGG AGC ACC GTG GAG AAG ACA GTG

GCC CCT ACA GAA TGT TCA TAG TGA *CTC GAG*
$C_L$ End -------| *XhoI*

Figure 25:

Amino acid sequence of $V_{H213}$-$C_H$ (SEQ ID NO:44)

HHHHHHEVQLLESGGGLVQPGGSLRLSCAASGFTFRSYAMSWVRQAPGKGLEWVSTISGRG VTTYYAD
6xHis |------------ $V_H$ Start
SVKGRFTISRDNSKNTLYLQMNSLRADDTALYYCAKDRTRYYGMDVWGQGTTVTVSSASTKG PSVFPLA
$V_L$ end --------||-----------
$C_H$ Start
PSSKSTSGGTAALGCLVKDYFPEPVTVSWNSGALTSGVHTFPAVLQSSGLYSLSSVVTVPSSS LGTQTYICNVNHKPSNTKVDKKVEPKSC
$C_H$ end -------|

Figure 26

Amino acid sequence of $V_{L213}$-$C_L$-de-bouganin (SEQ ID NO:45)

SYELTQPPSVSVSPGQTASITCSGNKLGDKYACWYQQKSGQSPVLVIYQDSKRPSGIPERFSG SNSGNTA

|----------- $V_L$ Start

TLTISGTQALDEADYYCQAWDNSTAVFGGGTKLTVLGQPKAAPSVTLFPPSSEELQANKATLV CLISDFY

$V_L$ end --------||---------- $C_L$ Start

PGAVTVAWKADSSPVKAGVETTTPSKQSNNKYAASSYLSLTPEQWKSHRSYSCQVTHEGSTV EKTVAP

$C_L$ End ---

TECSTRHRQPRGWEQLYNTVSFNLGEAYEYPTFIQDLRNELAKGTPVCQLPVTLQTIADDKRF VLVDITTT

--------||---- Furin linker ----||-------- de-bouganin Start

SKKTVKVAIDVTDVYVVGYQDKWDGKDRAVFLDKVPTVATSKLFPGVTNRVTLTFDGSYQKLV NAAKADRKALELGVNKLEFSIEAIHGKTINGQEAAKFFLIVIQMVSEAARFKYIETEVVDRGLYG SFKPNFKVLNLENNWGDISDAIHKSSPQCTTINPALQLISPSNDPWVVNKVSQISPDMGILKFKS SK de-bouganin End -------|

Figure 27

Amino acid sequence of $V_{H213}$-$C_H$-PE (SEQ ID NO: 46)

EVQLLESGGGLVQPGGSLRLSCAASGFTFRSYAMSWVRQAPGKGLEWVSTISGRGVTTYYAD
|--------- $V_H$ Start
SVKGRFTISRDNSKNTLYLQMNSLRADDTALYYCAKDRTRYYGMDVWGQGTTVTVSSASTKG
$V_H$ End -||-$C_H$Start
PSVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCEFGGAPEFPKPSTPPGSSGLEGGSLAAL
$C_H$ end -------||---------- Linker 2 ------------||-- ETA $_{252-608}$
TAHQACHLPLETFTRHRQPRGWEQLEQCGYPVQRLVALYLAARLSWNQVDQVIRNALASPGS
GGDLGEAIREQPEQARLALTLAAAESERFVRQGTGNDEAGAASADVVSLTCPVAAGECAGPA
DSGDALLERNYPTGAEFLGDGGDVSFSTRGTQNWTVERLLQAHRQLEERGYVFVGYHGTFLE
AAQSIVFGGVRARSQDLDAIWRGFYIAGDPALAYGYAQDQEPDARGRIRNGALLRVYVPRSSL
PGFYRTGLTLAAPEAAGEVERLIGHPLPLRLDAITGPEEEGGRLETILGWPLAERTVVIPSAIPTD
PRNVGGDLDPSSIPDKEQAISALPDYASQPGKPPHHHHHHKDEL
end of ETA ------|

Figure 28:

Amino acid sequence of $V_{L213}$-$C_L$ (SEQ ID NO:47)

HHHHHHSYELTQPPSVSVSPGQTASITCSGNKLGDKYACWYQQKSGQSPVLVIYQDSKRPSGI
|------- $V_L$ Start
PERFSGSNSGNTATLTISGTQALDEADYYCQAWDNSTAVFGGGTKLTVLGQPKAAPSVTLFPP
$V_L$ End ----||------ $C_L$ Start
SSEELQANKATLVCLISDFYPGAVTVAWKADSSPVKAGVETTTPSKQSNNKYAASSYLSLTPE
QWKSHRSYSCQVTHEGSTVEKTVAPTECS
$C_L$ End -------|

Figure 29:
Complete VB6-213-$C_L$-de-bouganin construct

<u>*GAA TTC*</u> CTG CAG GTC TAT GGA ACG ATA AAT GCC CAT GAA AAT TCT ATT TCA AGG AGA
*EcoRI*

CAG TCA TA ATG AAA TAC CTA TTG CCT ACG GCA GCC GCT GGA TTG TTA TTA CTC GCT GCC
M K Y L L P T A A A G L L L L A A
|_____ PelB Leader Sequence _____

CAA CCA GCG ATG GCG CAC CAT CAT CAC CAT CAC GAG GTG CAG CTG TTG GAG TCT GGG
Q P A M A H H H H H H E V Q L L E S G
_____| 6xHis |----------- $V_H$ Start GGA GGC TTG GTA CAG CCT GGG GGG TCC CTG AGA CTC TCC TGT GCA GCC TCG GGA TTC
G G L V Q P G G S L R L S C A A S G F ACC TTT AGA AGC TAT GCC ATG AGC TGG GTC CGC CAG GCT CCA GGG AAG GGG CTG GAA
T F R S Y A M S W V R Q A P G K G L E
CDR 1

TGG GTC TCA ACT ATT AGT GGT CGT GGT GTT ACC ACA TAC TAC GCA GAC TCC GTG AAG GGC
W V S T I S G R G V T T Y Y A D S V K G
CDR 2

CGG TTC ACC ATC TCC AGA GAC AAT TCC AAG AAC ACA CTG TAT TTG CAA ATG AAC AGC CTG
R F T I S R D N S K N T L Y L Q M N S L

AGA GCC GAC GAC ACG GCC CTA TAT TAC TGT GCG AAA GAT CGT ACC CGC TAC TAC GGT ATG
R A D D T A L Y Y C A K D R T R Y Y G M
CDR3

GAC GTC TGG GGC CAA GGG ACC ACG GTC ACC GTC TCC TCA GCT TCC ACC AAG GGC CCA
D V W G Q G T T V T V S S A S T K G P
$V_H$ End -------------||----------- $C_H$ Start TCG GTC TTC CCC CTG GCA CCC TCC TCC AAG AGC ACC TCT GGG GGC ACA GCG GCC CTG
S V F P L A P S S K S T S G G T A A L GGC TGC CTG GTC AAG GAC TAC TTC CCC GAA CCG GTG ACG GTG TCG TGG AAC TCA GGC
G C L V K D Y F P E P V T V S W N S G GCC CTG ACC AGC GGC GTG CAC ACC TTC CCG GCT GTC CTA CAG TCC TCA GGA CTC TAC
A L T S G V H T F P A V L Q S S G L Y TCC CTC AGC AGC GTG GTG ACC GTG CCC TCC AGC AGC TTG GGC ACC CAG ACC TAC ATC
S L S S V V T V P S S S L G T Q T Y I TGC AAC GTG AAT CAC AAG CCC AGC AAC ACC AAG GTG GAC AAG AAA GTT GAG CCC AAA TCT
C N V N H K P S N T K V D K K V E P K S TGT TAG TGA TCT AGA GTC GAC CTG CAG GTC TAT GGA ACG ATA AAT GCC CAT GAA AAT TCT
C

Figure 29 (cont'd)

$C_H$ end -------|

ATT TCA AGG AGA CAG TCA TA ATG AAA TAC CTA TTG CCT ACG GCA GCC GCT GGA TTG TTA
M K Y L L P T A A A G L L
|_____ PelB Leader Sequence _____

TTA CTC GCT GCC CAA CCA GCG ATG GCG TCC TAT GAG CTG ACT CAG CCA CCC TCA GTG
L L A A Q P A M A S Y E L T Q P P S V
_____| |---------- $V_L$ Start TCC GTG TCC CCA GGA CAG ACA GCC AGC ATC ACC TGC TCT GGA AAT AAA TTG GGG GAT AAA
S V S P G Q T A S I T C S G N K L G D K
|—— CDR 1 ——

TAT GCT TGC TGG TAT CAG CAG AAG TCA GGC CAG TCC CCT GTG CTG GTC ATC TAT CAA GAT
Y A C W Y Q Q K S G Q S P V L V I Y Q D
——| |——

TCC AAG CGG CCC TCA GGG ATC CCT GAG CGA TTC TCT GGC TCC AAC TCT GGG AAC ACA
S K R P S G I P E R F S G S N S G N T
CDR 2 ——|

GCC ACT CTG ACC ATC AGC GGG ACC CAG GCT TTG GAT GAG GCT GAC TAT TAC TGT CAG
A T L T I S G T Q A L D E A D Y Y C Q
|——

GCG TGG GAC AAC AGC ACT GCG GTA TTC GGC GGA GGG ACC AAG CTG ACC GTC CTA GGT
A W D N S T A V F G G G T K L T V L G
—— CDR 3 ——| $V_L$ End ----|

CAG CCC AAG GCT GCC CCC TCG GTC ACT CTG TTC CCG CCC TCC TCT GAG GAG CTC CAA
Q P K A A P S V T L F P P S S E E L Q
|---------- $C_L$ Start GCC AAC AAG GCC ACA CTA GTG TGT CTG ATC AGT GAC TTC TAC CCG GGA GCT GTG ACA
A N K A T L V C L I S D F Y P G A V T GTG GCC TGG AAG GCA GAT AGC AGC CCC GTC AAG GCG GGA GTG GAG ACC ACC ACA CCC
V A W K A D S S P V K A G V E T T T P TCC AAA CAG AGC AAC AAC AAG TAC GCG GCC AGC AGC TAC CTG AGC CTG ACG CCC GAG
S K Q S N N K Y A A S S Y L S L T P E CAG TGG AAG TCC CAC AGA AGC TAC AGC TGC CAG GTC ACG CAT GAA GGG AGC ACC GTG
Q W K S H R S Y S C Q V T H E G S T V GAG AAG ACA GTG GCC CCT ACA GAA TGT TCA ACC AGG CAC AGG CAG CCC AGA GGC TGG
E K T V A P T E C S T R H R Q P R G W
$C_L$ End -------| |------------------------------ Furin linker ---------------

GAG CAG CTC TAC AAC ACC GTG TCA TTT AAC CTT GGA GAA GCT TAT GAG TAC CCC ACT TTT
E Q L Y N T V S F N L G E A Y E Y P T F
-------------------| |------- de-bouganin Start

Figure 29 (cont'd)

ATA CAA GAT TTG CGC AAT GAA TTG GCT AAG GGC ACA CCA GTA TGT CAA CTT CCA GTG ACA
I Q D L R N E L A K G T P V C Q L P V T

CTA CAA ACC ATA GCC GAT GAC AAG CGA TTT GTT CTA GTT GAT ATC ACT ACG ACC TCG AAG
L Q T I A D D K R F V L V D I T T T S K

AAA ACA GTT AAG GTT GCT ATA GAT GTG ACA GAT GTG TAT GTT GTG GGT TAT CAA GAC AAA
K T V K V A I D V T D V Y V V G Y Q D K

TGG GAT GGC AAA GAT CGA GCT GTT TTC CTT GAC AAG GTT CCT ACT GTT GCA ACT AGT AAA
W D G K D R A V F L D K V P T V A T S K

CTT TTC CCA GGG GTG ACT AAT CGT GTA ACG TTA ACA TTT GAT GGC AGC TAT CAG AAA CTT
L F P G V T N R V T L T F D G S Y Q K L

GTG AAT GCT GCC AAA GCT GAT AGA AAG GCT CTC GAA CTG GGG GTT AAC AAA TTG GAA TTT
V N A A K A D R K A L E L G V N K L E F

TCC ATT GAA GCA ATC CAT GGT AAA ACG ATA AAT GGT CAA GAG GCA GCC AAG TTC TTT CTT
S I E A I H G K T I N G Q E A A K F F L

ATT GTC ATC CAA ATG GTT TCA GAG GCA GCT CGG TTC AAA TAT ATT GAG ACT GAG GTG GTT
I V I Q M V S E A A R F K Y I E T E V V

GAT AGA GGA TTA TAT GGA TCA TTC AAA CCT AAT TTT AAA GTA TTG AAC TTG GAG AAC AAT
D R G L Y G S F K P N F K V L N L E N N

TGG GGC GAC ATC TCT GAT GCC ATT CAC AAA TCA TCC CCA CAA TGT ACC ACT ATT AAT CCG
W G D I S D A I H K S S P Q C T T I N P

GCA CTT CAG TTG ATA AGC CCC TCA AAT GAC CCA TGG GTT GTA AAT AAA GTG AGT CAA ATT
A L Q L I S P S N D P W V V N K V S Q I

AGT CCC GAT ATG GGT ATC CTT AAG TTT AAA AGC TCC AAA TAG TGA *CTC GAG* (SEQ ID NO:48)
S P D M G I L K F K S S K *XhoI* (SEQ ID NO:49)
de-bouganin End -------|

Figure 30:

Complete VB6-213-Fab-PE construct

*GAA TTC* CTG CAG GTC TAT GGA ACG ATA AAT GCC CAT GAA AAT TCT ATT TCA AGG
*EcoRI*

AGA CAG TCA TA ATG AAA TAC CTA TTG CCT ACG GCA GCC GCT GGA TTG TTA TTA
M K Y L L P T A A A G L L L
|______ PelB Leader Sequence ______

CTC GCT GCC CAA CCA GCG ATG GCG GAG GTG CAG CTG TTG GAG TCT GGG GGA
L A A Q P A M A E V Q L L E S G G
______|| ---------- $V_H$ Start GGC TTG GTA CAG CCT GGG GGG TCC CTG AGA CTC TCC TGT GCA GCC TCG GGA TTC
G L V Q P G G S L R L S C A A S G F ACC TTT AGA AGC TAT GCC ATG AGC TGG GTC CGC CAG GCT CCA GGG AAG GGG CTG
T F R S Y A M S W V R Q A P G K G L
|—— CDR 1 ——|

GAA TGG GTC TCA ACT ATT AGT GGT CGT GGT GTT ACC ACA TAC TAC GCA GAC TCC
E W V S T I S G R G V T T Y Y A D S
|—— CDR 2 ——

GTG AAG GGC CGG TTC ACC ATC TCC AGA GAC AAT TCC AAG AAC ACA CTG TAT TTG
V K G R F T I S R D N S K N T L Y L
——|

CAA ATG AAC AGC CTG AGA GCC GAC GAC ACG GCC CTA TAT TAC TGT GCG AAA GAT
Q M N S L R A D D T A L Y Y C A K D
|——

CGT ACC CGC TAC TAC GGT ATG GAC GTC TGG GGC CAA GGG ACC ACG GTC ACC GTC
R T R Y Y G M D V W G Q G T T V T V
—— CDR3 ——|

TCC TCA GCT TCC ACC AAG GGC CCA TCG GTC TTC CCC CTG GCA CCC TCC TCC AAG
S S A S T K G P S V F P L A P S S K
$V_H$ End --||---------- $C_H$ Start AGC ACC TCT GGG GGC ACA GCG GCC CTG GGC TGC CTG GTC AAG GAC TAC TTC
S T S G G T A A L G C L V K D Y F CCC GAA CCG GTG ACG GTG TCG TGG AAC TCA GGC GCC CTG ACC AGC GGC GTG
P E P V T V S W N S G A L T S G V CAC ACC TTC CCG GCT GTC CTA CAG TCC TCA GGA CTC TAC TCC CTC AGC AGC GTG
H T F P A V L Q S S G L Y S L S S V GTG ACC GTG CCC TCC AGC AGC TTG GGC ACC CAG ACC TAC ATC TGC AAC GTG AAT
V T V P S S S L G T Q T Y I C N V N

Figure 30 (cont'd)

CAC AAG CCC AGC AAC ACC AAG GTG GAC AAG AAA GTT GAG CCC AAA TCT TGT GAA
H K P S N T K V D K K V E P K S C E
$C_H$ end --------||------

TTT GGT GGC GCG CCG GAG TTC CCG AAA CCG TCC ACC CCG CCG GGT TCT TCT GGT
F G G A P E F P K P S T P P G S S G
-------------------- Linker 2 --------------------

CTT GAG GGC GGC AGC CTG GCC GCG CTG ACC GCG CAC CAG GCC TGC CAC CTG
L E G G S L A A L T A H Q A C H L
----||---------- ETA $_{252\text{-}608}$ CCG CTG GAG ACT TTC ACC CGT CAT CGC CAG CCG CGC GGC TGG GAA CAA CTG
P L E T F T R H R Q P R G W E Q L GAG CAG TGC GGC TAT CCG GTG CAG CGG CTG GTC GCC CTC TAC CTG GCG GCG
E Q C G Y P V Q R L V A L Y L A A CGA CTG TCA TGG AAC CAG GTC GAC CAG GTG ATC CGC AAC GCC CTG GCC AGC
R L S W N Q V D Q V I R N A L A S CCC GGC AGC GGC GGC GAC CTG GGC GAA GCG ATC CGC GAG CAG CCG GAG CAG
P G S G G D L G E A I R E Q P E Q GCA CGT CTC GCT CTG ACC CTG GCC GCC GCC GAG AGC GAG CGC TTC GTC CGG
A R L A L T L A A A E S E R F V R CAG GGC ACC GGC AAC GAC GAG GCA GGC GCT GCA AGC GCC GAC GTG GTG AGC
Q G T G N D E A G A A S A D V V S CTG ACC TGC CCG GTC GCC GCC GGT GAA TGC GCG GGC CCG GCG GAC AGC GGC
L T C P V A A G E C A G P A D S G GAC GCC CTG CTG GAG CGC AAC TAT CCC ACT GGC GCG GAG TTC CTC GGC GAC
D A L L E R N Y P T G A E F L G D GGT GGC GAC GTC AGC TTC AGC ACC CGC GGC ACG CAG AAC TGG ACG GTG GAG
G G D V S F S T R G T Q N W T V E CGG CTG CTC CAG GCG CAC CGC CAA CTG GAG GAG CGC GGC TAT GTG TTC GTC
R L L Q A H R Q L E E R G Y V F V GGC TAC CAC GGC ACC TTC CTC GAA GCG GCG CAA AGC ATC GTC TTC GGC GGG
G Y H G T F L E A A Q S I V F G G GTG CGC GCG CGC AGC CAG GAT CTC GAC GCG ATC TGG CGC GGT TTC TAT ATC
V R A R S Q D L D A I W R G F Y I GCC GGC GAT CCG GCG CTG GCC TAC GGC TAC GCC CAG GAC CAG GAA CCC GAC
A G D P A L A Y G Y A Q D Q E P D

GCG CGC GGC CGG ATC CGC AAC GGT GCC CTG CTG CGG GTC TAT GTG CCG CGC

Figure 30 (cont'd)

```
        A   R   G   R   I   R   N   G   A   L   L   R   V   Y   V   P   R
TCC AGC CTG CCG GGC TTC TAC CGC ACC GGC CTG ACC CTG GCC GCG CCG GAG
 S   S   L   P   G   F   Y   R   T   G   L   T   L   A   A   P   E

GCG GCG GGC GAG GTC GAA CGG CTG ATC GGC CAT CCG CTG CCG CTG CGC CTG
 A   A   G   E   V   E   R   L   I   G   H   P   L   P   L   R   L

GAC GCC ATC ACC GGC CCC GAG GAG GAA GGC GGG CGC CTG GAG ACC ATT CTC
 D   A   I   T   G   P   E   E   E   G   G   R   L   E   T   I   L

GGC TGG CCG CTG GCC GAG CGC ACC GTG GTG ATT CCC TCG GCG ATC CCC ACC
 G   W   P   L   A   E   R   T   V   V   I   P   S   A   I   P   T

GAC CCG CGC AAC GTC GGT GGC GAC CTC GAC CCG TCC AGC ATC CCC GAC AAG
 D   P   R   N   V   G   G   D   L   D   P   S   S   I   P   D   K

GAA CAG GCG ATC AGC GCC CTG CCG GAC TAC GCC AGC CAG CCC GGC AAA CCG
 E   Q   A   I   S   A   L   P   D   Y   A   S   Q   P   G   K   P

CCG CAT CAC CAC CAT CAC CAT AAA GAC GAA CTG TAG TGA CTC GAC CTG CAG GTC
 P   H   H   H   H   H   H   K   D   E   L
     |------------- 6xHis --------------|           end of ETA ------|

TAT GGA ACG ATA AAT GCC CAT GAA AAT TCT ATT TCA AGG AGA CAG TCA TA ATG AAA
                                                                    M   K
                                                                    |_____
TAC CTA TTG CCT ACG GCA GCC GCT GGA TTG TTA TTA CTC GCT GCC CAA CCA
 Y   L   L   P   T   A   A   A   G   L   L   L   L   A   A   Q   P
_____PelB Leader Sequence_____ _____

GCG ATG GCG CAT CAC CAT CAC CAT CAC TCC TAT GAG CTG ACT CAG CCA CCC TCA
 A   M   A   H   H   H   H   H   H   S   Y   E   L   T   Q   P   P   S
_____|  |------------- 6xHis --------------| |---------- V_L Start

GTG TCC GTG TCC CCA GGA CAG ACA GCC AGC ATC ACC TGC TCT GGA AAT AAA TTG
 V   S   V   S   P   G   Q   T   A   S   I   T   C   S   G   N   K   L
                                                     |⎯⎯⎯⎯⎯⎯⎯⎯⎯⎯⎯⎯⎯⎯⎯

GGG GAT AAA TAT GCT TGC TGG TAT CAG CAG AAG TCA GGC CAG TCC CCT GTG CTG
 G   D   K   Y   A   C   W   Y   Q   Q   K   S   G   Q   S   P   V   L
CDR1 ⎯⎯⎯⎯⎯⎯⎯⎯⎯⎯⎯⎯⎯⎯⎯⎯|

GTC ATC TAT CAA GAT TCC AAG CGG CCC TCA GGG ATC CCT GAG CGA TTC TCT GGC
 V   I   Y   Q   D   S   K   R   P   S   G   I   P   E   R   F   S   G
         |⎯⎯⎯⎯⎯⎯⎯⎯ CDR 2 ⎯⎯⎯⎯⎯⎯⎯⎯|

TCC AAC TCT GGG AAC ACA GCC ACT CTG ACC ATC AGC GGG ACC CAG GCT TTG GAT
 S   N   S   G   N   T   A   T   L   T   I   S   G   T   Q   A   L   D

GAG GCT GAC TAT TAT TGT CAG GCG TGG GAC AAC AGC ACT GCG GTA TTC GGC GGA
```

Figure 30 (cont'd)

E A D Y Y C Q A W D N S T A V F G G
CDR 3 (Q A W D N S T A V)

GGG ACC AGG CTG ACC GTC CTA GGT CAG CCC AAG GCT GCC CCC TCG GTC ACT CTG
G T K L T V L G Q P K A A P S V T L
$V_L$ End ----| |---------- $C_L$ Start TTC CCG CCC TCC TCT GAG GAG CTC CAA GCC AAC AAG GCC ACA CTA GTG TGT CTG
F P P S S E E L Q A N K A T L V C L ATC AGT GAC TTC TAC CCG GGA GCT GTG ACA GTG GCC TGG AAG GCA GAT AGC AGC
I S D F Y P G A V T V A W K A D S S CCC GTC AAG GCG GGA GTG GAG ACC ACC ACA CCC TCC AAA CAG AGC AAC AAC AAG
P V K A G V E T T T P S K Q S N N K TAC GCG GCC AGC AGC TAC CTG AGC CTG ACG CCC GAG CAG TGG AAG TCC CAC
Y A A S S Y L S L T P E Q W K S H AGA AGC TAC AGC TGC CAG GTC ACG CAT GAA GGG AGC ACC GTG GAG AAG ACA GTG
R S Y S C Q V T H E G S T V E K T V GCC CCT ACA GAA TGT TCA TAG TGA *<u>CTC GAG</u>* (SEQ ID NO:50)
A P T E C S *XhoI* (SEQ ID NO:51)
$C_L$ End -------|

Figure 31: Gamma cassette of VB6-213-$C_L$-de-bouganin
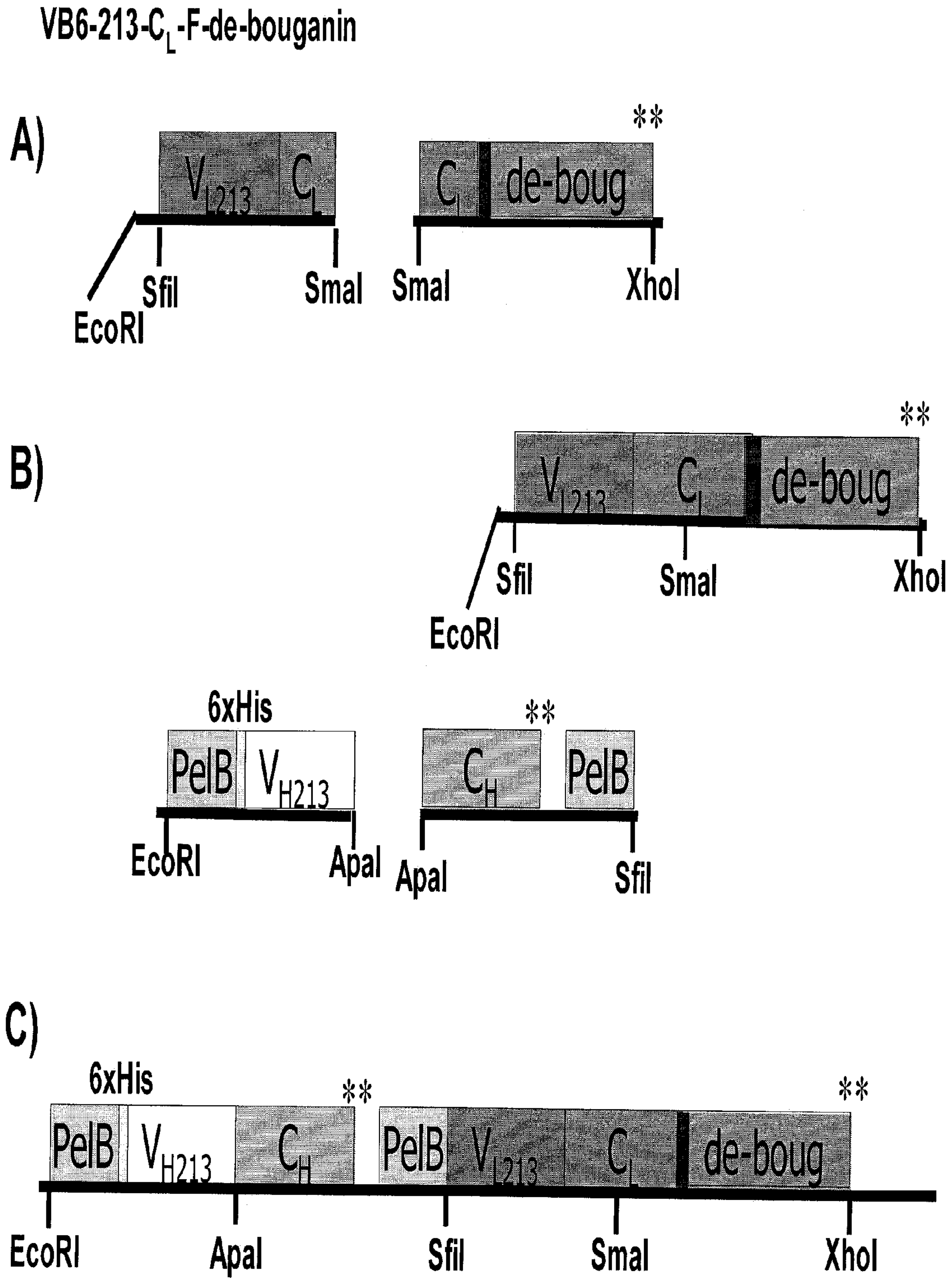

Figure 32: Gamma cassette of VB6-213-Fab-PE
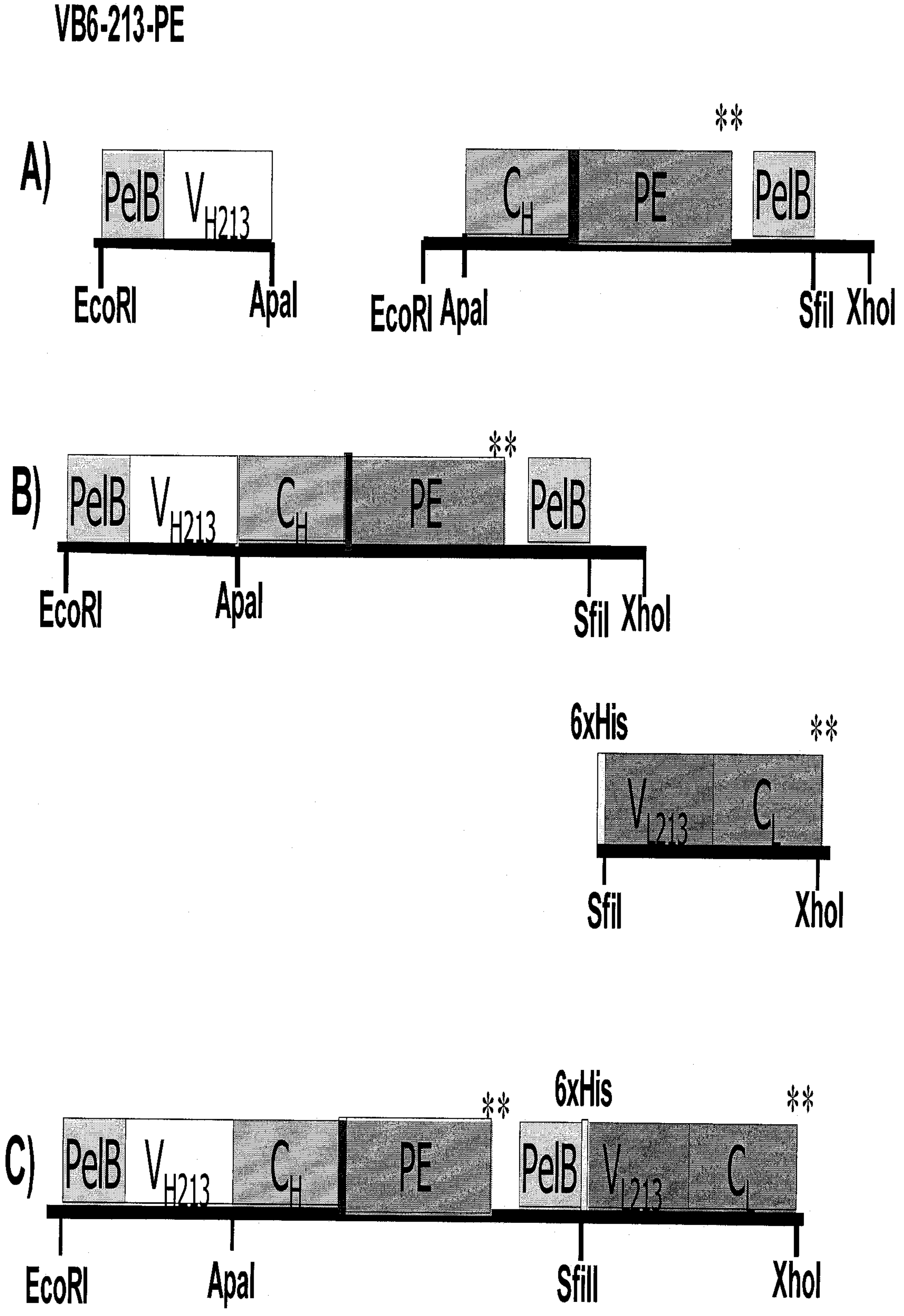

C-33-A

DU-145

ANTIBODIES AGAINST A CANCER-ASSOCIATED EPITOPE OF VARIANT HNRNPG AND USES THEREOF

FIELD OF THE INVENTION

The present application relates to a novel antibody and antigens, and methods and compositions for treating and detecting cancer.

BACKGROUND OF THE INVENTION

In the year 2000, an estimated 22 million people were suffering from cancer worldwide and 6.2 millions deaths were attributed to this class of diseases. Every year, there are over 10 million new cases and this estimate is expected to grow by 50% over the next 15 years (WHO, World Cancer Report. Bernard W. Stewart and Paul Kleihues, eds. IARC Press, Lyon, 2003). Current cancer treatments are dominated by invasive surgery, radiation therapy and chemotherapy approaches, which are frequently ineffective and can have potentially severe side-effects, non-specific toxicity and/or cause traumatizing changes to ones body image and/or quality of life. One of the causes for the inadequacy of current cancer treatments is their lack of selectivity for affected tissues and cells. Treatment with greater selectivity for cancer cells would leave normal cells unharmed thus improving outcome, side-effect profile and quality of life.

The selectivity of cancer treatment can be improved by targeting molecules that are specific to cancer cells and not found on normal cells. These molecules can then be used as a target to antibody-based diagnostic or therapeutics or for drugs capable of altering their function.

HnRNPG or heterogeneous ribonucleoprotein G is also known as RBMX. It is primarily localized in the nucleus where it has been found to form complexes with several proteins, to regulate the splicing of some genes, and to influence the DNA repair functions of p53 (Li et al 2003, Venables et al 2000; Najib et al 2005). Many of these mechanisms have been linked to tumor formation (U.S. Pat. No. 6,627,405 B1; Nandabalan et al 2003). Recently, Shin et al 2006 and 2007 have reported that normal HnRNPG has tumor suppressor functions, that expression has been found to be diminished in tumor cells and have established a link between p53 regulated DNA repair functions and normal HnRNPG expression. Shin et al 2006 describes a tumor associated form of HnRNPG with a single amino acid change at residue 22 in the RNA binding domain and reports detection by immunohistochemistry of membrane associated expression of HnRNPG.

PSCA is a 123 amino-acid glycosyl-phosphotidyl-inositol (GPI)-linked glycoprotein found on the cell surface. Its mRNA is expressed in normal tissues but up-regulated in neoplastic tissues (Gu et al., Cancer Res., 2005, 65:9495). Its overexpression has been linked to prostate cancer (Zhigang and Wenlv, World J. Surg. Oncol., 2004a, 2:13, Zhigang and Wenlv, Jpn. J. Clin. Oncol., 2004b, 34:414), pancreatic cancer (Wente et al., Pancreas, 2005, 31:119) and bladder cancer (Amara et al., Cancer Res., 2001, 61:4660). Anti-PSCA monoclonal antibodies, humanized or obtained from transgenic mouse (Xenomouse) have been developed (U.S. Pat. No. 6,825,226, US 2006/0269557, WO 2005/118864) and some are being evaluated for the treatment of cancer.

SUMMARY OF THE INVENTION

The present inventors have identified a novel antibody and antigens. Specifically, the inventors have identified a novel cancer-specific human antibody, which binds to several types of cancer cells including, lung cancer, liver cancer, prostate cancer, skin cancer (including melanoma), pancreatic cancer, head and neck cancer and breast cancer. Importantly, the antibody does not significantly bind to normal tissue making it a suitable candidate for cancer therapy and diagnosis. The inventors have also identified the antigens and epitopes to which the novel antibody specifically binds.

The inventors have cloned and sequenced the antibody and determined the sequence of the antibody light and heavy chain variable regions and complementarity determining regions 1, 2 and 3.

Accordingly, the application discloses isolated light chain complementarity determining region 1 (CDR1) comprising the amino acid sequence SGNKLGDKYAC (SEQ ID NO:7); isolated light chain complementarity determining region 2 (CDR2) comprising the amino acid sequence QDSKRPS (SEQ ID NO:8); and isolated light chain complementarity determining region 3 (CDR3) comprising the amino acid sequence QAWDNSTAV (SEQ ID NO:9); and isolated heavy chain CDR1 comprising the amino acid sequence SYAMS (SEQ ID NO:10); isolated heavy chain CDR2 comprising the amino acid sequence TISGRGVTTYYADSVKG (SEQ ID NO:11); and isolated heavy chain CDR3 comprising the amino acid sequence DRTRYYGMDV (SEQ ID NO:12).

The application also discloses isolated nucleic acid sequences encoding the light chain CDR1 comprising the amino acid sequence SGNKLGDKYAC (SEQ ID NO:7); the light chain CDR2 comprising the amino acid sequence QDSKRPS (SEQ ID NO:8); the light chain CDR3 comprising the amino acid sequence QAWDNSTAV (SEQ ID NO:9); the heavy chain CDR1 comprising the amino acid sequence SYAMS (SEQ ID NO:10); the heavy chain CDR2 comprising the amino acid sequence TISGRGVTTYYADSVKG (SEQ ID NO:11); and the heavy chain CDR3 comprising the amino acid sequence DRTRYYGMDV (SEQ ID NO:12).

Additional aspects disclosed in the present application are isolated light chain variable regions comprising light chain CDR1, CDR2 and/or CDR3 disclosed herein (SEQ ID NOS: 7-9), and isolated heavy chain variable regions comprising heavy chain CDR1, CDR2 and/or CDR3 disclosed herein (SEQ ID NOS:10-12). In one embodiment, the light chain variable region comprises the amino acid sequence shown in FIG. 2 (SEQ ID NO:16). In another embodiment, the heavy chain variable region comprises the amino acid sequence shown in FIG. 1 (SEQ ID NO:14).

The application also discloses an isolated nucleic acid sequence encoding the light chain variable region disclosed herein, and an isolated nucleic acid sequence encoding the heavy chain variable region disclosed herein. In one embodiment, the nucleic acid sequence encoding the light chain variable region comprises the nucleic acid sequence shown in FIG. 2 (SEQ ID NO:15). In another embodiment, the nucleic acid sequence encoding the heavy chain variable region comprises the nucleic acid sequence shown in FIG. 1 (SEQ ID NO:13).

Another aspect of the present application is a binding protein, preferably an antibody or antibody fragment, that comprises at least one light chain complementarity determining region disclosed herein (i.e. one or more of SEQ ID NOS:7-9) and/or at least one heavy chain complementarity determining region disclosed herein (i.e. one or more of SEQ ID NO:10-12). The application also discloses a binding protein, preferably an antibody or antibody fragment, that comprises the light chain variable regions disclosed herein and/or the heavy chain variable regions disclosed herein.

As mentioned above, the inventors have also identified the antigens to which the binding proteins disclosed herein bind. Accordingly, the application discloses binding proteins that bind to prostate stem cell antigen (SEQ ID NO:17) and variant HnRNPG. The inventors also identified the epitopes on the antigens to which the binding proteins disclosed herein bind. Accordingly, the application discloses binding proteins that bind to a polypeptide comprising the amino acid YSCKAQVSNED (SEQ ID NO:23), YSCKAQVSN (SEQ ID NO:41), YSCKAQYSNRD (SEQ ID 111) or YSCKAQ$X_1$SN$X_2$D where $X_1$=Y or V and $X_2$=R or E (SEQ ID 112).

In addition, the application discloses compositions comprising the binding proteins disclosed herein, such as antibodies and antibody fragments, and a pharmaceutically acceptable excipient, carrier, buffer or stabilizer.

Further, the application discloses isolated nucleic acid sequences that encode the binding proteins disclosed herein.

Another aspect of the present application is an immunoconjugate comprising (1) a binding protein disclosed herein, preferably an antibody or antibody fragment that binds to an antigen or molecule on or in a cancer cell, attached to (2) an effector molecule. A further aspect of the application is an immunoconjugate comprising (1) a binding protein disclosed herein, preferably an antibody or antibody fragment that binds to an antigen or molecule that is internalized by a cancer cell, attached to (2) an effector molecule. In a preferred embodiment, the effector molecule is (i) a label, which can generate a detectable signal, directly or indirectly, or (ii) a cancer therapeutic agent, which is either cytotoxic, cytostatic or otherwise prevents or reduces the ability of the cancer cells to divide and/or metastasize. Preferably, the cancer therapeutic agent is a toxin or cytotoxin. In one embodiment, the immunoconjugate comprises the amino acid sequence defined by SEQ ID NO:49. In another embodiment, the immunoconjugate comprises the amino acid sequence defined by SEQ ID NO:51.

The application also provides for isolated nucleic acid sequences that encode the immunoconjugates disclosed herein. In one embodiment, the isolated nucleic acid sequence encodes the immunoconjugate comprising the amino acid sequence of SEQ ID NO:49. In another embodiment, the isolated nucleic acid sequence comprises SEQ ID NO:48. In a further embodiment, the isolated nucleic acid sequence encodes the immunoconjugate comprising the amino acid sequence of SEQ ID NO:51. In another embodiment, the isolated nucleic acid sequence comprises SEQ ID NO:50.

The application also provides compositions comprising an immunoconjugate disclosed herein and uses of the immunoconjugate for the manufacture of a medicament for treating or preventing cancer, and diagnostic purposes. In addition, the application provides methods of treating or preventing cancer using an immunoconjugate disclosed herein and related kits.

A further aspect of the present application is a method of detecting or monitoring cancer in a subject comprising the steps of:

(1) contacting a test sample taken from said subject with a binding protein or immunoconjugate disclosed herein and that binds specifically to an antigen on or in the cancer cell to produce a binding protein-antigen complex;

(2) measuring the amount of binding protein-antigen complex in the test sample; and (3) comparing the amount of binding protein-antigen complex in the test sample to a control.

Another aspect of the application is a diagnostic agent comprising an immunoconjugate disclosed herein, wherein the effector molecule is a label, which can generate a detectable signal, directly or indirectly.

The application also includes an isolated protein that can specifically bind with one of the binding proteins disclosed herein, nucleic acid sequences and uses thereof.

The inventors have identified the antigens to which the binding proteins disclosed herein bind (namely, prostate stem cell antigen and a variant HnRNPG), and the inventors have identified the epitopes to which the binding proteins disclosed herein bind (namely, SEQ ID NOS: 23, 41, 111 and 112). Thus, the application provides an isolated polypeptide comprising the amino acid sequence of SEQ ID NOS: 17, 71, 23, 41, 111 or 112, or variants thereof. Further, the application provides an isolated polypeptide consisting of the amino acid sequence of SEQ ID NOS: 17, 71, 23, 41, 111 or 112, or variants thereof. The application also provides isolated nucleic acid sequences encoding these polypeptides.

The application discloses the use of an antigen or epitope disclosed herein in the treatment and diagnosis of cancer. Accordingly, the application discloses a method of detecting or monitoring cancer in a subject having or suspected of having cancer, comprising detecting an antigen or epitope disclosed herein on or in a cell in the sample, wherein cancer is indicated, if an antigen or epitope is detected or overexpressed on or in the cell.

Another aspect of the present application is a method for detecting or monitoring cancer by screening for the presence or expression of variant HnRNPG. In one embodiment, the method comprises the steps:

(a) determining the expression of variant HnRNPG in a test sample from a subject; and (b) comprising the expression of variant HnRNPG with a control;

wherein a difference in expression of variant HnRNPG between the control and test sample is indicative of cancer.

The application also discloses pharmaceutical compositions comprising an effective amount of an antigen or epitope disclosed herein, the isolated nucleic acid sequences encoding an antigen or epitope disclosed herein or the recombinant expression vectors comprising nucleic acid sequences that encode an antigen or epitope disclosed herein, with a pharmaceutically acceptable excipient, carrier, buffer or stabilizer.

A further aspect of the application is the use of an antigen or epitope disclosed herein, the isolated nucleic acid sequences encoding an antigen or epitope disclosed herein or the recombinant expression vectors comprising nucleic acid sequences that encode an antigen or epitope disclosed herein to elicit an immune response in a subject.

A further aspect of the application is the use of an antigen or epitope disclosed herein, the isolated nucleic acid sequences encoding an antigen or epitope disclosed herein or the recombinant expression vectors comprising nucleic acid sequences that encode an antigen or epitope disclosed herein to treat or prevent cancer.

In addition, the application includes methods for treating or preventing cancer in a subject comprising administering to the subject or a cell from the subject an effective amount of an antigen or epitope disclosed herein, the isolated nucleic acid sequences encoding an antigen or epitope disclosed herein or the recombinant expression vectors comprising nucleic acid sequences that encode an antigen or epitope disclosed herein.

The application also includes methods for inducing an immune response in a subject against an antigen or epitope disclosed herein comprising administering to the subject or a cell from the subject an effective amount of an antigen or epitope disclosed herein, the isolated nucleic acid sequence encoding an antigen or epitope disclosed herein or a recombinant expression vector comprising nucleic acid sequences that encode an antigen or epitope disclosed herein.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 1 shows the nucleotide (SEQ ID NO:13) and amino acid (SEQ ID NO: 14) sequences of the gamma, VH3 chain of VB1-213.

FIG. 2 shows the nucleotide (SEQ ID NO:15) and amino acid (SEQ ID NO: 16) sequences of the lambda, VL3 chain of VB1-213.

FIG. 9 is a mass spectral analysis of peptide ions extracted from DU-145: FIG. 9A represents the TOFMS scan with all multiply charged peptide ions and FIG. 9B represents the deconvoluted spectrum with singly charged peptide ions after mass reconstruction.

FIG. 11 shows MS/MS ion fragmentation of the neutral peptide Mr. 1481.9584, appearing as a doubly charged molecule (742.00000, 2+).

FIG. 12 A: shows the complete mapping of the peptides obtained and the sequence coverage of the variant HnRNPG (SEQ ID NO:71). The amino acids in bold represent the amino acid sequences identified from MS analysis. The underlined portion represents the de novo sequenced peptide that shows amino acid changes at positions 216, 218, 219 and 222 (SEQ ID NO:70), and B: shows the amino acid sequence of normal human HnRNPG. The region corresponding to the variant is underlined and amino acids that are substituted are shown in bold.

FIG. 13 shows TOFMS scans of peptides obtained from a 1D gel immunoprecipitation and Western blot with VB1-213 from the DU-145 cell line to detect the presence of all peptide ions in the sample: FIG. 13A represents the TOF_MS scan with all multiply charged peptide ions and FIG. 13B represents the deconvoluted spectrum with singly charged peptide ions.

FIG. 14 shows TOFMS scans of peptides obtained from a 1D gel immunoprecipitation and Western blot with VB1-213 from the SKBR-3cell line, to detect the presence of all peptide ions in the sample: FIG. 14A represents the TOF_MS scan with all multiply charged peptide ions and FIG. 14B represents the deconvoluted spectrum with singly charged peptide ions.

FIG. 15 shows TOFMS scans of peptides obtained a 1D gel immunoprecipitation and Western blot with VB1-213 from the from Panc-1, to detect the presence of all peptide ions in the sample: FIG. 15A represents the TOF_MS scan with all multiply charged peptide ions and FIG. 15B represents the deconvoluted spectrum with singly charged peptide ions.

FIG. 18 complete mapping of the peptides obtained and sequence coverage of prostate stem cell antigen, NCBI accession # GI/9367212. The amino acids in bold and underlined represent the sequences of amino acids identified from MS analysis.

FIG. 19 shows MS/MS ion fragmentation of the neutral peptide Mr. 1866.00, appearing as a triply charged molecule (623.00000, 3+). The peptide sequence exactly matched the peptide from prostate stem cell antigen.

FIG. 20 shows Western blots of Panc-1 and Daudi membrane preparations, which were immunoprecipitated with anti-PSCA and probed with anti-PSCA and VB1-213.

FIG. 21B demonstrates the ability of HP1 to competitively inhibit the binding of VB1-213 to DU-145, as compared to 4B5-IgG anti-EGFR and anti-PSCA. Peptide concentrations ranging from 10× to 100× were mixed with the antibody and the displacement in binding to DU-145 was monitored by flow analysis. C, D and E represent the binding profiles of different antibodies to peptides PSPep1, PSPep2 and PSPep3 (negative) and F, G and H show the binding of VB1-213 to DU-145 in the presence of increasing concentrations of various peptides.

FIG. 23 shows VB6-213-CL-de-bouganin nucleotide sequence (SEQ ID NO:42).

FIG. 24 shows VB6-213-Fab-PE nucleotide sequence (SEQ ID NO:43).

FIG. 25 shows amino acid sequence of $V_{H213}$-$C_H$ (SEQ ID NO:44).

FIG. 26 shows amino acid sequence of $V_{L213}$-$C_L$-de-bouganin (SEQ ID NO:45).

FIG. 27 shows amino acid sequence of $V_{H213}$-$C_H$-PE (SEQ ID NO:46).

FIG. 28 shows amino acid sequence of $V_{L213}$-$C_L$ (SEQ ID NO:47).

FIG. 29 shows the VB6-213-$C_L$-de-bouganin construct. The nucleotide sequence is depicted (SEQ ID NO:48) and the amino acid sequence is depicted (SEQ ID NO:49).

FIG. 30 shows the VB6-213-Fab-PE construct. The nucleotide sequence is depicted (SEQ ID NO:50) and the amino acid sequence is depicted (SEQ ID NO:51).

FIG. 31 shows gamma cassette of VB6-213-$C_L$-de-bouganin.

FIG. 32 shows gamma cassette of VB6-213-Fab-PE.

DETAILED DESCRIPTION OF THE INVENTION

(A) Definitions

Figure 3:
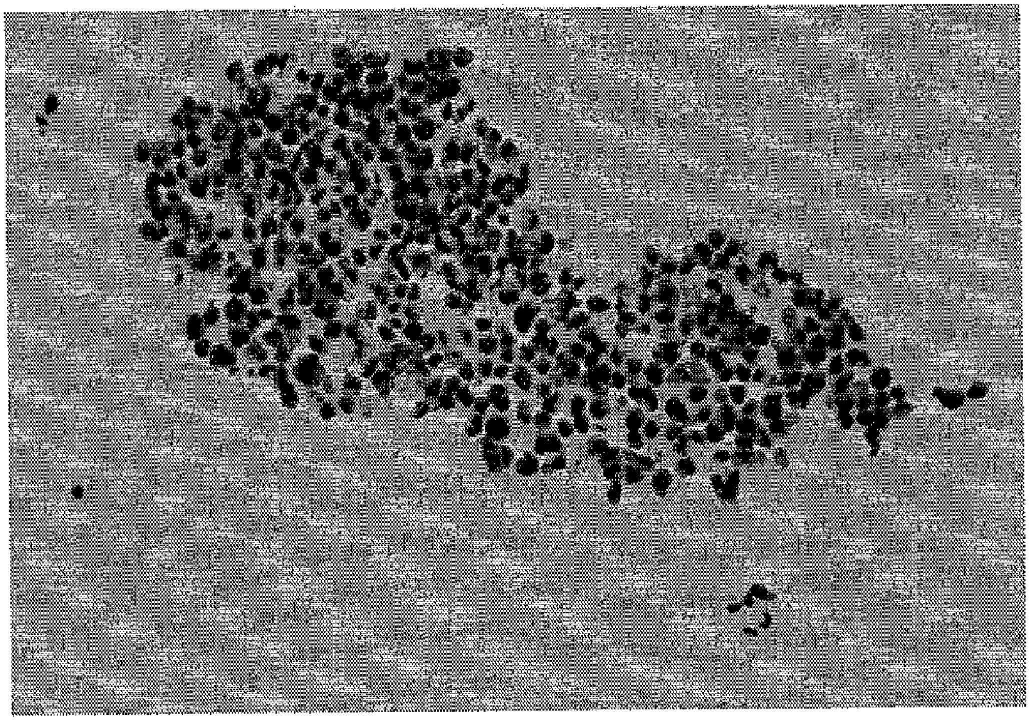
FIG. 3 shows SK-OV-3 fixed cell pellet stained with VBI-213; 200X; membrane, cytoplasmic and nuclear staining observed.

The term "a cell" includes a single cell as well as a plurality or population of cells. Administering an agent to a cell includes both in vitro and in vivo administrations.

The term "administered systemically" as used herein means that the immunoconjugate and/or other cancer therapeutic may be administered systemically in a convenient manner such as by injection (subcutaneous, intravenous, intramuscular, etc.), oral administration, inhalation, transdermal administration or topical application (such as topical cream or ointment, etc.), suppository applications, or means of an implant. An implant can be of a porous, non-porous, or gelatinous material, including membranes, such as sialastic membranes, or fibers. Suppositories generally contain active ingredients in the range of 0.5% to 10% by weight.

The term "amino acid" includes all of the naturally occurring amino acids as well as modified amino acids.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include without limitations Fab, Fab', $F(ab')_2$, scFv, dsFv, ds-scFv, dimers, minibodies, diabodies, and multimers thereof, multispecific antibody fragments and Domain Antibodies. Antibodies can be fragmented using conventional techniques. For example, $F(ab')_2$ fragments can be generated by treating the antibody with pepsin. The resulting $F(ab')_2$ fragment can be treated to reduce disulfide bridges to produce Fab' fragments. Papain digestion can lead to the formation of Fab fragments. Fab, Fab' and $F(ab')_2$, scFv, dsFv, ds-scFv, dimers, minibodies, diabodies, bispecific antibody fragments and other fragments can also be synthesized by recombinant techniques.

The term "antibody or antibody fragment disclosed herein" comprises at least one light chain complementarity determining region disclosed herein (i.e. one or more of SEQ ID NOS:7-9) and/or at least one heavy chain complementarity determining region disclosed herein (i.e. one or more of SEQ ID NOS:10-12). In one embodiment, the antibody or antibody fragment comprises the light chain CDR sequences (SEQ ID NOS:7-9) and/or the heavy chain CDR sequences (SEQ ID NOS:10-12). In another embodiment, the antibody or antibody fragment comprises the amino acid of SEQ ID NO: 16 (light chain variable region) and/or the amino acid of SEQ ID NO:14 (heavy chain variable region). The term also includes antibodies or antibody fragments that bind to an antigen or an epitope disclosed herein. The antibody or antibody fragments also include functional variants of the sequences so that the antibody or antibody fragment can bind to the cancer cell without substantially binding to normal cells.

The term "antigen disclosed herein" or "cancer-associated antigen disclosed herein" refers to prostate stem cell antigen (SEQ ID NO:17) and to a cancer-associated variant of HnRNPG, and fragments thereof. The term includes polypeptides comprising an epitope disclosed herein.

The term "cancer-associated variant of HnRNPG" or "variant HnRNPG" as used herein refers to a novel variant of HnRNPG. In one embodiment, the variant HnRNPG is preferentially expressed in cancer cells. In another embodiment, the variant HnRNPG is associated with the plasma membrane. In a further embodiment, the variant HnRNPG is co-expressed with Prostate Stem Cell Antigen (PSCA). In another embodiment, the variant HnRNPG has the amino acid sequence of HnRNPG (SEQ ID NO:113) with one or more amino acid substitutions at positions 216, 218, 219 and/or 222. In an embodiment, the variant HnRNPG comprises the amino acid sequence of SEQ ID NO:71. In another embodiment, the variant HnRNPG consists of the amino acid sequence of SEQ ID NO:71. In another embodiment, the variant HnRNPG has the amino acid sequence of HnRNPG (SEQ ID NO:113) with substitutions at positions 214 to 224 with the amino acid sequence of SEQ ID NO:111 or 112.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)−600/I), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

The term "binding protein" as used herein refers to proteins that specifically bind to another substance such as a cancer-associated antigen or epitope disclosed herein. In an embodiment, binding proteins are antibodies or antibody fragments.

By "biologically compatible form suitable for administration in vivo" is meant a form of the substance to be administered in which any toxic effects are outweighed by the therapeutic effects.

The term "cancer" as used herein includes any cancer that can be bound by a binding protein disclosed herein, preferably an antibody or antibody fragment disclosed herein.

The term "cancer cell" includes cancer or tumor-forming cells, transformed cells or a cell that is susceptible to becoming a cancer or tumor-forming cell.

The term "complementary" refers to nucleic acid sequences capable of base-pairing according to the standard Watson-Crick complementary rules, or being capable of hybridizing to a particular nucleic acid segment under stringent conditions.

A "conservative amino acid substitution" as used herein, is one in which one amino acid residue is replaced with another amino acid residue without abolishing the protein's desired properties.

The term "control" as used herein refers to a sample from a subject or a group of subjects who are either known as having cancer or not having cancer, or known as having a specific grade or severity of cancer.

The term "controlled release system" as used means the immunoconjugate and/or other cancer therapeutic disclosed herein that can be administered in a controlled fashion. For example, a micropump may deliver controlled doses directly into the area of the tumor, thereby finely regulating the timing and concentration of the pharmaceutical composition (see, e.g., Goodson, 1984, in Medical Applications of Controlled Release, vol. 2, pp. 115-138).

The term "derivative of a peptide" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

The phrase "detecting or monitoring cancer" refers to a method or process of determining if a subject has or does not have cancer, the extent of cancer, the severity of cancer and/or grade of cancer.

The term "direct administration" as used herein means the cancer therapeutic may be administered, without limitation, intratumorally, intravascularly, and peritumorally. For example, the cancer therapeutic may be administered by one or more direct injections into the tumor, by continuous or discontinuous perfusion into the tumor, by introduction of a reservoir of the cancer therapeutic, by introduction of a slow-release apparatus into the tumor, by introduction of a slow-release formulation into the tumor, and/or by direct application onto the tumor. By the mode of administration "into the tumor," introduction of the cancer therapeutic to the area of the tumor, or into a blood vessel or lymphatic vessel that substantially directly flows into the area of the tumor, is included.

As used herein, the phrase "effective amount" means an amount effective, at dosages and for periods of time necessary to achieve the desired result. Effective amounts of therapeutic may vary according to factors such as the disease state, age, sex, weight of the animal. Dosage regime may be adjusted to provide the optimum therapeutic response. For example, several divided doses may be administered daily or the dose may be proportionally reduced as indicated by the exigencies of the therapeutic situation.

The term "eliciting an immune response" or "inducing an immune response" as used herein means initiating, triggering, causing, enhancing, improving or augmenting any response of the immune system, for example, of either a humoral or cell-mediate nature. The initiation or enhancement of an immune response can be assessed using assays known to those skilled in the art including, but not limited to, antibody assays (for example ELISA assays), antigen specific cytotoxicity assays and the production of cytokines (for example ELISPOT assays). Preferably, the isolated proteins, nucleic acid sequences or recombinant expression vectors disclosed herein, and the methods disclosed herein, trigger or enhance a cellular immune response, more preferably a T cell response.

The term "epitope disclosed herein" or "cancer-associated epitope disclosed herein" refers to the site on the antigens disclosed herein that is recognized by the antibody disclosed herein. In one embodiment, the epitope comprises the amino acid sequence of SEQ ID NO:23, 41, 111 or 112. In another embodiment, the epitope consists of the amino acid sequence of SEQ ID NO: 23, 41, 111 or 112.

The term "heavy chain complementarity determining region" as used herein refers to regions of hypervariability within the heavy chain variable region of an antibody molecule. The heavy chain variable region has three complementarity determining regions termed heavy chain complementarity determining region 1, heavy chain complementarity determining region 2 and heavy chain complementarity determining region 3 from the amino terminus to carboxy terminus.

The term "heavy chain variable region" as used herein refers to the variable region of a heavy chain.

The term "immunoconjugate disclosed herein" comprises (1) a binding protein, preferably an antibody or antibody fragment, disclosed herein attached to (2) an effector molecule. The effector molecule can be any molecule that one wishes to deliver to the cancer cell, including, but not limited to (i) a label, which can generate a detectable signal, directly or indirectly, or (ii) a cancer therapeutic agent, such as a toxin that is either cytotoxic, cytostatic or otherwise prevents or reduces the ability of the cancer cells to divide and/or metastasize. The term "immunotoxin disclosed herein" refers to an immunoconjugate, wherein the effector molecule is a cancer therapeutic agent, such as a toxin that is either cytotoxic, cytostatic or otherwise prevents or reduces the ability of the cancer cells to divide and/or metastasize.

The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded, and represents the sense or antisense strand. Further, the term "nucleic acid" includes the complementary nucleic acid sequences.

The term "isolated polypeptides" refers to a polypeptide substantially free of cellular material or culture medium when produced by recombinant DNA techniques, or chemical precursors or other chemicals when chemically synthesized.

The term "light chain complementarity determining region" as used herein refers to regions of hypervariability within the light chain variable region of an antibody molecule. Light chain variable regions have three complementarity determining regions termed light chain complementarity determining region 1, light chain complementarity determining region 2 and light chain complementarity determining region 3 from the amino terminus to the carboxy terminus.

The term "light chain variable region" as used herein refers to the variable region of a light chain.

The term "modified bouganin" as used here means a modified bouganin that has a reduced propensity to activate an immune response as described in PCT/CA2005/000410 and U.S. patent application Ser. No. 11/084,080, which published as US2005-0238642 A1. In one example, the modified bouganin has the amino acid sequence (SEQ ID NO: 52):

```
YNTVSFNLGEAYEYPTFIQDLRNELAKGTPVCQLPVTLQTIADDKRFV

LVDITTTSKKTVKVAIDVTDVYVVGYQDKWDGKDRAVFLDKVPTVAT

SKLFPGVTNRVTLTFDGSYQKLVNAAKADRKALELGVNKLEFSIEAIH

GKTINGQEAAKFFLIVIQMVSEAARFKYIETEVVDRGLYGSFKPNFKVL

NLENNWGDISDAIHKSSPQCTTINPALQLISPSNDPWVVNKVSQISPD

MGILKFKSSK.
```

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine.

The term "sample" as used herein refers to any fluid, cell or tissue sample from a subject which can be assayed for cancer.

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present application. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI- BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

The term "subject" as used herein refers to any member of the animal kingdom, preferably a mammal, more preferably a human being. In a preferred embodiment, the subject is suspected of having or has cancer.

As used herein, the phrase "treating or preventing cancer" refers to inhibiting of cancer cell replication, preventing transformation of a cell to a cancer-forming cell, inhibiting of cancer spread (metastasis), inhibiting of tumor growth, reducing cancer cell number or tumor growth, decreasing in the malignant grade of a cancer (e.g., increased differentiation), or improving cancer-related symptoms.

The term "variant" as used herein includes modifications or chemical equivalents of the amino acid and nucleic acid sequences disclosed herein that perform substantially the same function as the polypeptides or nucleic acid molecules disclosed herein in substantially the same way. For example, variants of polypeptides disclosed herein include, without limitation, conservative amino acid substitutions. Variants of polypeptides also include additions and deletions to the polypeptide sequences disclosed herein. In addition, variant des and variant nucleotide sequences include analogs and derivatives thereof. A variant of the cancer-associated antigen means a protein sequence that is expressed on or in cancer cells but not on or in normal cells or that is overexpressed on or in cancer cells relative to normal cells.

(B) Complementarity Determining Regions and Binding Proteins

(i) Light and Heavy Chain Complementarity Determining Regions and Light and Heavy Chain Variable Regions The application discloses provides isolated light chain complementarity determining region 1 (CDR1) comprising the amino acid sequence SGNKLGDKYAC (SEQ ID NO:7); isolated light chain complementarity determining region 2 (CDR2) comprising the amino acid sequence QDSKRPS (SEQ ID NO:8); and isolated light chain complementarity determining region 3 (CDR3) comprising the amino acid sequence QAWDNSTAV (SEQ ID NO:9). In addition, the application provides isolated heavy chain CDR1 comprising the amino acid sequence SYAMS (SEQ ID NO:10); isolated heavy chain CDR2 comprising the amino acid sequence TISGRGVTTYYADSVKG (SEQ ID NO:11); and isolated heavy chain CDR3 comprising the amino acid sequence DRTRYYGMDV (SEQ ID NO:12).

The application also discloses variants of the CDR sequences that can bind to the same epitopes or antigens recognized by the CDR sequences disclosed above.

Additional aspects of the present application are isolated light chain variable regions comprising light chain CDR1, CDR2 and/or CDR3 disclosed herein (SEQ ID NOS:7-9), and isolated heavy chain variable regions comprising heavy chain CDR1, CDR2 and/or CDR3 disclosed herein (SEQ ID NOS: 10-12). In one embodiment, the light chain variable region comprises the amino acid sequence shown in FIG. 2 (SEQ ID NO:16). In another embodiment, the heavy chain variable region comprises the amino acid sequence shown in FIG. 1 (SEQ ID NO:14).

The application also discloses variants of the isolated light chain variable regions and heavy chain variable regions that can bind to the same epitopes or antigens recognized by the isolated light chain variable regions and isolated heavy chain variable regions disclosed above.

A person skilled in the art will appreciate that the application includes variants to the amino acid sequences of SEQ ID NOS:7-12, 14 and 16, including chemical equivalents. Such equivalents include proteins that perform substantially the same function as the specific proteins disclosed herein in substantially the same way. For example, a functional variant of a CDR sequence will be able to bind to an antigen or epitope recognized by the native CDR sequence. For example, equivalents include, without limitation, conservative amino acid substitutions.

In one embodiment, the variant amino acid sequences of the light chain CDR1, CDR2 and CDR3, and the heavy chain CDR1, CDR2 and CDR3 have at least 50%, preferably at least 60%, more preferably at least 70%, most preferably at least 80%, even more preferably at least 90%, and even most preferably 95% sequence identity to SEQ ID NOS:7-12, respectively.

In another embodiment, the variant amino acid sequences of the light chain variable region and the heavy chain variable region have at least 50%, preferably at least 60%, more preferably at least 70%, most preferably at least 80%, even more preferably at least 90% and even most preferably 95% sequence identity to SEQ ID NOS:16 and 14, respectively.

The application also discloses an isolated nucleic acid sequence encoding the light chain variable region disclosed herein and an isolated nucleic acid sequence encoding the heavy chain variable region disclosed herein. In one embodiment, the isolated nucleic acid sequence encodes the light chain variable region comprising the amino acid sequence shown in FIG. 2 (SEQ ID NO:16). In another embodiment, isolated nucleic acid sequence encodes the heavy chain variable region comprising the amino acid sequence shown in FIG. 1 (SEQ ID NO:14). In a further embodiment, the nucleic acid sequence encoding the light chain variable region comprises the nucleic acid sequence shown in FIG. 2 (SEQ ID NO: 15). In an additional embodiment, the nucleic acid sequence encoding the heavy chain variable region comprises the nucleic acid sequence shown in FIG. 1 (SEQ ID NO:13).

The application also discloses variants of the nucleic acid sequences that encode for the light chain variable region and heavy chain variable region disclosed herein. For example, the variants include nucleotide sequences that hybridize to the nucleic acid sequences encoding the light chain variable region and heavy chain variable region disclosed herein under at least moderately stringent hybridization conditions. In another embodiment, the variant nucleic acid sequences have at least 50%, preferably at least 70%, most preferably at least 80%, even more preferably at least 90% and even most preferably at least 95% sequence identity to SEQ ID NO:13 or 15.

The application also discloses isolated nucleic acid sequences encoding the light chain CDR1 comprising the amino acid sequence SGNKLGDKYAC (SEQ ID NO:7); the light chain CDR2 comprising the amino acid sequence QDSKRPS (SEQ ID NO:8); the light chain CDR3 comprising the amino acid sequence QAWDNSTAV (SEQ ID NO:9); the heavy chain CDR1 comprising the amino acid sequence SYAMS (SEQ ID NO:10); the heavy chain CDR2 comprising the amino acid sequence TISGRGVTTYYADSVKG (SEQ ID NO:11); and the heavy chain CDR3 comprising the amino acid sequence DRTRYYGMDV (SEQ ID NO:12).

The application also provides isolated nucleic acid sequences encoding variants of the CDR sequences and variable region sequences discussed above.

Variant nucleic acid sequences include nucleic acid sequences that hybridize to the nucleic acid sequences encoding the amino acid sequences shown in SEQ ID NOS: 7-12, 14 and 16 and variants thereof under at least moderately stringent hybridization conditions, or have at least 50%, 60%, 70%, 80% or 90% sequence identity to the nucleic acid sequences that encode the amino acid sequence shown in SEQ ID NOS:7-12, 14 and 16.

(ii) Binding Proteins

Another aspect of the present application is a binding protein, preferably an antibody or antibody fragment, that comprises at least one light chain complementarity determining region disclosed herein (i.e. one or more of SEQ ID NOS:7-9) and/or at least one heavy chain complementarity determining region disclosed herein (i.e. one or more of SEQ ID NO:10-12).

In one embodiment, the binding protein comprises the light chain complementarity determining regions 1, 2 and 3 comprising the amino acid sequences SGNKLGDKYAC (SEQ ID NO:7); QDSKRPS (SEQ ID NO:8); and QAWDNSTAV (SEQ ID NO:9), respectively; and heavy chain complementarity determining regions 1, 2 and 3 comprising the amino acid sequences SYAMS (SEQ ID NO:10); TISGRGVTTYYADSVKG (SEQ ID NO:11); and DRTRYYGMDV (SEQ ID NO:12), respectively. The application also discloses a binding protein, preferably an antibody or antibody fragment, that comprises the light chain variable region shown in FIG. 2 (SEQ ID NO:16) and/or the heavy chain variable region shown in FIG. 1 (SEQ ID NO:14).

A person skilled in the art will appreciate that the application includes variants to the specific binding proteins disclosed above, including chemical equivalents to the sequences disclosed above that perform substantially the same function as the binding proteins disclosed above in substantially the same way. A functional variant of a binding protein will be able to bind to the same antigens or epitopes as the binding proteins disclosed above. In one embodiment, the variant binding protein binds to prostate stem cell antigen (SEQ ID NO:17). In another embodiment, the variant binding protein binds to a variant HnRNPG. In another embodiment, the variant binding protein binds to a variant HnRNPG having the amino acid sequence of SEQ ID NO:71. In another embodiment, the variant binding protein binds to a variant HnRNPG having the amino acid sequence of HnRNPG (SEQ ID NO:113) with one or more amino acid substitutions at positions 216, 218, 219 and/or 222. In a further embodiment the variant binding protein binds to a variant HnRNPG having the amino acid sequence of HnRNPG (SEQ ID NO:113) with substitutions at positions 214 to 224 with the amino acid sequence of SEQ ID NO:111 or 112. In another embodiment, the variant binding protein binds to an epitope having the amino acid sequence of SEQ ID NO:23, SEQ ID NO:41, SEQ ID NO: 111 or SEQ ID NO: 112

The inventors have identified the antigens to which the binding proteins disclosed herein bind. Accordingly, the application discloses proteins that bind to prostate stem cell antigen (SEQ ID NO:17), or variant HnRNPG. In one embodiment the variant HnRNPG has the amino acid sequence of SEQ ID NO:71. The inventors also identified the epitopes on the antigens to which the binding protein disclosed herein binds. Accordingly, the application provides binding proteins that bind to an epitope having the amino acid sequence of SEQ ID NO:23, SEQ ID NO:41, SEQ ID NO: 111 or SEQ ID NO: 112

In certain embodiments, the antibody or antibody fragment comprises all or a portion of a heavy chain constant region, such as an IgG1, IgG2, IgG3, IgG4, IgA1, IgA2, IgE, IgM or IgD constant region. Preferably, the heavy chain constant region is an IgG1 heavy chain constant region. Furthermore, the antibody or antibody fragment can comprise all or a portion of a kappa light chain constant region or a lambda light chain constant region. Preferably, the light chain constant region is a lambda light chain constant region.

To produce human monoclonal antibodies, antibody producing cells (lymphocytes) can be harvested from a human having cancer and fused with myeloma cells by standard somatic cell fusion procedures thus immortalizing these cells and yielding hybridoma cells. Such techniques are well known in the art, (e.g. the hybridoma technique originally developed by Kohler and Milstein (*Nature* 256:495-497 (1975)) as well as other techniques such as the human B-cell hybridoma technique (Kozbor et al., *Immunol. Today* 4:72 (1983)), the EBV-hybridoma technique to produce human monoclonal antibodies (Roder et al., *Methods Enzymol,* 121: 140-67 (1986)), and screening of combinatorial antibody libraries (Huse et al., *Science* 246:1275 (1989)). Hybridoma cells can be screened immunochemically for production of antibodies specifically reactive with cancer cells and the monoclonal antibodies can be isolated.

Specific antibodies, or antibody fragments, reactive against particular antigens or molecules, such as antigens or molecules on or in a cancer cell, may also be generated by screening expression libraries encoding immunoglobulin genes, or portions thereof, expressed in bacteria with cell surface components. For example, complete Fab fragments, VH regions and FV regions can be expressed in bacteria using phage expression libraries (See for example Ward et al., *Nature* 341:544-546 (1989); Huse et al., *Science* 246:1275-1281 (1989); and McCafferty et al., *Nature* 348:552-554 (1990)).

The present application includes all antibodies and antibody fragments that bind to the same antigen or epitope as the antibodies or antibody fragments disclosed herein. A person skilled in the art will appreciate that binding assays can be used to find other antibodies and antibody fragments with the same binding specificities as the antibodies and antibody fragments disclosed herein. As exemplified, below, a competition binding assay can be used to find such other antibodies.

Before a competition assay is performed using flow cytometry, the minimal concentration of antibody disclosed herein (Ab1) that gives maximal binding against a fixed number of cancer cells is determined. A total of $10^6$ cells are harvested from exponentially growing cultures and incubated with various antibody concentrations for 1 hr at 4° C. The cells are washed and incubated with a suitable detection antibody for an additional hour at 4° C. After washing, the cells are analyzed by flow cytometry. For each test antibody, a saturation curve is generated from the data by plotting median fluorescence against the antibody concentration.

For the competition assay, cancer cells are prepared as above and treated in duplicate with a fixed concentration of antibody (Ab1). The fixed concentration is the minimal concentration of antibody that generates maximal binding against a fixed number of cancer cells as determined above. Immediately following the addition of the Ab1, varying concentrations of the potential inhibitory antibody (Ab2) is added to each tube and the mixture incubated for 1 hr at 4° C. Both the percent inhibition and change over maximum median fluorescence are calculated by subtracting the background fluorescence (PBS-5% FCS) from the median fluorescence reading for each test sample (Ab1+Ab2). The result is then divided by the median fluorescence of Ab1 alone (maximal binding) minus the background (see below). The percent of inhibition result is obtained by multiplying by 100. The mean of the replicates along with their respective standard error is plotted against antibody concentration. The following formula is used to calculate the percent inhibition:

$$PI=[(MF_{(Ab1+Ab2)}-MF_{Bgd})/(MF_{Ab1}-MF_{Bgd})]\times 100$$

where PI=percent inhibition; $MF_{(Ab1+Ab2)}$=median fluorescence measured for Ab1+Ab2 mixture; and $MF_{Bgd}$=background median fluorescence with PBS-5% FCS.

Accordingly, the application provides a binding protein capable of binding an antigen on a cancer cell wherein the binding protein can be identified by a method comprising:

(1) incubating a fixed number of cancer cells with a minimal concentration of a binding protein disclosed herein, preferably an antibody or antibody fragment (Ab1) that generates maximal binding against the fixed number of cancer cells and measuring median fluorescence of Ab1 ($MF_{Ab1}$);

(2) testing two or more concentrations of a test binding protein (Ab2) by adding Ab2 to the Ab1 and cancer cells, and measuring median fluorescence ($MF_{(Ab1+Ab2)}$);

(3) measuring background median fluorescence ($MF_{bgd}$);

(4) calculating PI, wherein $$PI=[(MF_{(Ab1+Ab2)}-MF_{Bgd})/(MF_{Ab1}-MF_{Bgd})]\times 100;$$
and (5) comparing the PI to a control PI value;

wherein, a PI that has a statistically significant difference from the control PI indicates that the test binding protein is capable of binding the antigen or epitope on the cancer cell.

A person skilled in the art will appreciate that other competition assays can be used, including competition assays that use an antigen or epitope disclosed herein. For example, the antigen or epitope can be immobilized on a substrate, then the test binding protein can be allowed to bind to the immobilized antigen or epitope. Binding of the binding protein disclosed herein to the immobilized antigen or epitope can then be measured to determine if the test binding protein is able to compete against or block binding of the binding protein to the antigen or epitope. Example 9 of the present application is another example of a competition assay.

One embodiment is a binding protein capable of binding an antigen on or in a cancer cell wherein the binding protein can be identified by a competition binding assay comprising:

(1) a binding protein disclosed herein, preferably an antibody or antibody fragment (Ab1); and (2) an antigen or epitope disclosed herein, preferably a polypeptide comprising the amino acid sequence of SEQ ID NO: 17, 71, 23, 41, 111 or 112;

wherein one or more concentrations of a test binding protein is tested for its ability to compete with Ab1 for binding to the antigen or epitope.

A person skilled in the art will appreciate that affinity maturation techniques could be used modify the binding proteins or immunoconjugates disclosed herein by increasing its affinity for its antigens or epitopes.

Two strategies are routinely used to enhance the binding affinity of an antibody. One approach utilizes the resolution of the crystal structure of the Ab-Ag complex to identify the key residues involved in the antigen binding (Davies D. R., Cohen G. H. 1996. Interactions of protein antigens with antibodies. Proc Natl. Acad. Sci. U.S.A. 93, 7-12). Subsequently, those residues can be mutated to enhance the interaction. The other approach mimics an in vivo antigen stimulation that drives the affinity maturation of immunoglobulin produced by B cells. During the maturation of the immune response, the variable regions of the immunoglobulins are subjected to somatic mutations (Mc Heyzer-Williams M. 2003. B-cell signaling mechanism and activation. Fundamental Immunology, Fifth edition, 195-225). This process, highly specific for the immune system, is characterized by the introduction of point mutations at a very high rate. It occurs only within the DNA fragments encoding the variable regions and excludes the conserved domains. The B cells expressing the somatically mutated variant antibody are then subjected to an antigen-mediated selection resulting in the selection of higher affinity immunoglobulin. In order to replicate this phenomenon in vitro, several approaches have been used to introduce mutations either by random or targeted processes. The random mutations can be introduced using error-prone PCR, chain shuffling or mutator *E. coli* strains (Clackson T. Hoogenboom N. R., Griffiths A. D. and Winter G. 1991 Making antibody fragments using phage display libraries. Nature 352, 624-628, Hawkins R. E., Russell S. J. and Winter G. 1992. Selection of phage antibodies by binding affinity. Mimicking affinity maturation. J. Mol. Biol. 226, 889-896, Low N., Holliger P. and Winter G. 1996. Mimicking somatic hypermutation: affinity maturation of antibodies displayed on bacteriophage using a bacterial mutator strain. J. Mol. Biol. 260, 359-368). This strategy leads to the creation of large libraries in which reactive clones are selected with a display technology such as ribosome, phage or yeast (Min L. (2000). Applications of display technology in protein analysis. Nat. Biotechnol. 18, 1251-1256).

The targeted mutations of the CDRs, especially CDR3 of the light and heavy chains, have been shown to be an effective technique for increasing antibody affinity. Blocks of 3 to 4 amino acids of the CDR3 or specific regions called "hot-spots" are targeted for mutagenesis. Yang et al reported an increase of 420 fold of an anti-HIV gp120 Fab fragment by mutating four CDR residues (Yang W. P., Green K., Pinz-Sweeney S., Briones A. T., Burton D. R. and Barbas C. F. III. 1995. CDR walking mutagenesis for the affinity maturation of a potent human anti-HIV-1 antibody into picomolar range. J. Mol. Biol., 254, 392-403). One mutation in the VL CDR3 combined with three mutations in the VH CDR3 of the C6.5 scFv yielded a 1230 fold increased affinity (Schier R., McCall A., Adams G. P., Marshall K. W., Merrit H., Yin M., Crawford R. S. Weiner L. M., Marks C. and Marks J. D. 1996. Isolation of picomolar affinity anti-c-erbB-2 single-chain Fv by molecular evolution of the complementary determining regions in the center of the antibody binding site. J. Mol. Biol., 263, 551-567).

"Hot spots" are the sequences where somatic hypermutation takes place in vivo (Neuberger M. S and Milstein C. 1995. Somatic hypermutation. Curr. Opin. Immunol. 7, 248-254). The hotspot sequences can be defined as consensus nucleotide sequences in certain codons. The consensus sequence is the tetranucleotide, RGYW, in which R can be either A or G, Y can be C or T and W can be either A or T (Neuberger M. S and Milstein C. 1995. Somatic hypermutation. Curr. Opin. Immunol. 7, 248-254). In addition, the serine residues encoded by the nucleotides AGY are predominantly present in the CDRs regions of the variable domain over those encoded by TCN corresponding to a potential hot-spot sequences (Wagner S. D., Milstein C. and Neuberger M. S.

1995. Codon bias targets mutation. Nature, 376, 732). The structural analysis has shown that the CDR loops contribute the most to the antigen binding, especially the CDR3 loops (Giudicelli V., Chaume D. and Lefranc M. P. 2004. IMGT/V-QUEST, an integrated software program for immunoglobulin and T cell receptor V-J and V-D-J rearrangement analysis. Nucleic Acids Res. 32, 435-440). Therefore, the nucleotide sequence of the CDRs of the heavy and light chains of each antibody is scanned for the presence of the hot-spot sequences and AGY codons. The identified hot-spots of the CDR regions of the light and heavy chain are compared to the germinal sequences of the heavy and light chains using the International ImMunoGen Tics database (IMGT, http://imgt-.cines.fr/textes/vquest/) (Davies D. R., Padlan E. A. and Sheriff S. 1990. Antibody-antigen complexes. Annu. Rev. Biochem. 59, 439-473). A sequence, identical to the germ line, suggest that somatic mutation has not occurred; therefore the random mutations are introduced mimicking the somatic events occurring in vivo. In contrast, a different sequence shows that some somatic mutations have already occurred. It will remain to be determined if the in vivo somatic mutation was optimal. The hot-spots that code for buried or conserved amino acids within the CDRs are not mutagenized. These residues are usually critical for the overall structure and are unlikely to interact with the antigen since they are buried. In addition, the sequences can be compared to the predicted locations in the germ line sequences where somatic mutations occurred predominantly (Tomlinson I. M., Cox J. P. L., Gherardi E., Lesk A. M. and Chotia C. 1995. The structural repertoire of the human Vldomain. EMBO J. 14, 4628-4638, Tomlinson I. M., Walter G., Jones P. T., Dear P. H., Sonnhammer E. L. L. and Winter G. 1996. The imprint of somatic hypermutation on the repertoire of human germline V genes. J. Mol. Biol. 256, 813-817). A similar strategy was applied for the affinity maturation of BL22 scFv. A point mutation introduced in the CDR3 of the heavy resulted in 5 to 10 fold increase in binding activity on various CD22-positive cell lines (Salvatore G., Beers R., Margulies I., Kreitman R. J. and Pastan I. 2002. Improved cytotoxic activity toward cell lines and fresh leukemia cells of a mutant anti-CD22 immunotoxin obtained by antibody phage display. Clinical Cancer research, 8, 995-1002). Also, the mutation of various amino acids in the CDR1 and CDR2 loops also produced mutant with increase affinity ranging from 3 fold to 7 fold (Ho M., Kreitman J., Onda M. and Pastan I. 2005. In vitro antibody evolution targeting germline hot spots to increase activity of an anti-CD22 immunotoxin. J. Biol. Chem., 280, 607-617).

After mutations are introduced, either by random or targeted processes, the antibodies are expressed and assessed for function. For instance, functional screening can be based on binding. Once function is assessed, then DNA sequencing of the chosen antibodies can be carried out using known methods.

In another embodiment, the anchored periplasmic expression (APEx) method described by Harvey, B et al (PNAS 2004 Jun. 22; 101(25): 9193-8) is used for affinity maturation of the binding proteins or immunoconjugates disclosed herein.

Accordingly, the application includes binding proteins disclosed herein that have been affinity maturized to increase the affinity of the binding protein to prostate stem cell antigen (SEQ ID NO:17), variant HnRNPG or the variant HnRNPG having the amino acid sequence of SEQ ID NO:71, or an epitope having the amino acid sequence of SEQ ID NO:23, SEQ ID NO:41, SEQ ID NO:111 or SEQ ID NO:112.

The application also provides compositions comprising the binding proteins disclosed, preferably antibodies and antibody fragments, with a pharmaceutically acceptable excipient, carrier, buffer or stabilizer.

Further, the application provides isolated nucleic acid sequences encoding the binding proteins disclosed herein. The application also includes variants to these nucleic acid sequences. For example, the variants include nucleic acid sequences that hybridize to the nucleic acid sequences encoding the binding proteins disclosed herein under at least moderately stringent hybridization conditions, or have at least 50%, 60%, 70%, 80%, 90% or 95% sequence identity to the nucleic acid sequences that encode the binding proteins disclosed herein.

(C) Cancer-Associated Antigen

The inventors have identified the antigens to which the binding proteins disclosed herein bind (namely, prostate stem cell antigen (SEQ ID NO:17) and variant HnRNPG). Prostate stem cell antigen is expressed on the surface of cancer cells and is not significantly expressed on the surface of normal cells. Variant HnRNPG is an intracellular protein expressed in cancer cells Accordingly, the application includes an isolated polypeptide that can specifically bind with one of the binding proteins disclosed herein, and nucleic acid sequences and uses thereof.

The present application includes a novel cancer-associated antigen, namely a cancer-associated variant of HnRNPG.

In addition, the inventors identified the epitopes to which the binding proteins disclosed herein bind (namely, SEQ ID NOS: 23, 41, 111 and 112). Accordingly, the application includes an isolated polypeptide comprising the amino acid sequence of SEQ ID NO:23, an isolated polypeptide comprising the amino acid sequence of SEQ ID NO:41 an isolated polypeptide comprising the amino acid sequence of SEQ ID NO:111 and an isolated polypeptide comprising the amino acid sequence of SEQ ID NO 112. Another embodiment includes an isolated polypeptide consisting of the amino acid sequence of SEQ ID NO:23, an isolated polypeptide consisting of the amino acid sequence of SEQ ID NO:41, an isolated polypeptide consisting of the amino acid sequence of SEQ ID NO:111 and an isolated polypeptide consisting of the amino acid sequence of SEQ ID NO:112

A person skilled in the art will appreciate that the application includes variants to the amino acid sequences of SEQ ID NOS:23, 41, 111 and 112 including chemical equivalents. Such equivalents include proteins that perform substantially the same function as the specific proteins disclosed herein in substantially the same way. For example, equivalents include, without limitation, conservative amino acid substitutions.

In one embodiment, the variant amino acid sequences of the isolated polypeptides disclosed herein have at least 50%, preferably at least 60%, more preferably at least 70%, most preferably at least 80%, even more preferably at least 90%, and even most preferably at least 95% sequence identity to SEQ ID NOS:23, 41, 111 or 112.

The application includes the use of these isolated polypeptides. For example, the use of the polypeptides to generate binding proteins and immunoconjugates that can be used to treat or prevent cancer or that can be used to detect or monitor cancer in a subject or in the manufacture of a medicament to treat or prevent cancer.

Further, the application provides isolated nucleic acid sequences that encode the polypeptides disclosed herein. The application also includes variants to these nucleic acid sequences. For example, the variants include nucleotide sequences that hybridize to the nucleic acid sequences that encode the polypeptides disclosed herein under at least moderately stringent hybridization conditions, or that have at least 50%, 60%, 70%, 80%, 90% or 95% sequence identity to the nucleic acid sequences that encode the polypeptides disclosed herein.

(D) Immunoconjugates

The application also includes an immunoconjugate comprising (1) a binding protein disclosed herein, preferably an antibody or antibody fragment, that has been attached to (2) an effector molecule. In one embodiment, the binding protein binds to an antigen or molecule on or in a cancer cell. In one embodiment, the antigen or molecule comprises prostate stem cell antigen or variant HnRNPG. In another embodiment, the antigen or molecule comprises the amino acid sequence of SEQ ID NO:23, SEQ ID NO: 41, SEQ ID NO: 111 or SEQ ID NO: 112.

In a preferred, embodiment the effector molecule is (i) a label, which can generate a detectable signal, directly or indirect, or (ii) a cancer therapeutic agent, which is either cytotoxic, cytostatic or otherwise prevents or reduces the ability of the cancer cells to divide and/or metastasize.

In an embodiment, the effector molecule is a cancer therapeutic agent. The cancer therapeutic agent is preferably a toxin that is either cytotoxic, cytostatic or otherwise prevents or reduces the ability of the cancer cells to divide and/or metastasize. Accordingly, one aspect of the application is an immunoconjugate comprising (1) a binding protein disclosed herein, preferably an antibody or antibody fragment, attached to (2) a cancer therapeutic agent, such as a cytotoxin.

In another embodiment, the immunoconjugate is internalized and the cancer therapeutic agent is a cytotoxin that blocks the protein synthesis of the cell, therein leading to cell death. Importantly, since most normal cells do not widely express the antigen present on the cancer cells, they cannot bind and internalize the immunoconjugate, and are protected from the killing effect of the toxin or other cancer therapeutic agents.

A variety of effector molecules may be used and a number of such effector molecules are intracellularly active molecules. Accordingly, in an embodiment, the immunoconjugate is internalized by the cancer cell.

In preferred embodiments, the effector molecule is a cancer therapeutic agent, more preferably a cytotoxin that comprises a polypeptide having ribosome-inactivating activity including, without limitation, gelonin, bouganin, saporin, ricin, ricin A chain, bryodin, diphtheria toxin, restrictocin, *Pseudomonas* exotoxin A and variants thereof. When the protein is a ribosome-inactivating protein, the immunoconjugate must be internalized upon binding to the cancer cell in order for the protein to be cytotoxic to the cells. Accordingly, in an embodiment, the effector molecule is a cytotoxin and the immunoconjugate is internalized by the cancer cell.

In one embodiment, the toxin is bouganin or *Pseudomonas* exotoxin A, and variants thereof. In another embodiment, the toxin is modified bouganin or a truncated form of *Pseudomonas* exotoxin A that lacks the cell binding domain. In a further embodiment, the toxin is a bouganin substantially devoid of T-cell epitopes or a truncated form of *Pseudomonas* exotoxin A that consists of amino acids 252-608.

In other nonlimiting embodiments, the cancer therapeutic agent comprises an agent that acts to disrupt DNA. Thus, the cancer therapeutic agents may be selected, without limitation, from enediynes (e.g., calicheamicin and esperamicin) and non-enediyne small molecule agents (e.g., bleomycin, methidiumpropyl-EDTA-Fe(II)). Other cancer therapeutic agents include, without limitation, daunorubicin, doxorubicin, distamycin A, cisplatin, mitomycin C, ecteinascidins, duocarmycin/CC-1065, and bleomycin/pepleomycin.

In other nonlimiting embodiments, the cancer therapeutic agent comprises an agent that acts to disrupt tubulin. Such agents may comprise, without limitation, rhizoxin/maytansine, paclitaxel, vincristine and vinblastine, colchicine, auristatin dolastatin 10 MMAE, and peloruside A.

In other nonlimiting embodiments, the cancer therapeutic portion of an immunoconjugate may comprise an alkylating agent including, without limitation, Asaley NSC 167780, AZQ NSC 182986, BCNU NSC 409962, Busulfan NSC 750, carboxyphthalatoplatinum NSC 271674, CBDCA NSC 241240, CCNU NSC 79037, CHIP NSC 256927, chlorambucil NSC 3088, chlorozotocin NSC 178248, cis-platinum NSC 119875, clomesone NSC 338947, cyanomorpholinodoxorubicin NSC 357704, cyclodisone NSC 348948, dianhydrogalactitol NSC 132313, fluorodopan NSC 73754, hepsulfam NSC 329680, hycanthone NSC 142982, melphalan NSC 8806, methyl CCNU NSC 95441, mitomycin C NSC 26980, mitozolamide NSC 353451, nitrogen mustard NSC 762, PCNU NSC 95466, piperazine NSC 344007, piperazinedione NSC 135758, pipobroman NSC 25154, porfiromycin NSC 56410, spirohydantoin mustard NSC 172112, teroxirone NSC 296934, tetraplatin NSC 363812, thio-tepa NSC 6396, triethylenemelamine NSC 9706, uracil nitrogen mustard NSC 34462, and Yoshi-864 NSC 102627.

In other nonlimiting embodiments, the cancer therapeutic agent portion of the immunoconjugate may comprise an antimitotic agent including, without limitation, allocolchicine NSC 406042, Halichondrin B NSC 609395, colchicine NSC 757, colchicine derivative NSC 33410, dolastatin 10 NSC 376128 (NG-auristatin derived), maytansine NSC 153858, rhizoxin NSC 332598, taxol NSC 125973, taxol derivative NSC 608832, thiocolchicine NSC 361792, trityl cysteine NSC 83265, vinblastine sulfate NSC 49842, and vincristine sulfate NSC 67574.

In other nonlimiting embodiments, the cancer therapeutic agent portion of the immunoconjugate may comprise an topoisomerase I inhibitor including, without limitation, camptothecin NSC 94600, camptothecin, Na salt NSC 100880, aminocamptothecin NSC 603071, camptothecin derivative NSC 95382, camptothecin derivative NSC 107124, camptothecin derivative NSC 643833, camptothecin derivative NSC 629971, camptothecin derivative NSC 295500, camptothecin derivative NSC 249910, camptothecin derivative NSC 606985, camptothecin derivative NSC 374028, camptothecin derivative NSC 176323, camptothecin derivative NSC 295501, camptothecin derivative NSC 606172, camptothecin derivative NSC 606173, camptothecin derivative NSC 610458, camptothecin derivative NSC 618939, camptothecin derivative NSC 610457, camptothecin derivative NSC 610459, camptothecin derivative NSC 606499, camptothecin derivative NSC 610456, camptothecin derivative NSC 364830, camptothecin derivative NSC 606497, and morpholinodoxorubicin NSC 354646.

In other nonlimiting embodiments, cancer therapeutic agent portion of the immunoconjugate may comprise an topoisomerase II inhibitor including, without limitation, doxorubicin NSC 123127, amonafide NSC 308847, m-AMSA NSC 249992, anthrapyrazole derivative NSC 355644, pyrazoloacridine NSC 366140, bisantrene HCL NSC 337766, daunorubicin NSC 82151, deoxydoxorubicin NSC 267469, mitoxantrone NSC 301739, menogaril NSC 269148, N,N-dibenzyl daunomycin NSC 268242, oxanthrazole NSC 349174, rubidazone NSC 164011, VM-26 NSC 122819, and VP-16 NSC 141540.

In other nonlimiting embodiments, the cancer therapeutic agent portion of the immunoconjugate may comprise an RNA or DNA antimetabolite including, without limitation, L-alanosine NSC 153353, 5-azacytidine NSC 102816, 5-fluorouracil NSC 19893, acivicin NSC 163501, aminopterin derivative NSC 132483, aminopterin derivative NSC 184692, aminopterin derivative NSC 134033, an antifol NSC 633713, an antifol NSC 623017, Baker's soluble antifol NSC 139105, dichlorallyl lawsone NSC 126771, brequinar NSC 368390, ftorafur (pro-drug) NSC 148958, 5,6-dihydro-5-azacytidine NSC 264880, methotrexate NSC 740, methotrexate derivative NSC 174121, N-(phosphonoacetyl)-L-aspartate (PALA) NSC 224131, pyrazofurin NSC 143095, trimetrexate NSC 352122, 3-HP NSC 95678, 2'-deoxy-5-fluorouridine NSC 27640, 5-HP NSC 107392, alpha-TGDR NSC 71851, aphidicolin glycinate NSC 303812, ara-C NSC 63878, 5-aza-2'-deoxycytidine NSC 127716, beta-TGDR NSC 71261, cyclocytidine NSC 145668, guanazole NSC 1895, hydroxyurea NSC 32065, inosine glycodialdehyde NSC 118994, macbecin II NSC 330500, pyrazoloimidazole NSC 51143, thioguanine NSC 752, and thiopurine NSC 755.

In another nonlimiting embodiment, the therapeutic portion of the immunoconjugates may be a nucleic acid. Nucleic acids that may be used include, but are not limited to, antisense RNA, genes or other polynucleotides, nucleic acid analogs such as thioguanine and thiopurine.

The present application further provides immunoconjugates comprising (i) a binding protein disclosed herein, preferably an antibody or antibody fragment, attached to (2) an effector molecule, wherein the effector molecule is a label, which can generate a detectable signal, indirectly or directly. These immunoconjugates can be used for research or diagnostic applications, including the in vivo detection of cancer. The label is preferably capable of producing, either directly or indirectly, a detectable signal. For example, the label may be radio-opaque or a radioisotope, such as $^{3}H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

In another embodiment, the immunoconjugate is detectable indirectly. For example, a secondary antibody that is specific for the immunoconjugate and contains a detectable label can be used to detect the immunoconjugate.

The binding protein disclosed herein, preferably an antibody or antibody fragment, may be "attached to" the effector molecule by any means by which the binding protein can be associated with, or linked to, the effector molecule. For example, the binding protein may be attached to the effector molecule by chemical or recombinant means. Chemical means for preparing fusions or conjugates are known in the art and can be used to prepare the immunoconjugate. The method used to conjugate the binding protein and effector molecule must be capable of joining the binding protein with the effector molecule without interfering with the ability of the binding protein to bind to the antigen on or in the cancer cell.

The binding protein may be linked indirectly to the effector molecule. For example, the binding protein may be directly linked to a liposome containing the effector molecule of one of several types. The effector molecule(s) and/or binding protein may also be bound to a solid surface.

In one embodiment, the binding protein, preferably an antibody or antibody fragment, and effector molecule are both proteins and can be conjugated using techniques well known in the art. There are several hundred crosslinkers available that can conjugate two proteins. (See for example "Chemistry of Protein Conjugation and Crosslinking". 1991, Shans Wong, CRC Press, Ann Arbor). The crosslinker is generally chosen based on the reactive functional groups available or inserted on the binding protein, preferably an antibody or antibody fragment, and/or effector molecule. In addition, if there are no reactive groups, a photoactivatible crosslinker can be used. In certain instances, it may be desirable to include a spacer between the binding protein, preferably an antibody or antibody fragment, and effector molecule. Crosslinking agents known to the art include the homobifunctional agents: glutaraldehyde, dimethyladipimidate and Bis(diazobenzidine) and the heterobifunctional agents: m-Maleimidobenzoyl-N-Hydroxysuccinimide and Sulfo-m-Maleimidobenzoyl-N-Hydroxysuccinimide.

In certain instances, the binding protein may be engineered with specific residues for chemical attachment of the effector molecule. Specific residues used for chemical attachment of molecule known to the art include lysine and cysteine. The crosslinker is chosen based on the reactive functional groups inserted on the binding protein, and available on the effector molecule.

A binding protein-effector molecule protein fusion may also be prepared using recombinant DNA techniques. In such a case a DNA sequence encoding the binding protein is fused to a DNA sequence encoding the effector molecule, resulting in a chimeric DNA molecule. The chimeric DNA sequence is transfected into a host cell that expresses the fusion protein. The fusion protein can be recovered from the cell culture and purified using techniques known in the art.

Examples of attaching an effector molecule, which is a label, to the binding protein include the methods described in Hunter, et al., Nature 144:945 (1962); David, et al., Biochemistry 13:1014 (1974); Pain, et al., J. Immunol. Meth. 40:219 (1981); Nygren, J. Histochem. and Cytochem. 30:407 (1982); Wensel and Meares, Radioimmunoimaging And Radioimmunotherapy, Elsevier, N.Y. (1983); and Colcher et al., "Use Of Monoclonal Antibodies As Radiopharmaceuticals For The Localization Of Human Carcinoma Xenografts In Athymic Mice", Meth. Enzymol., 121:802-16 (1986).

In one embodiment, the immunoconjugate comprises the amino acid sequence defined by SEQ ID NO:49. In another embodiment, the immunoconjugate comprises the amino acid sequence defined by SEQ ID NO:51. The application also includes variants to these sequences.

The application also provides for isolated nucleic acid sequences that encode the immunoconjugates disclosed herein. In one embodiment, the isolated nucleic acid sequence encodes a polypeptide comprising the amino acid sequence of SEQ ID NO: 49. In another embodiment, the isolated nucleic acid sequence comprises SEQ ID NO:48. In a further embodiment, the isolated nucleic acid sequence encodes a polypeptide comprising the amino acid sequence of SEQ ID NO:51. In another embodiment, the isolated nucleic acid sequence comprises SEQ ID NO:50.

The application also includes variants to these nucleic acid sequences. For example, the variants include nucleic acid sequences that hybridize to the nucleic acid sequences encoding the immunoconjugates disclosed herein under at least moderately stringent hybridization conditions, or that have at least 50%, 60%, 70%, 80%, 90% or 95% sequence identity to the nucleic acid sequences that encode the immunoconjugate disclosed herein.

(E) Preparation of Proteins

A person skilled in the art will appreciate that the polypeptides disclosed herein, such as the light and heavy complementarity determining regions, the light and heavy chain variable regions, antibodies and antibody fragments, immunoconjugates, cancer-associated antigens and epitopes disclosed herein, may be prepared in any of several ways, but is most preferably prepared using recombinant methods.

Accordingly, the nucleic acid molecules disclosed herein may be incorporated in a known manner into an appropriate expression vector which ensures good expression of the polypeptides. Possible expression vectors include but are not limited to cosmids, plasmids, or modified viruses (e.g. replication defective retroviruses, adenoviruses and adeno-associated viruses), so long as the vector is compatible with the host cell used. The expression vectors are “suitable for transformation of a host cell”, which means that the expression vectors contain a nucleic acid molecule and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The application therefore includes a recombinant expression vector containing a nucleic acid molecule disclosed herein, or a fragment thereof, and the necessary regulatory sequences for the transcription and translation of the inserted protein-sequence.

Suitable regulatory sequences may be derived from a variety of sources, including bacterial, fungal, viral, mammalian, or insect genes (For example, see the regulatory sequences described in Goeddel, Gene Expression Technology Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors may also contain a selectable marker gene which facilitates the selection of host cells transformed or transfected with a recombinant molecule disclosed herein. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of the recombinant expression vectors disclosed herein and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The terms “transformed with”, “transfected with”, “transformation” and “transfection” are intended to encompass introduction of nucleic acid (e.g. a vector) into a cell by one of many possible techniques known in the art. The term “transformed host cell” as used herein is intended to also include cells capable of glycosylation that have been transformed with a recombinant expression vector disclosed herein. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 3rd Edition, Cold Spring Harbor Laboratory Press, 2001), and other laboratory textbooks.

Suitable host cells include a wide variety of eukaryotic host cells and prokaryotic cells. For example, polypeptides disclosed herein may be expressed in yeast cells or mammalian cells. Other suitable host cells can be found in Goeddel, Gene Expression Technology: Methods in Enzymology 185, Academic Press, San Diego, Calif. (1990). In addition, the polypeptides disclosed herein may be expressed in prokaryotic cells, such as *Escherichia coli* (Zhang et al., Science 303(5656): 371-3 (2004)). In addition, a *Pseudomonas* based expression system such as *Pseudomonas fluorescens* can be used (US Patent Application Publication No. US 2005/0186666, Schneider, Jane C et al.).

Yeast and fungi host cells suitable for carrying out the methods disclosed herein include, but are not limited to *Saccharomyces cerevisiae*, the genera *Pichia* or *Kluyveromyces* and various species of the genus *Aspergillus*. Examples of vectors for expression in yeast *S. cerevisiae* include pYepSec1 (Baldari. et al., Embo J. 6:229-234 (1987)), pMFa (Kurjan and Herskowitz, *Cell* 30:933-943 (1982)), pJRY88 (Schultz et al., Gene 54:113-123 (1987)), and pYES2 (Invitrogen Corporation, San Diego, Calif.). Protocols for the transformation of yeast and fungi are well known to those of ordinary skill in the art (see Hinnen et al., Proc. Natl. Acad. Sci. USA 75:1929 (1978); Ito et al., J. Bacteriology 153:163 (1983), and Cullen et al. (Nat BiolTech 5:369 (1987)).

Suitable mammalian cells include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329: 840 (1987)) and pMT2PC (Kaufman et al., EMBO J. 6:187-195 (1987)).

Given the teachings provided herein, promoters, terminators, and methods for introducing expression vectors of an appropriate type into plant, avian, and insect cells may also be readily accomplished. For example, within one embodiment, the polypeptides disclosed herein may be expressed from plant cells (see Sinkar et al., J. Biosci (Bangalore) 11:47-58 (1987), which reviews the use of *Agrobacterium rhizogenes* vectors; see also Zambryski et al., Genetic Engineering, Principles and Methods, Hollaender and Setlow (eds.), Vol. VI, pp. 253-278, Plenum Press, New York (1984), which describes the use of expression vectors for plant cells, including, among others, PAPS2022, PAPS2023, and PAPS2034).

Suitable insect cells include cells and cell lines from *Bombyx, Trichoplusia* or *Spodotera* species. Baculovirus vectors available for expression of proteins in cultured insect cells (SF 9 cells) include the pAc series (Smith et al., Mol. Cell. Biol. 3:2156-2165 (1983)) and the pVL series (Luckow, V. A., and Summers, M. D., Virology 170:31-39 (1989

Alternatively, the polypeptides disclosed herein may also be expressed in non-human transgenic animals such as rats, rabbits, sheep and pigs (Hammer et al. Nature 315:680-683 (1985); Palmiter et al. Science 222:809-814 (1983); Brinster et al. Proc. Natl. Acad. Sci. USA 82:4438-4442 (1985); Palmiter and Brinster Cell 41:343-345 (1985) and U.S. Pat. No. 4,736,866).

The polypeptides disclosed herein may also be prepared by chemical synthesis using techniques well known in the chemistry of proteins such as solid phase synthesis (Merrifield, J. Am. Chem. Assoc. 85:2149-2154 (1964); Frische et al., J. Pept. Sci. 2(4): 212-22 (1996)) or synthesis in homogenous solution (Houbenweyl, Methods of Organic Chemistry, ed. E. Wansch, Vol. 15 I and II, Thieme, Stuttgart (1987)).

N-terminal or C-terminal fusion proteins comprising the polypeptides disclosed herein conjugated with other molecules, such as proteins may be prepared by fusing, through recombinant techniques. The resultant fusion proteins contain polypeptides disclosed herein fused to the selected protein or marker protein as described herein. The recombinant polypeptides disclosed herein may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate. Examples of proteins which may be used to prepare fusion proteins or conjugates include cell binding proteins such as immunoglobulins, hormones, growth factors, lectins, insulin, low density lipoprotein, glucagon, endorphins, transferrin, bombesin, asialoglycoprotein glutathione-S-transferase (GST), hemagglutinin (HA), and truncated myc.

Accordingly, the application provides a recombinant expression vector comprising the nucleic acid sequences that encode the polypeptides disclosed herein, such as the light and heavy chain complementarity determining regions, the light and heavy chain variable regions, the binding proteins, such as antibodies and antibody fragments, immunoconjugates, antigens and epitopes disclosed herein. Further, the application provides a host cell comprising the nucleic acid sequences or recombinant expression vectors disclosed herein.

(F) Therapeutic Methods and Pharmaceutical Compositions of the Binding Proteins and Immunotoxins The inventors have shown that the binding proteins disclosed herein show specificity for cancer cells. In addition, the inventors have shown that the binding proteins disclosed herein are internalized by cancer cells. Thus, the binding proteins disclosed herein can be used for the targeted delivery of bioactive or medically relevant agents, such as imaging, radioactive or cytotoxic agents.

One embodiment is a method of treating or preventing cancer, comprising administering to a subject having or suspected of having cancer an effective amount of the immunoconjugate disclosed herein. Another embodiment is the use of an effective amount of the immunoconjugate disclosed herein for the manufacture of a medicament for treating or preventing cancer. Furthermore, the application provides the use of an effective amount of the immunoconjugate disclosed herein, further comprising the use of an additional cancer therapeutic agent for the manufacture of a medicament for simultaneous, separate or sequential treatment or prevention of cancer. The application also provides the use of an effective amount of the immunoconjugate disclosed herein for treating or preventing cancer. Further, the application provides the use of an effective amount of the immunoconjugate disclosed herein, further comprising the use of an additional cancer therapeutic agent for simultaneous, separate or sequential treatment or prevention of cancer.

In one embodiment, cancer includes, without limitation, stomach cancer, colon cancer, prostate cancer as well as cervical cancer, uterine cancer, ovarian cancer, pancreatic cancer, kidney cancer, liver cancer, head and neck cancer, squamous cell carcinoma, gastrointestinal cancer, breast cancer (such as carcinoma, ductal, lobular, and nipple), lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer, neuroblastoma, sarcomas, rectum cancer, bladder cancer, pancreatic cancer, endometrial cancer, plasmacytoma, lymphoma, and melanoma. In another embodiment, the cancer is an epithelial cancer. In a further embodiment, the cancer is lung cancer, liver cancer, prostate cancer, skin cancer (including melanoma), ovarian, pancreatic cancer, and head and neck cancer or breast cancer. In an additional embodiment, the cancer is lung cancer, liver cancer, skin cancer (including melanoma) or prostate cancer.

The ability of the immunoconjugate disclosed herein to selectively inhibit or destroy cells having cancer may be readily tested in vitro using cancer cell lines. The selective inhibitory effect of the immunoconjugates disclosed herein may be determined, for example by demonstrating the selective inhibition of cellular proliferation of the cancer cells.

Toxicity may also be measured based on cell viability, for example, the viability of cancer and normal cell cultures exposed to the immunoconjugate may be compared. Cell viability may be assessed by known techniques, such as trypan blue exclusion assays.

In another example, a number of models may be used to test the effectiveness of the immunoconjugates disclosed herein. Thompson, E. W. et al. (Breast Cancer Res. Treatment 31:357-370 (1994)) has described a model for the determination of invasiveness of human breast cancer cells in vitro by measuring tumor cell-mediated proteolysis of extracellular matrix and tumor cell invasion of reconstituted basement membrane (collagen, laminin, fibronectin, Matrigel or gelatin). Other applicable cancer cell models include cultured ovarian adenocarcinoma cells (Young, T. N. et al. Gynecol. Oncol. 62:89-99 (1996); Moore, D. H. et al. Gynecol. Oncol. 65:78-82 (1997)), human follicular thyroid cancer cells (Demeure, M. J. et al., World J. Surg. 16:770-776 (1992)), human melanoma (A-2058) and fibrosarcoma (HT-1080) cell lines (Mackay, A. R. et al. Lab. Invest. 70:781 783 (1994)), and lung squamous (HS-24) and adenocarcinoma (SB-3) cell lines (Spiess, E. et al. J. Histochem. Cytochem. 42:917-929 (1994)). An in vivo test system involving the implantation of tumors and measurement of tumor growth and metastasis in athymic nude mice has also been described (Thompson, E. W. et al., Breast Cancer Res. Treatment 31:357-370 (1994); Shi, Y. E. et al., Cancer Res. 53:1409-1415 (1993)).

The immunoconjugates may be formulated into pharmaceutical compositions for administration to subjects in a biologically compatible form suitable for administration in vivo. The substances may be administered to living organisms including humans, and animals. Administration of a therapeutically active amount of the pharmaceutical compositions is defined as an amount effective, at dosages and for periods of time necessary to achieve the desired result. For example, a therapeutically active amount of a substance may vary according to factors such as the disease state, age, sex, and weight of the individual, and the ability of the recombinant protein to elicit a desired response in the individual. Dosage regime may be adjusted to provide the optimum therapeutic response. For example, several divided doses may be administered daily or the dose may be proportionally reduced as indicated by the exigencies of the therapeutic situation.

Accordingly, the present application provides a pharmaceutical composition for treating or preventing cancer comprising the immunoconjugates disclosed herein, and a pharmaceutically acceptable carrier, diluent or excipient. In a preferred embodiment, the effector molecule of the immunoconjugate in the pharmaceutical composition is a cancer therapeutic agent, more preferably a toxin.

The pharmaceutical preparation comprising the immunoconjugate may be administered systemically. The pharmaceutical preparation may be administered directly to the cancer site. Depending on the route of administration, the immunoconjugate may be coated in a material to protect the compound from the action of enzymes, acids and other natural conditions that may inactivate the compound.

In accordance with one aspect of the present application, the immunoconjugate is delivered to the patient by direct administration. The application contemplates the pharmaceutical composition being administered in at least an amount sufficient to achieve the endpoint, and if necessary, comprises a pharmaceutically acceptable carrier.

The application also provides methods for reducing the risk of post-surgical complications comprising administering an effective amount of the immunoconjugate before, during, or after surgery to treat cancer.

The compositions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, $20^{th}$ ed., Mack Publishing Company, Easton, Pa., USA, 2000). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. Immunoconjugate may be supplied, for example but not by way of limitation, as a lyophilized powder which is reconstituted with sterile water or saline prior to administration to the patient.

Pharmaceutical compositions may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N,N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In various embodiments, the pharmaceutical composition is directly administered systemically or directly to the area of the tumor(s).

The pharmaceutical compositions may be used in methods for treating animals, including mammals, preferably humans, with cancer. The dosage and type of immunoconjugate to be administered will depend on a variety of factors which may be readily monitored in human subjects. Such factors include the etiology and severity (grade and stage) of the cancer.

Clinical outcomes of cancer treatments using the immunoconjugates disclosed herein are readily discernable by one of skill in the relevant art, such as a physician. For example, standard medical tests to measure clinical markers of cancer may be strong indicators of the treatment's efficacy. Such tests may include, without limitation, physical examination, performance scales, disease markers, 12-lead ECG, tumor measurements, tissue biopsy, cytoscopy, cytology, longest diameter of tumor calculations, radiography, digital imaging of the tumor, vital signs, weight, recordation of adverse events, assessment of infectious episodes, assessment of concomitant medications, pain assessment, blood or serum chemistry, urinalysis, CT scan, and pharmacokinetic analysis. Furthermore, synergistic effects of a combination therapy comprising the immunoconjugate and another cancer therapeutic may be determined by comparative studies with patients undergoing monotherapy.

In the majority of approved cancer therapies, the cancer therapy is used in combination with other cancer therapies. Accordingly, the application provides a method of preventing or treating cancer using the immunoconjugate disclosed herein in combination with at least one additional cancer therapy. The other cancer therapy may be administered prior to, overlapping with, concurrently, and/or after administration of the immunoconjugate. When administered concurrently, the immunoconjugate and the other cancer therapeutic may be administered in a single formulation or in separate formulations, and if separately, then optionally, by different modes of administration. The combination of one or more immunoconjugates and one or more other cancer therapies may synergistically act to combat the tumor or cancer. The other cancer therapies include, without limitation, other cancer therapeutic agents including, without limitation, 2,2,2 trichlorotriethylamine, 3-HP, 5,6-dihydro-5-5-azacytidine, 5-aza-2'-deoxycytidine, 5-azacytidine, 5-fluorouracil, 5-HP, 5-propagermanium, 6-azauridine, 6-diazo-5-0x0-L-norleucine, 6-mercaptopurine, 6-thioguanine, abrin, aceglarone, acivicin, aclacinomycin, actinomycin, actinomycin D, aldesleukin, allocolchicine, allutamine, alpha-fetoprotein, alpha-TGDR, altretamine, aminocamptothecin, aminoglutethimide, aminopterin derivative, amonafide, amsacrine, an antifol, anastrozole, ancitabine, angiogenin antisense oligonucleotide, angiostatin, anthramycin, anthrapyrazole derivative, anti-thrombin, aphidicolin glycinate, ara-C, asparaginase, auristatin, autologous cells or tissues, avastin, azacitidine, azaserine, aziridine, AZQ, *bacillus*, baker's soluble antifol, batimastat, BCG live vaccine, bcl-2 antisense oligonucleotide, BCNU, benzodepa, betamethasone, beta-TGDR, biaomycin, bicalutamide, bisantrene, bleomycin, brequinar, buserelin, busulfan, cactinomycin, calicheamicin, calusterone, campath-1, camptothecin, camptothecin Na salt, capecitabine, carboplain, carboplatin, carboquone, carboxyphthalatoplatinum, carcinoembryonic antigen, carmofur, carmustine, carnptothecin derivatives, carubicin, carzinophilin, CBDCA, CCNU, CHIP, chlorabusin, chlorambucil, chlormadinone acetate, chlornaphazine, chlorozotocin, chromomycins, cisplatin, cisplatinum, cladribine, clomesone, colchicine, colchicine derivative, collagen 14-amino acid peptide, cortisol, cortisone, cyanomorpholinodoxorubicin, cyclarabine, cyclocytidine, cyclodisone, cyclophosphamide, cyclothosphamide, cytarabine, cytochalasin B, cytosine arabinoside, dacarbazine, daclinomycin, dactinomycin, dasatinib, daunorubicin, defosfamide, dehydrotestosterone, demecolcine, denopterin, deoxydoxorubicin, dexamethasone, dianhydrogalactitol, diaziquone, dichlorallyl lawsone, diphtheria toxin, distamycin A, docetaxel, dolastatin 10, doxifluridine, doxorubicin, droloxifene, dromostanolone, duocarmycin/CC-1065, ecteinascidins, edatrexate, eflomithine, elliptinium acetate, emetine, emitefur, endostatin, enocitabine, epipodophyllotoxin, epirubicin, epitiostanol, erbitux, erlotinib, esperamicin, estramustine, estrogen, ethidium bromide, etoglucid, etoposide, fadrozole, fenretinide, fibronectin 29 kDa N-terminal proteolytic fragment, fibronectin 40 kDa C-terminal N-terminal proteolytic fragment, florafbr (pro-drug), floxuridhe, floxuridine, fludarabine, fluorodopan, flutamide, folinic acid, formestane, fosfestrol, fotemustine, gallium nitrate, gefitinib, gemcitabine, gemcitibine, gemtuzumab, glucocorticoid, goserelin, gramicidin D, granulocyte monocyte colony stimulating factor, guanazole NSC 1895, guerin, halichondrin B, hepsulfam, hexamethylmelamine, hexestrol, human chorionic gonadotropin, hycanthone, hydroxyurea, idarubicin, Ifosamide, imatinib, improsulfan, inosine glycodialdehyde, interferon, interferon-alpha, interferon-beta, interferon-gamma, interleukin-12, interleukin-15, interleukin-18, interleukin-1, interleukin-2, interleukin-2, interleukin-6, interleukins, irinotecan, iubidazone, kringle 5, L-alanosine, lapatinib, L-asparaginase, lauprolide acetate, lentinan, letrozole, leuprolide, leuprolide acetate (lupron), levamisole, lidocaine, liposomal dihydroxyanthracindione, lomusline, lomustine, lonidamine, lymphokines, lymphotoxin, lysodren, macbecin, macrophage inflammatory protein, m-AMSA, mannomustine, maytansine, mechlorethamine, mechlorethamine oxide hydrochloride, medroxyprogesterone, megestrol acetate, melanocyte lineage proteins, melengestrol, melphalan, menogaril, mepitiostane, mercaptopurine, mesna, methidiumpropyl-EDTA-Fe (I1)), methotrexate, methotrexate derivative, meturedepa, miboplatin, miltefosine, mineral corticoid, mithramycin, mitobronitol, mitoguazone, mitolactol, mitolanc, mitomycin C, mitotane, mitoxantrone, mitozolamide, mopidamol, morpholinodoxorubicin, mutated tumor-specific antigens, mycophenolic acid, N-(phosphonoacety1)-L-aspartate (PALA), N,N-dibenzyl daunomycin, nerve growth factor, nilotinib, nilutamide, nimustine, nitracine, nitrogen mustard, nogalamycin, nonautologous cells or tissues, novembichin, olivomycins, ontak, onyx-015, oxaliplatin, oxanthrazole, paclitaxel, PCNU, pegaspergase, pelomside A, pentoslatin, peplomycin, perfosfamide, phenamet, phenesterine, picamycin, piperazine, piperazinedione, pipobroman, piposulfan, pirarubicin, piritrexim, platelet derived growth factor, platelet factor-4 7.8 kDa proteolytic fragment, platelet factor-4 13 amino acid peptide, plicamycin, podophyllinic acid 2-ethylhydrazide, podophyllotoxin, polyestradiol phosphate, porfimir, porfiromycin, prednimustine, prednisone, procabazine, procaine, progestine, prolactin 16 kDa proteolytic fragment, propranolol, pseudomonas exotoxin, PSK, pteropterin, puromycin, pyrazofurin, pyrazoloacridine, pyrazoloimidazole, ranimustine, razoxane, retinoid, rhizoxin, rhizoxinlmaytansine, ricin A, rituxan, rituximab, riuxlmab, roquinimex, serpin (serine protease inhibitor), sizofican, sobuzoxane, sorafenib, SPARC, 20-amino acid peptide, spirogermanium, spirohydantoin mustard, straplozocin, streptonigrin, streptozocin, sunitinib, tamoxifen, taxol, taxol derivative, tegafur, temozoamide, teniposide, tenuazonic acid, teroxirone, testolactone, tetracaine, tetraplatin, thalidomide, thiamiprine, thiocolchicine, thioepa, thiopurine, thio-tepa, thrombospondin I 19 amino acid peptide, tissue plasminogen activator, tomudex, topotecan, toremifene, trastuzutmaban, tretinoin, triaziquone, triethylenemelamine, triethylenephosphoramide, triethylenethiophosphoramide, trilostane, trimetrexate, triptorelin, trityl cysteine, trofosfamide, trontecan, tubercidin, tumor necrosis factor-like cytokine, tumor necrosis factors, ubenimex, uracil mustard, uracil nitrogen mustard, uredepa, urethan, vandetanib (ZD6474), VEGF antisense oligonucleotide, vinblastine, vinblastine sulfate, vincristine, vincristine sulfate, vindesine, vinorelbine, VM-26, VP-16, yoshi-864, zinostatin and/or zorubicin.

In another embodiment, one or more immunoconjugates disclosed herein can be administered in combination with one or more of the following cancer therapies or categories of therapeutic agents, including without limitation, radiation, surgery, gene therapy, agents to control of side effects (eg. antihistaminic agents, anti-nausea agents), cancer vaccines, inhibitors of angiogenesis, immune modulators, anti-inflammatories, immunosuppressants, agents that increase expression of antigen, other agents associated with cancer therapy, chemotherapeutic agents, immunotherapeutics, photosensitizers, tyrosine kinase inhibitors, antibiotics, antimetabolites, agents that acts to disrupt DNA, agents that acts to disrupt tubulin, alkylating agents, topoisomerase I inhibitors, topoisomerase II inhibitors, cytokines, growth factors, hormonal therapies, vinca alkyloids, plant alkaloids, and/or anti-mitotic agents.

Indeed, administration of an effective amount of an immunoconjugate to a patient in need of such treatment may result in reduced doses of another cancer therapeutic having clinically significant efficacy. Such efficacy of the reduced dose of the other cancer therapeutic may not be observed absent administration with an immunoconjugate. Accordingly, the present application provides methods for treating a tumor or cancer comprising administering a reduced dose of one or more other cancer therapeutics.

Moreover, combination therapy comprising an immunoconjugate to a patient in need of such treatment may permit relatively short treatment times when compared to the duration or number of cycles of standard treatment regimens. Accordingly, the present application provides methods for treating a tumor or cancer comprising administering one or more other cancer therapeutics for relatively short duration and/or in fewer treatment cycles.

Thus, in accordance with the present application, combination therapies comprising an immunoconjugate and another cancer therapeutic may reduce toxicity (i.e., side effects) of the overall cancer treatment. For example, reduced toxicity, when compared to a monotherapy or another combination therapy, may be observed when delivering a reduced dose of immunoconjugate and/or other cancer therapeutic, and/or when reducing the duration of a cycle (i.e., the period of a single administration or the period of a series of such administrations), and/or when reducing the number of cycles.

Accordingly, the application provides a pharmaceutical composition comprising an immunoconjugate and one or more additional anticancer therapeutic, optionally in a pharmaceutically acceptable carrier.

The present application also provides a kit comprising an effective amount of an immunoconjugate, optionally, in combination with one or more other cancer therapeutic, together with instructions for the use thereof to treat cancer. The kit can also include ancillary agents. For example, the kits can include instruments for injecting the immunoconjugate into a subject, such as a syringe; vessels for storing or transporting the immunoconjugate; and/or pharmaceutically acceptable excipients, carriers, buffers or stabilizers.

As stated above, combination therapy with an immunoconjugate may sensitize the cancer or tumor to administration of an additional cancer therapeutic. Accordingly, the present application contemplates combination therapies for preventing, treating, and/or preventing recurrence of cancer comprising administering an effective amount of an immunoconjugate prior to, subsequently, or concurrently with a reduced dose of a cancer therapeutic. For example, initial treatment with an immunoconjugate may increase the sensitivity of a cancer or tumor to subsequent challenge with a dose of cancer therapeutic. This dose is near, or below, the low range of standard dosages when the cancer therapeutic is administered alone, or in the absence of an immunoconjugate. When concurrently administered, the immunoconjugate may be administered separately from the cancer therapeutic, and optionally, via a different mode of administration.

In an alternate embodiment, administration of the additional cancer therapeutic may sensitize the cancer or tumor to the immunoconjugate or binding protein. In such an embodiment, the additional cancer therapeutic may be given prior to administration of the immunoconjugate or binding protein.

Combination therapy may thus increase the sensitivity of the cancer or tumor to the administered immunoconjugate and/or additional cancer therapeutic. In this manner, shorter treatment cycles may be possible thereby reducing toxic events. The cycle duration may vary according to the specific cancer therapeutic in use. The application also contemplates continuous or discontinuous administration, or daily doses divided into several partial administrations. An appropriate cycle duration for a specific cancer therapeutic will be appreciated by the skilled artisan, and the application contemplates the continued assessment of optimal treatment schedules for each cancer therapeutic. Specific guidelines for the skilled artisan are known in the art. See, e.g., Therasse et al., 2000, "New guidelines to evaluate the response to treatment in solid tumors. European Organization for Research and Treatment of Cancer, National Cancer Institute of the United States, National Cancer Institute of Canada," J Natl Cancer Inst. February 2; 92(3):205-16.

It is contemplated that the immunoconjugate may be administered by any suitable method such as injection, oral administration, inhalation, transdermal or intratumorally, whereas any other cancer therapeutic may be delivered to the patient by the same or another mode of administration. Additionally, where multiple cancer therapeutics are intended to be delivered to a patient, the immunoconjugate and one or more of the other cancer therapeutics may be delivered by one method, whereas other cancer therapeutics may be delivered by another mode of administration.

(G) Diagnostic Methods and Agents Using the Binding Proteins and Immunotoxins The binding proteins disclosed bind selectively on or in cancer cells or to molecules internalized by cancer cells, and not significantly to normal cells. Therefore the binding proteins can be used in the diagnosis of cancer. As stated above, the inventors have shown that the binding proteins of the invention bind to cancer cells.

Accordingly, the present application includes diagnostic methods, agents, and kits that can be used by themselves or prior to, during or subsequent to therapeutic methods in order to determine whether or not cancer cells are present.

In one embodiment, the application provides a method of detecting or monitoring cancer in a subject comprising the steps of (1) contacting a test sample from said subject with the binding proteins or immunoconjugates disclosed herein and that binds specifically to an antigen on or in the cancer cell to produce a binding protein-antigen complex;

(2) measuring the amount of binding protein-antigen complex in the test sample; and (3) comparing the amount of binding protein-antigen complex in the test sample to a control.

In one embodiment, the antigen is prostate stem cell antigen. In another embodiment, prostate stem cell antigen is localized on the cell surface. In another embodiment the antigen is variant HnRNPG. In a further embodiment, variant HnRNPG is localized intracellularly, at the plasma membrane. In another embodiment, the cell expresses both prostate stem cell antigen and variant HnRNPG. In another embodiment, the antigen comprises the epitopes SEQ ID NOS: 23, 41, 111 or 112.

The application further includes a kit for diagnosing cancer comprising any one of the binding proteins or immunoconjugates disclosed herein and instructions for the use thereof to diagnose the cancer. The kit can also include ancillary agents. For example, the kits can include additional reagents, such as agents to detect the binding proteins or immunoconjugates disclosed herein directly or indirectly; vessels for storing or transporting the binding proteins or immunoconjugates; positive and/or negative controls or reference standards; and/or other buffers or stabilizers.

For use in the diagnostic applications, the binding proteins, preferably antibodies or antibody fragments, may be labeled with a detectable marker such as a radio-opaque or radioisotope, such as $^{3}H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion. As described above, methods of attaching a label to a binding protein, such as an antibody or antibody fragment, are known in the art.

Another aspect of the application is a method of detecting or monitoring cancer in a subject comprising the steps of (1) measuring the amount of antibodies disclosed herein in a test sample taken from said subject; and (2) comparing the amount of antibodies disclosed herein in the test sample to a control.

In one embodiment, the amount of antibodies is measured by measuring the amount of antibodies in the test sample, for example by ELISA. In another embodiment, the amount of antibodies is measured by measuring the expression levels of nucleic acids encoding the antibodies disclosed herein in the test sample, for example by RT-PCR.

(H) Pharmaceutical Compositions, Methods and Uses of the Novel Cancer-Associated Epitope The application provides novel cancer-associated epitopes or antigens that is expressed on or in cancer cells and not significantly expressed on or in the normal cells. Thus, the epitopes or antigens can be used in therapies to treat and prevent cancer, including using the epitopes or antigens to elicit an immune response in vivo. In addition, the application includes using the antigens or epitopes to detect or monitor cancer.

(i) Pharmaceutical Compositions

One embodiment is a pharmaceutical composition comprising an effective amount of an epitope or antigen disclosed herein in admixture with a suitable diluent or carrier. Another embodiment is a pharmaceutical composition comprising an effective amount of an isolated nucleic acid encoding an epitope or antigen disclosed herein in admixture with a suitable diluent or carrier. A further aspect of the application is a pharmaceutical composition comprising an effective amount of a recombinant expression comprising a nucleic acid sequence encoding an epitope or antigen disclosed herein in admixture with a suitable diluent or carrier.

For example, the pharmaceutical compositions can be used to treat or prevent cancer. In addition, the pharmaceutical compositions can be used to elicit an immune response in a subject against cancer cells expressing an epitope or antigen disclosed herein.

The pharmaceutical composition can be prepared and administered as discussed above. The pharmaceutical composition can be used in combination with other anti-cancer therapeutic agents as discussed above.

Immunogenicity can be significantly improved if the immunizing agents (i.e. an agent comprising an epitope or antigen disclosed herein or a variant thereof, and/or nucleic acid sequences coding thereof, and/or recombinant expression vectors) and/or composition is, regardless of administration format, co-immunized with an adjuvant. Commonly, adjuvants are used as a 0.05 to 1.0 percent solution in phosphate buffered saline. Adjuvants enhance the immunogenicity of an immunogen but are not necessarily immunogenic in of themselves. Adjuvants may act by retaining the immunogen locally near the site of administration to produce a depot effect facilitating a slow, sustained release of immunogen to cells of the immune system. Adjuvants can also attract cells of the immune system to an immunogen depot and stimulate such cells to elicit immune response. As such, embodiments encompass pharmaceutical compositions further comprising adjuvants.

Adjuvants have been used for many years to improve the host immune responses to, for example, vaccines. Intrinsic adjuvants (such as lipopolysaccharides) normally are the components of killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established. Notwithstanding, it does have limitations. For example, alum is ineffective for influenza vaccination and inconsistently elicits a cell mediated immune response with other immunogens. The antibodies elicited by alum-adjuvanted antigens are mainly of the IgG1 isotype in the mouse, which may not be optimal for protection by some vaccinal agents.

A wide range of extrinsic adjuvants can provoke potent immune responses to immunogens. These include saponins complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes.

In one aspect of the application, adjuvants useful in any of the embodiments described herein are as follows. Adjuvants for parenteral immunization include aluminum compounds (such as aluminum hydroxide, aluminum phosphate, and aluminum hydroxy phosphate). The antigen can be precipitated with, or adsorbed onto, the aluminum compound according to standard protocols. Other adjuvants such as RIBI (ImmunoChem, Hamilton, Mont.) can also be used in parenteral administration.

Adjuvants for mucosal immunization include bacterial toxins (e.g., the cholera toxin (CT), the *E. coli* heat-labile toxin (LT), the *Clostridium difficile* toxin A and the pertussis toxin (PT), or combinations, subunits, toxoids, or mutants thereof). For example, a purified preparation of native cholera toxin subunit B (CTB) can be of use. Fragments, homologs, derivatives, and fusion to any of these toxins are also suitable, provided that they retain adjuvant activity. Preferably, a mutant having reduced toxicity is used. Suitable mutants have been described (e.g., in WO 95/17211 (Arg-7-Lys CT mutant), WO9606627 (Arg-192-Gly LT mutant), and WO 95/34323 (Arg-9-Lys and Glu-129-Gly PT mutant)). Additional LT mutants that can be used in the methods and compositions disclosed herein include, for example Ser-63-Lys, Ala-69-Gly, Glu-1,0-Asp, and Glu-1,2-Asp mutants. Other adjuvants (such as a bacterial monophosphoryl lipid A (MPLA) of various sources (e.g., *E. coli, Salmonella minnesota, Salmonella typhimurium*, or *Shigella flexneri*, saponins, or polylactide glycolide (PLGA) microspheres) can also be used in mucosal administration.

Adjuvants useful for both mucosal and parenteral immunization include polyphosphazene (for example, WO9502415), DC-chol (3 b-(N—(N',N'-dimethyl aminomethane)-carbamoyl) cholesterol (for example, U.S. Pat. No. 5,283,185 and WO 96/14831) and QS-21 (for example, WO8809336).

A subject may be immunized with a pharmaceutical composition comprising one or several epitopes or antigens disclosed herein, an isolated nucleic acid sequence encoding thereof and/or a recombinant expression vectors by any conventional route as is known to one skilled in the art. This may include, for example, immunization via a mucosal (e.g., ocular, intranasal, oral, gastric, pulmonary, intestinal, rectal, vaginal, or urinary tract) surface, via the parenteral (e.g., subcutaneous, intradermal, intramuscular, intravenous, or intraperitoneal) route or intranodally. Preferred routes depend upon the choice of the immunogen as will be apparent to one skilled in the art. The administration can be achieved in a single dose or repeated at intervals. The appropriate dosage depends on various parameters understood by skilled artisans such as the immunogen itself (i.e. peptide vs. nucleic acid (and more specifically type thereof)), the route of administration and the condition of the animal to be vaccinated (weight, age and the like).

The application also provides kits comprising an effective amount of an epitope or antigen disclosed herein, optionally, in combination with one or more other cancer therapeutic, together with instructions for the use thereof. The kit can also include ancillary agents. For example, the kits can include instruments for injecting an epitope or antigen disclosed herein into a subject, such as a syringe; vessels for storing or transporting the epitope or antigen disclosed herein; adjuvants; and/or pharmaceutically acceptable excipients, carriers, buffers or stabilizers.

(ii) Therapeutic Methods

As mentioned above, the epitopes or antigens disclosed herein are present on or in cancer cells, but not significantly on or in normal cells. Thus, an epitope or antigen disclosed herein can be used in therapeutic methods to prevent or treat cancer. In addition, an epitope or antigen can be used to elicit an immune response in a subject, for example in a vaccine.

One embodiment is the use of an epitope or antigen disclosed herein in the manufacture of a medicament to treat or prevent cancer. Another embodiment is the use of an epitope or antigen in the manufacture of a medicament to elicit an immune response in a subject.

The application also includes the use of an isolated nucleic acid sequence encoding an epitope or antigen disclosed herein in the manufacture of a medicament to treat or prevent cancer. In addition, the application includes the use of an isolated nucleic acid sequence encoding an epitope or antigen in the manufacture of a medicament to elicit an immune response in a subject.

A further embodiment is the use of the recombinant expression vector comprising an isolated nucleic acid sequence encoding an epitope or antigen disclosed herein in the manufacture of a medicament to treat or prevent cancer. Also, the application includes the use of the recombinant expression vector comprising an isolated nucleic acid sequence encoding an epitope or antigen disclosed herein in the manufacture of a medicament to elicit an immune response in a subject.

An additional embodiment is a method of treating or preventing cancer in a subject having or suspected of having cancer comprising administering to said subject an effective amount of an epitope or antigen disclosed herein. In addition, the application includes a method of treating or preventing cancer in a subject having or suspected of having cancer comprising administering to said subject an effective amount of an isolated nucleic acid sequence encoding an epitope or antigen disclosed herein. Further, the application includes a method of treating or preventing cancer in a subject having or suspected of having cancer comprising administering to said subject an effective amount of a recombinant expression vector comprising an isolated nucleic acid sequence encoding an epitope or antigen disclosed herein.

Another embodiment is a method of inducing an immune response in a subject against cancer comprising administering to said subject an effective amount of an epitope or antigen disclosed herein. In addition, the application includes a method of inducing an immune response in a subject against cancer comprising administering to said subject an effective amount of an isolated nucleic acid sequence encoding an epitope or antigen disclosed herein. Further, the application includes a method of inducing an immune response in a subject against cancer comprising administering to said subject an effective amount of a recombinant expression vector comprising an isolated nucleic acid sequence encoding an epitope or antigen disclosed herein.

(iii) Diagnostic Methods

The epitopes or antigens disclosed herein are expressed on or in cancer cells and is not significantly expressed on or in normal cells, thus the detection of an antigen or epitope disclosed herein can be used as a diagnostic method for cancer.

One embodiment is a method of detecting or monitoring cancer in a subject having or suspected of having cancer, comprising detecting an antigen or epitope disclosed herein on or in a cell in the sample, wherein cancer is indicated, if one or more antigen or epitopes disclosed are detected on or in the cell.

A number of techniques can be used to detect the antigens or epitopes disclosed herein on or in a cell. For example, the binding proteins disclosed herein can be used in immunoassays to detect cell surface expression of an antigen or epitope disclosed herein. A person skilled in the art will appreciate that a number of techniques can be used to detect and/or quantify cell surface expression of the epitope or antigen, including Western blots, immunoprecipitation followed by SDS-PAGE, immunocytochemistry, FACS, protein arrays, and the like.

Another aspect of the present application is a method of detecting or monitoring cancer in a subject having or suspected of having cancer, comprising detecting the expression of an antigen or epitope disclosed herein in the cell in the sample, wherein cancer is indicated, if expression of an antigen or epitope disclosed herein is detected in the cell. In one embodiment, an RNA expression product encoding an antigen or epitope disclosed herein is used to detect the expression of an antigen or epitope disclosed herein in the cell. One skilled in the art will appreciate that the RNA expression product can be detected or quantified by detecting mRNA encoding an antigen or epitope disclosed herein, or oligonucleotides, cDNA, DNA, RNA, PCR products, synthetic DNA, synthetic RNA, or other combinations of naturally occurring or modified nucleotides which specifically and/or selectively hybridize to the mRNA encoding an antigen or epitope disclosed herein.

A number of methods can be used to detect and/or quantify RNA expression of an antigen or epitope disclosed herein in a cell including RT-PCR, nuclease protection assays, such as ribonuclease protection assays and S1 nuclease assays, and Northern blots and the like.

One embodiment is a method for detecting or monitoring cancer by screening for the presence or expression of variant HnRNPG. In one embodiment, the method comprises the steps:

(a) determining the expression of variant HnRNPG in a test sample from a subject; and (b) comprising the expression of variant HnRNPG with a control;

wherein a difference in expression of variant HnRNPG between the control and test sample is indicative of cancer.

The above disclosure generally describes the present invention. A more complete understanding can be obtained by reference to the following specific examples. These examples are described solely for the purpose of illustration and are not intended to limit the scope of the invention. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present invention:

EXAMPLES

Example 1

Generation of VB1-213 Monoclonal Antibody

The VB1-213 monoclonal antibody was generated from the lymph nodes of an ovarian cancer patient. MFP-2 was used as the fusion partner to generate the monoclonal antibody (U.S. Pat. No. 7,220,559; U.S. Pat. No. 6,197,582). VB1-213 is an IgG1, lambda monoclonal antibody.

Messenger RNA (mRNA) was isolated from hybridoma cells and first strand complement DNA (cDNA) was synthesis using the reverse transcriptase enzyme. The cDNA was then used to isolate antibody H and L chain genes by PCR. PCR primers were designed (see note) according to the consensus framework regions of the H (Gamma) and L (Lambda) chain isotypes. The PCR products were individually cloned into the TOPO-pCR 2.1 vector and transformed into *E. coli* cells. Individual clones containing the inserts in TOPO-pCR 2.1 were isolated and grown. Plasmid DNA was purified and sequenced.

```
Gamma Primers:
                                        (SEQ ID NO: 1)
1) 5' CTC ACC ATG GAG TTT GGG CTG AGC TGG GTT 3'

                                        (SEQ ID NO: 2)
2) 5' CAG GCA GCC CAG GGC CGC TGT GCC CCC AGA
GGT GCT 3'

Lambda Primers:
                                        (SEQ ID NO: 3)
(1) 5' ATG RCC TGS WCY CCT CTC YTY CTS WYC 3'

                                        (SEQ ID NO: 4)
(2) 5' ATG RCC TGS WCY CCT CTC YTY CTS WYC 3'

                                        (SEQ ID NO: 5)
(3) 5' ATG RCC TGS WCY CCT CTC YTY CTS WYC 3'

                                        (SEQ ID NO: 6)
(4) 5' GGT GGT CTC CAC TCC CGC CTT GAC GGG GCT
GCC ATC TGC 3'
Note:
In order to isolate the lambda chain, a mixture of 5' primers
are used with mixed bases for certain consensus sequences: R = A
+ G, S = C + G, W = A + T, Y = C + T.
```

The PCR reaction included a 50 μL reaction volume containing:

| | | |
|---|---|---|
| 10X PCR buffer | 5 | μL |
| 2 mM dNTPs | 5 | μL |
| Primer 5' | 20 | pmol |
| Primer 3' | 20 | pmol |
| Taq DNA Polymerase | 2.5 | U |
| DNA template | 50 | ng |

The PCR cycling conditions were: 94.degree. C. for 1 min., 62.degree. C. for 1 min., 72° C. for 1 min. for 30 cycles and a final extension for 10 min. at 72° C. Amplified PCR products were electrophoretically separated on a 1% agarose gel, excised, purified using a Qiaquick™ gel extraction kit, cloned into the TOPO pCR 2.1 cloning vector and then DNA sequenced using the 373 DNA sequencer stretch, (Griffin G. H. and Griffin M. A.: PCR technology, Current innovations. CRC Press, Boca. Raton. Fla. 3431. USA; (Cloning vector pCR 2.1, Catalogue #205184. Invitrogen, Carlsbad, Calif.; Qiagen, Qiaquick™ gel extraction kit, Catalogue #28706. Qiagen Inc., Mississauga, ON and 373 DNA Stretch. PE Applied Biosystems, Mississauga ON.).

The CDR sequences (SEQ ID NO: 7-12) for VB1-213 are shown in Table 1. The heavy chain variable region and the light chain variable region are shown in FIGS. 1 and 2, respectively (SEQ ID NO: 13-16).

Example 2

Antibody Profiling by Measuring Tumor Cell Reactivity

VB1-213 was tested by flow cytometry for tumor cell reactivity against four different types of epithelial cancers selected on the basis of tumor microarray results shown in Example 4. The VB1-213 results are summarized in Table 2. MF values indicate the mean calculated from the sum of the mean fold increase in median fluorescence over the control antibody from all cell lines in each indication. The strongest binding was to lung (A-549, NCI-H460) followed by prostate (DU-145, PC-3, LNCaP), melanoma (A-375, SK-MEL-28) and breast (MDA-MB-231, MDA-MB-435S, SK-BR3).

Example 3

Normal

Optimal conditions for staining were defined by testing VB1-213 binding to SK-OV-3 tumor cell line. SK-OV-3 is an ovarian tumour cell line and staining optimization is routinely performed using a cell line representative of the type of tumour from which the antibody was derived (lymph nodes of an ovarian cancer patient in this case). VB1-213 staining was detected in the membrane, cytoplasm and nuclei of these cells. Representative pictures of cell membrane staining of formalin-fixed cell pellet cores are shown in FIG. 3.

Once the optimal staining conditions were identified, the antibody was tested in comparison with an isotype control (IgG Myeloma) on a low-density (LD) array of critical normal tissue for normal tissue reactivity. The tissue microarray results for VB1-213 are summarized in Table 3. No significant membrane staining of any of the normal critical tissues was observed except for lung. The maximum score for membrane staining was no more than 20% positive cells.

Example 4

Tumor

VB1-213 was tested in a HD formalin-fixed tumor tissue microarray for tumor tissue reactivity (Table 4). The highest VB1-213 reactivity was detected against lung, liver, prostate and skin cancer tissue. Moderate to low binding was observed against breast, pancreas and head and neck carcinoma.

Figure 4:
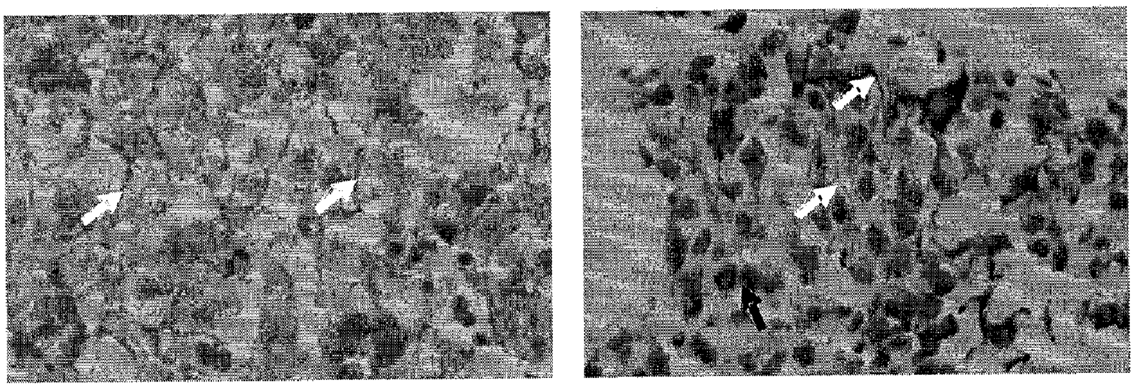
FIG. 4 shows (A) Lung cancer tissue stained with VB1-213; 400X; Membrane staining (grade 2+) is observed (white arrows) along with some cytoplasmic staining. (B) Prostate cancer tissue stained with VB1-213; 400X; Membrane staining is indicated by the white arrows. Also, nuclear (black arrow) and string cytoplasmic staining are observed.

Representative pictures illustrating the binding of VB1-213 to some of the cancers are shown in FIGS. 4 A and B. Membrane staining observed on the skin tumor tissues was considered as non-specific binding since it was also detected with the control isotype antibody.

Example 5

Figure 5:
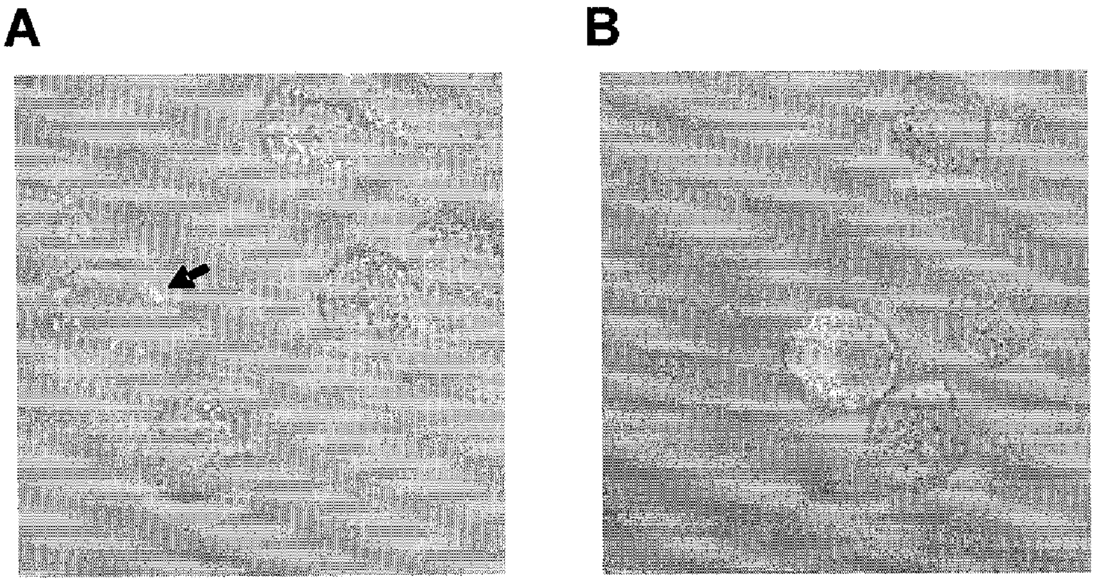
FIG. 5 shows assessing internalization of VB1-213 by confocal microscopy. A-375 cells were incubated with VB1-213 at 4° C., washed and warmed to 37° C. for 60 min. Cells were fixed, permeabilized and labeled with fluorescent-labeled second antibody. A), Fluorescence labeling of A-375 cells after incubation of VB1-213 at 4° C. for 60 min, displaying punctuate surface distribution of labeling indicated by the black arrow, (60X×3) magnification. B), Following incubation of antibody-bound cells at 37° C. for 60 min, the cells show intracellular staining by internalized antibody, (60X×3) magnification.

Assessment of VB1-213 Binding and Internalization by Flow Cytometry and Confocal Microscopy VB1-213 and control antibody 5E9 that demonstrate strong reactivity against the tumor cell line A-375 were used to assess VB1-213 for internalization by direct visualization of fluorescence distribution and intracellular staining with the aid of laser scanning confocal microscopy. A-375 cells were incubated with VB1-213 (100 mg/mL) at 4° C. After washing the cells, half of the sample was warmed at 37° C. for 1 hr, the other half maintained at 4° C. Cells were unfixed or fixed (with a solution of formaldehyde) and labeled with fluorescein-labeled second antibody. Like 5E9, incubation of A-375 cells with VB1-213 at 4° C. for 60 min demonstrated punctuated surface distribution of fluorescence label (FIG. 5A). Warming the VB1-213 antibody bound cells to 37° C. revealed a punctuated pattern of intracellular staining by the internalized antibody within 60 minutes, as shown in FIG. 5B.

Example 6

Binding Affinity

Figure 6:
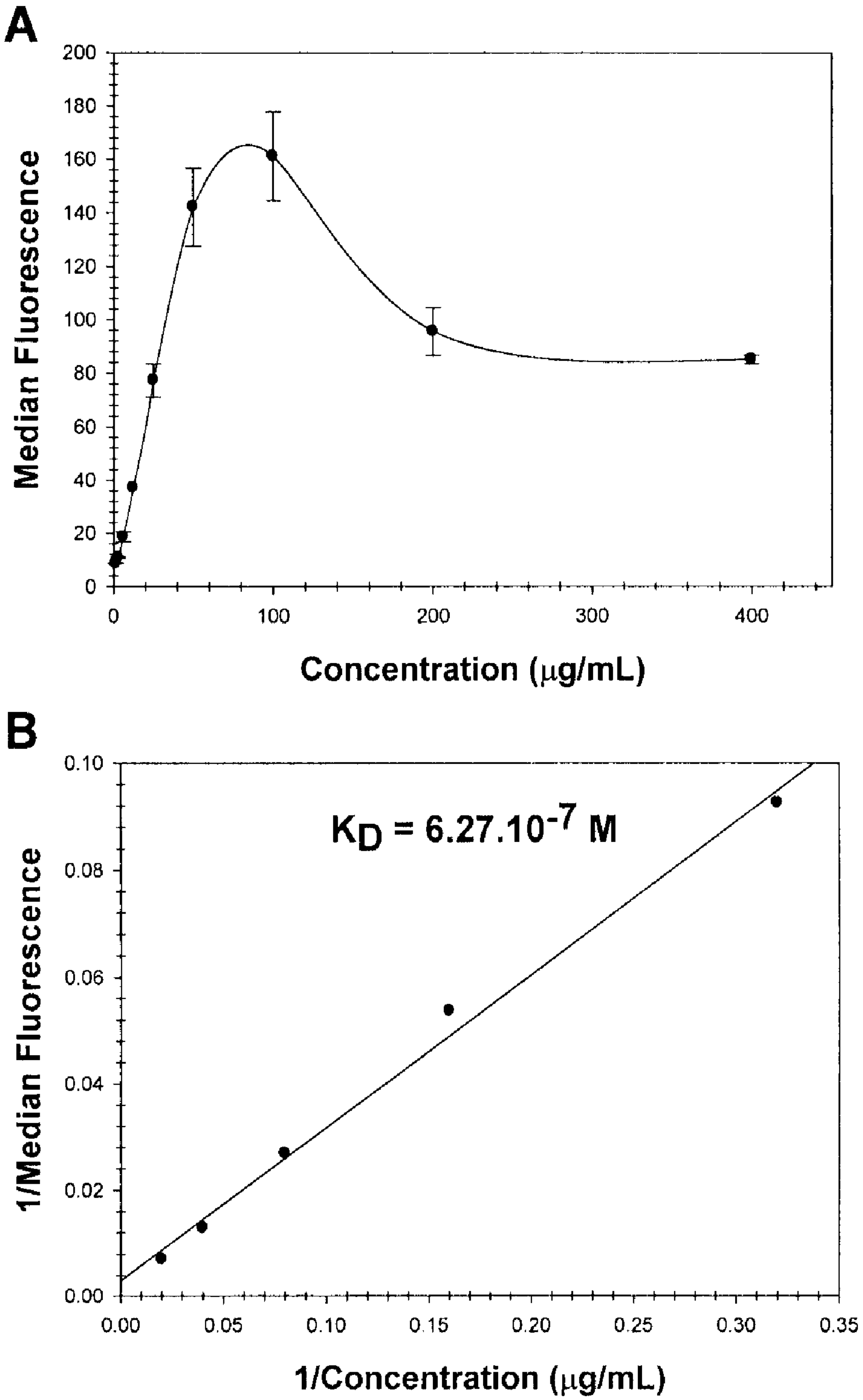
FIG. 6 shows binding affinity of VB1-213: A) saturation curve of VB1-213 was determined by measuring the reactivity of increased concentrations of VB1-213 to the A-375 carcinoma cells by flow cytometry; B: Lineweaver-Burk Method, the binding constant was determined by Lineweaver-Burk method.

Flow cytometry was used to assess binding affinity (C. A. Benedict, A. J. MacKrell, W. F. Anderson, *J. Immunol. Methods* 201, 223 (1997)). A range of antibody concentrations were tested against a fixed number of tumor cells (A-375) for 2 hours to obtain a saturation curve. Values and graphical analysis were generated using Sigma Plot (Jandel Scientific, San Rafael, Calif.). The inverse of the determined median fluorescence was plotted as a function of the inverse of antibody concentration to determine KD by the Lineweaver-Burk method. A straight line was generated and the KD was calculated from the slope of the curve (FIGS. 6A and 6B). The dissociation constant, KD value, was determined by the following equation: 1/F=1/Fmax+(KD/Fmax) (1/IgG), where F=background subtracted median fluorescence and Fmax was calculated from the plot. The dissociation constant for VB1-213 was shown to be $6.27\times10^{-7}$ M.

Example 7

VB1-213 Antigen Identification

More detailed information on this method can be found in WO2006/105653.

Cells

Prostate tumor cell line, DU-145, breast cancer cell lines, MDA-MB 435S & SKBR-3; pancreatic cell lines, PANC-1 & CFPac-1; and T-cell line-Daudi were used in the study (Table 5). These cell lines were selected based on the results of tumor cell line profiling by flow cytometry.

Growth and Maintenance of Tumor Cell Lines

The cell lines in the study were purchased from ATCC and cultured in accordance with the guidelines and recommendations of ATCC. Cells were harvested at 90% confluence with viability>90%.

Preliminary Characterization of the Antigen Binding to VB1-213

Preliminary characterization data was obtained from experiments designed to assess the feasibility of the gel-based approach by dot blot assays; and from experiments performed to determine the nature of the epitope associated with the antigens.

The data from these experiments classified the VB1-213 antigen as a "blottable" antigen with a peptide epitope. It should be noted that the antigen could be glycosylated at sites other than the binding site as well.

Immunoprecipitation

A minimum of 500 μg membrane protein was used for immuno-affinity precipitation. A pre-clearing step using protein-G sepharose alone was the first step in the purification of the antigen prior to the addition of the antibody. In certain cases, pre-clearing was performed twice to add more stringency to the assay. A total of 50 μg of antibody was used as the precipitating agent in the mixture. The antigen-antibody mixtures were nutated overnight at 4° C. using buffer conditions that mimicked physiological conditions. Care was taken to ensure that protease inhibitors were used in every step of the antigen isolation process.

Immune complexes were centrifuged, washed with RIP-A lysis buffer and eluted with 0.2 M glycine pH 2.5. Supernatants representing the unbound fractions were stored to test the proteins that were not isolated by affinity purification. Immunoprecipitations were carried out on one strongly positive cell line (DU-145), two moderately positive cell lines (MDA-MB-435S and Panc-1), one weakly positive cell line (SKBR-3) and two negative cell lines, (CFPAC-1 and Daudi), using VB1-213 and equal amounts of 4B5 (isotype-matched control) processed in parallel at all times.

Figure 7:
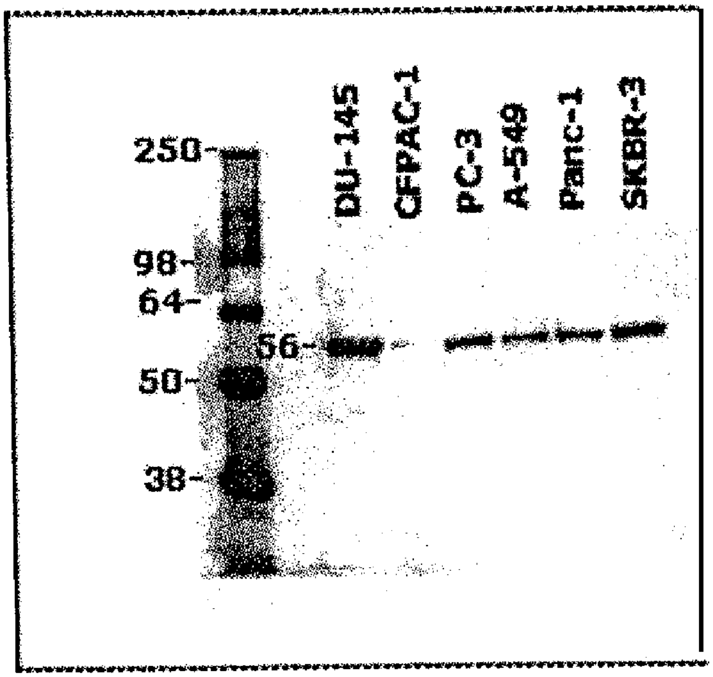
FIG. 7 is a Western blot analyses of VB1-213-reactive proteins following immunoprecipitation using VB1-213. A cell panel of five positive cell lines, namely, DU-145, PC-3, A549, Panc-1, and SKBR-3, and one negative cell line, namely, CF-Pac-1 was used.

Gel-Based Analysis and Western Blotting:

The immunoprecipitated proteins were subjected to reducing conditions of sample preparation and were subsequently analyzed by SDS-PAGE/Western Blotting. The immunoprecipitated proteins were treated with sample buffer containing 1% β-mercapto ethanol at 65° C. for 15 minutes. The resulting blots were probed with the relevant antibodies and corresponding secondary antibodies conjugated to HRP, to visualize the immunoprecipitated proteins by chemiluminescence. One specific band was detected at −56 kDa (FIG. 7) in DU-145, PC-3, A549, SKBR-3 and Panc-1. The same band was under-expressed in the VB1-213 non-reactive cell line, CFPAC-1. None of the cell lines showed positive immunoprecipitation with 4B5.

Figure 8:
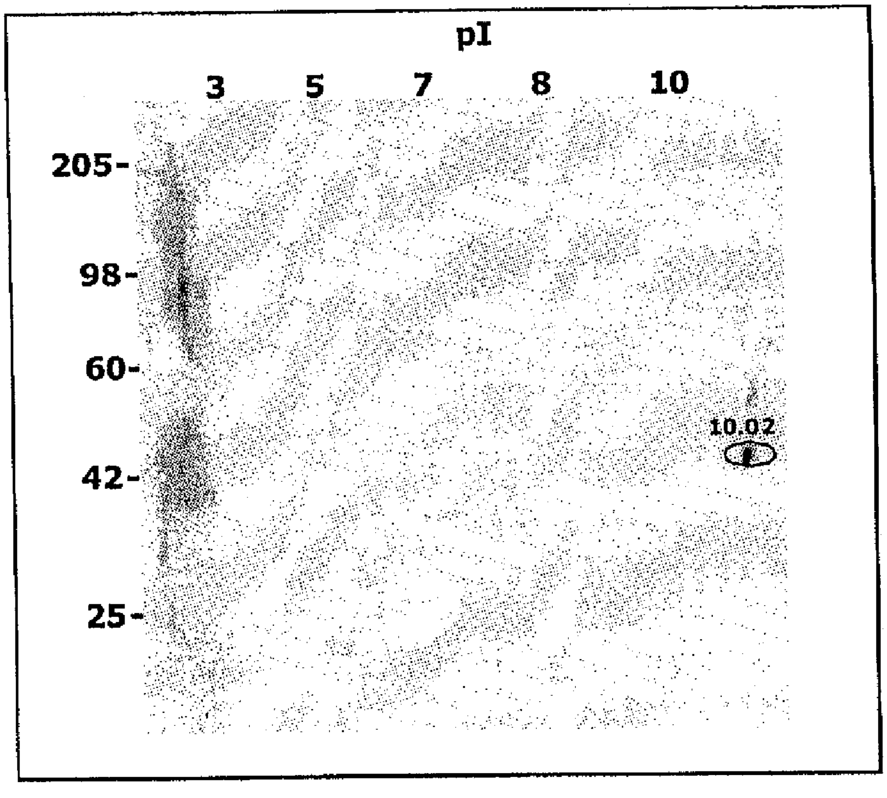
FIG. 8 is a Western blot profile of the 2D-PAGE obtained on probing with VB1-213. The corresponding spot (circled) from the gel was used for identification purposes.

In order to determine isoelectric points (pl) and assess the possibility of protein stacking in the 1D-PAGE analysis, the immunoprecipitated proteins for VB1-213 were separated on two-dimensional polyacrylamide gel electrophoresis (2D-PAGE), transferred to PVDF membranes, probed with VB1-213 and detected by ECL (chemiluminescence). Shown in FIG. 8, one spot was detected at ~42 kDa/pl=10.02. The corresponding protein band or spot from the both the 1D and 2D coomassie stained gels were excised and processed for peptide extraction.

Peptide Extraction and Antigen ID:

Proteins from 1D-gel band and 2D-spots were digested with trypsin to release them from the gel and analyzed on a reverse-phase LC-MS/MS system and a static nanospray for better coverage. The identities of the proteins were revealed by database analysis using standard bioinformatics tools. Raw data included peptides obtained as listed in the TOF MS spectra, MS/MS fragmentation data, and a list of suggested proteins including contaminants that do not match the pl or the molecular weight of the isolated protein. To obtain complete analysis MS/MS spectra were submitted directly to Mascot search engines accessible through www.Matrixscience.com. Tryptic digestions were performed with sequencing grade trypsin in a 20-hour peptide extraction process finally resulting in the extraction of peptides that were analyzed on a QSTAR Pulsar-I (ESI-qTOF-MS/MS) equipped with a nanosource with a working flow rate of 20-50 mL/min using a static nanospray and in an LC-mode. The ionized peptides were detected as doubly, triply or quadruply charged molecules which were then refined to their respective masses. De-novo sequencing of the identified proteins was also performed whenever possible. Peptides were extracted from both positive and negative cell lines to ensure to ensure identification of the correct antigen. Peptide masses extracted from the mass spectra were used directly to identify the antigen according to the MOWSE scores obtained on protein databases that are accessible through search engines such as MASCOT, SEQUEST, and Prospector.

Figure 10:
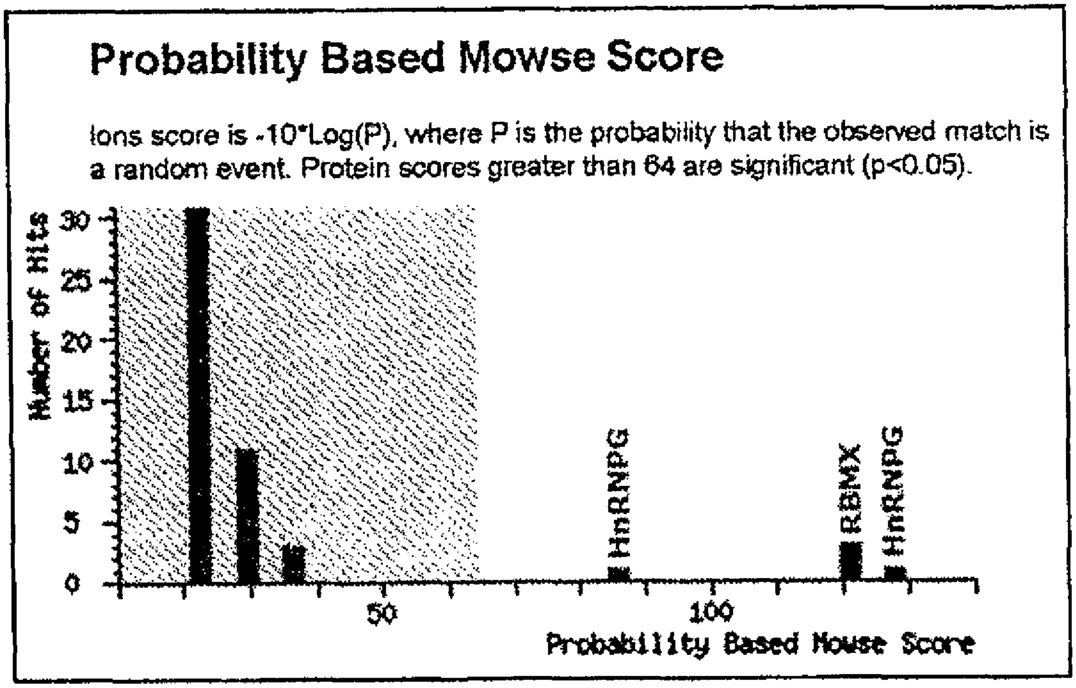
FIG. 10 is a peptide mass fingerprinting results for the peptides recovered from VB1-213 reactive protein spot from the 2D-PAGE gel: Protein scores greater than 64 were considered significant.
Figure 16:
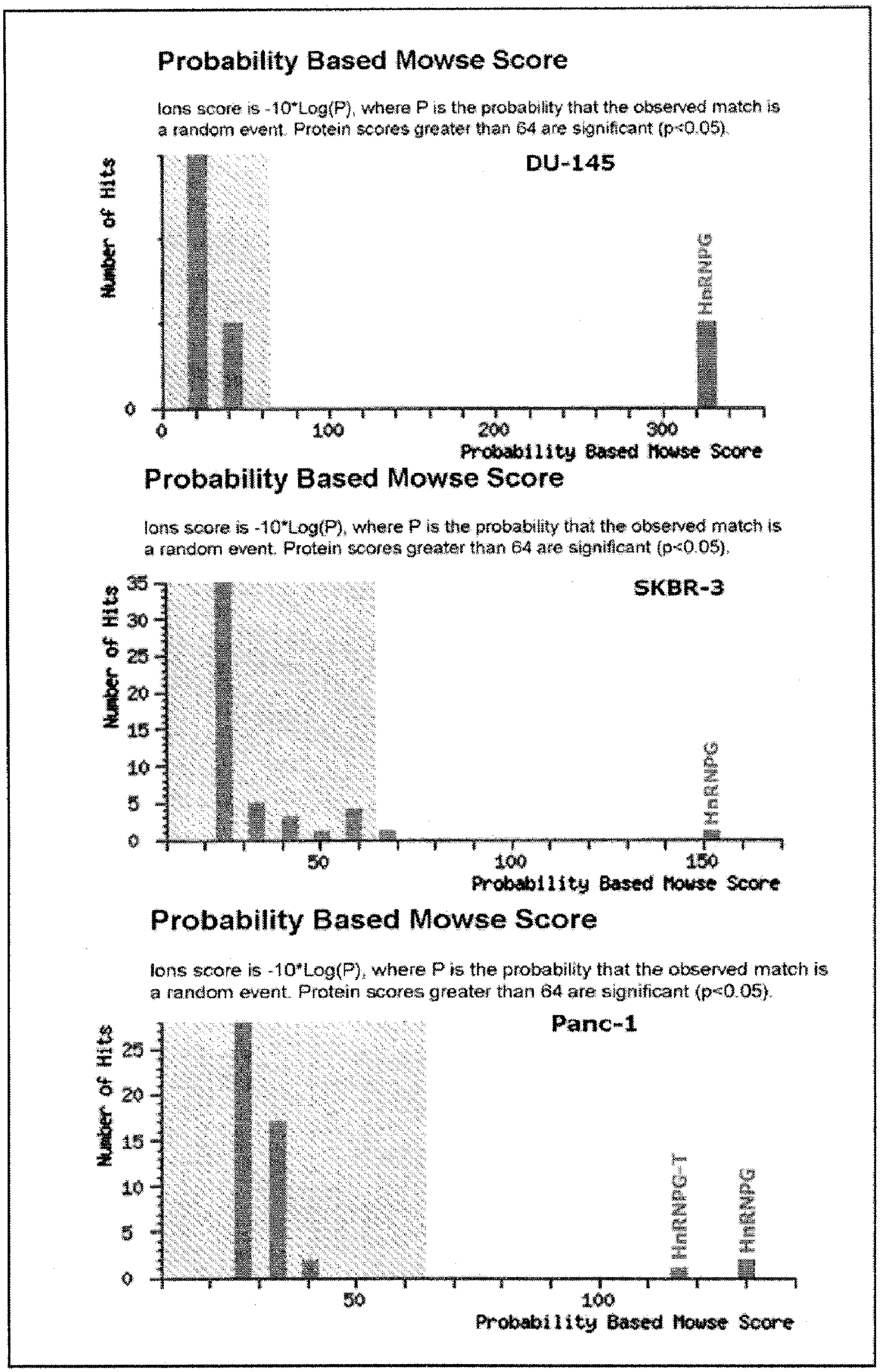
FIG. 16 shows peptide mass fingerprinting results for the peptides recovered from in-gel digests of VB1-213 immunoprecipitates: Protein scores greater than 64 were considered significant.

The protein spot excised from the 2D-gel of DU-145 membrane fractions was identified as HnRNPG (FIGS. 9 and 10). The pl and the molecular weight clearly matched that of HnRNPG. A total of 38% sequence coverage with 18 matching peptides was obtained, (Table 6) (SEQ ID NO 53-70) 17 of which showed 100% homology to the original protein. A discrete nanospray head installed on a nanosource was used for MS/MS fragmentation of peptide 1481.9584 (SEQ ID NO: 70): The collision energy was 48V, curtain gas and CAD gas were maintained at 25 and 6, respectively, and the sample allowed to cycle for 1.667 minutes (100 cycles) to obtain stable mass ion fragmentation. MS/MS fragmentation of the peptide (1481.9584, 742.000000, 2+) (SEQ ID NO 70) gave rise to the fragment ions shown in FIG. 11. The peptide, DGYSCKAQYSNRD (SEQ ID NO 70), showed 100% homology to HnRNPG in the flanking sequences but not with the sequence in the middle, indicating an identification of a novel sequence. The list of peptides recovered and their mapped positions to the sequence from HnRNPG are as given in FIG. 12 and Table 6. All peptides represented were obtained by de novo sequencing.

Analysis of the 56±2 kDa Band Purified from 1D-Gels:

The data obtained from the mass spectra of all three cell lines, DU-145, SKBR-3 and Panc-1 point towards HnRNPG as the antigen that binds to VB1-213 (FIGS. 13, 14, 15, and 16). Of all the cell lines screened, Prostate cell line, DU-145 showed the highest scoring identity. SKBR-3, a breast cancer cell line and Panc-1, a pancreatic cell line also showed an over-expression of the antigen. The membrane preparations from each of these cell lines were used to affinity purify the VB1-213 antigen. TOF-MS scans were obtained. The presence of HnRNPG in the immunoprecipate obtained with the VB1-213 antibody is supported by the data. There is however, a difference in the expected molecular weight of HnRNPG (42 kDa) and the molecular weight of the band observed on the 1D gels (56 kDa). In-solution liquid-phase analysis was performed to clarify this apparent discrepancy.

Figure 17:
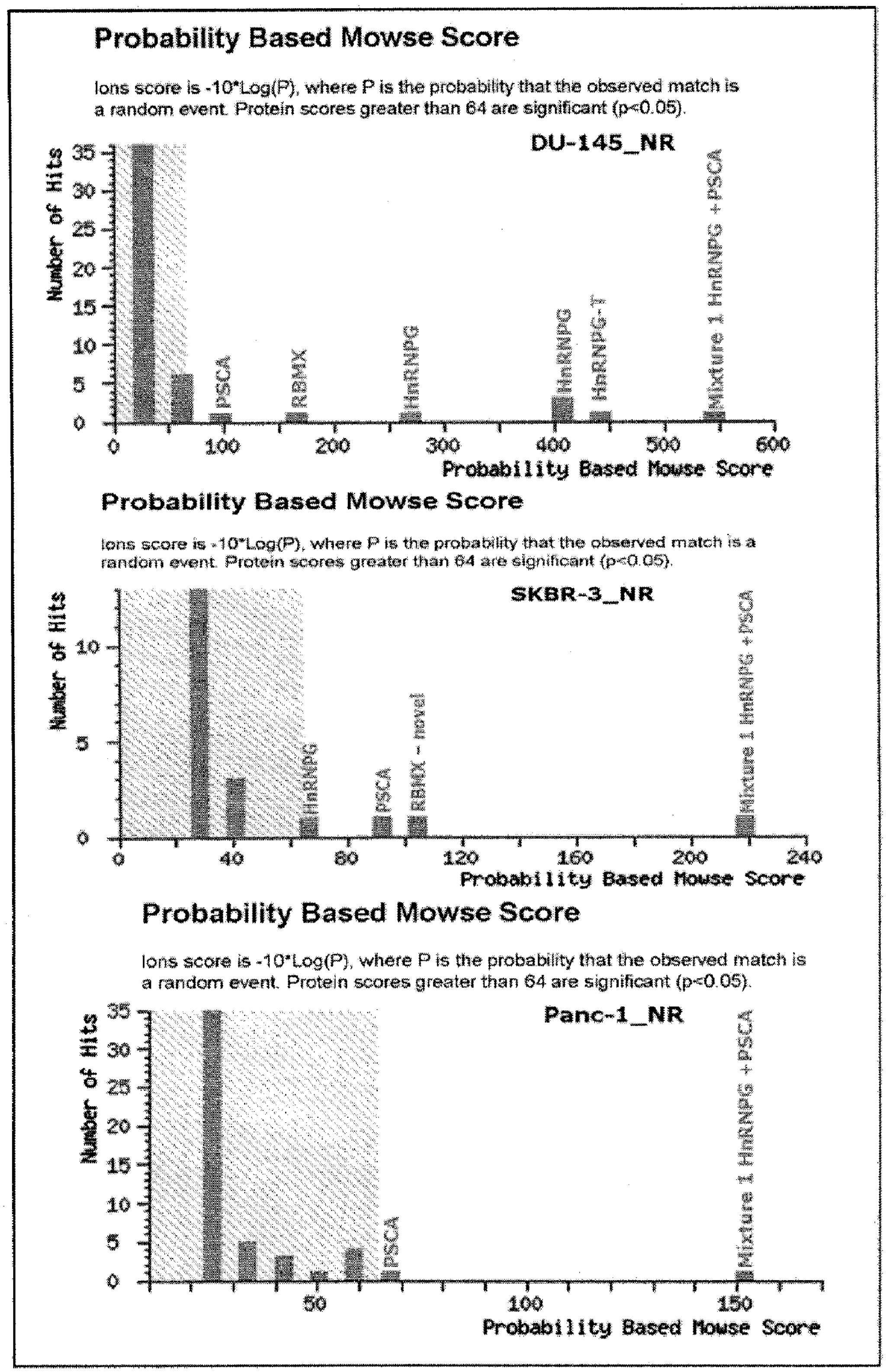
FIG. 17 shows peptide mass fingerprinting results for the peptides recovered from in-solution digests of VB1-213 immunoprecipitates: Protein scores greater than 64 were considered significant.

Analysis of Peptides Extracted from in-Solution Digests:

The immunoprecipitates from the three positive cell lines, DU-145, SKBR-3 and Panc-1 were directly subjected to in-solution peptide extraction. The extracted peptides were concentrated and desalted using μ-C18 columns and used for MS analysis. Two distinct proteins were identified, in all three cell lines, as "Mixture1", consisting of HnRNPG+Prostate stem cell antigen (PSCA). The identified protein entities and their respective scores are also presented in FIG. 17. HnRNPG and PSCA were identified as a "Mixture1", each with 76% and 95% sequence coverage and a highly significant combined score of 413. The sequence coverage and peptides corresponding to PSCA are shown in FIGS. 18 and 19 and Table 7 (SEQ ID NO: 18 to 22). The peptides isolated by this method corresponding to HnRNPG as shown in Table 8 (SEQ ID NO: 72 to 110). MS/MS fragmentation and identity of peptides confirm that HnRNPG and PSCA are present in the immunoprecipitate obtained with VB1-213.

MS/MS Fragmentation of the Abundant Peptides:

MS/MS fragmentation of four of the peptides (1866.000 from (623.000.000000, 3+) (SEQ ID NO: 21); 1481.985448 from (742.000000, 2+) (SEQ ID NO 70); 2089.96 from (698.000000, 3+) (SEQ ID NO 84); 1486.6418 from (744.600000, 2+) (SEQ ID NO 75) gave rise to the fragment ions that mapped to peptides from PSCA and HnRNPG; respectively. Since these four peptides were well detected in TOF-MS, these peptides were used for MS/MS ion fragmentation apart from the peptides derived from mass fingerprinting. A discrete nanospray head installed on a nanosource was used for this purpose. The collision energy was 48V, curtain gas and CAD gas were maintained at 25 and 6, respectively, and the sample allowed to cycle for 1.667 minutes (100 cycles) to obtain stable mass ion fragmentation. Peptides derived from the spectra clearly matched the sequences on HnRNPG and PSCA, except for peptide, 1481.95, 742.00000, 2+ (SEQ ID NO 70). The flanking regions of the recovered peptide exactly matched HnRNPG; however the rest of the sequence showed only 69.6% homology in the sequence information This proved to be a novel sequence, with four amino acid replacements at positions, 216, 218, 219 and 222 of HnRNPG. These four changes also create a peptide sequence YSCKAQYSNRD (SEQ ID NO:111) in HnRNPG that is 81% homologous to a peptide in PSCA. The ion fragmentation data further confirm the identity of variant HnRNPG and PSCA as the cognate antigens for VB1-213.

PSCA as the Cell Surface Antigen and HnRNPG as an Intracellular Protein:

The above data indicate PSCA is an antigen recognized by VB1-213. Due to the limitations of the gel-based purifications, PSCA was not identified in any of the preparations except in liquid-phase extractions. Therefore, in order to further confirm that PSCA is a VB1-213 antigen, anti-PSCA (a commercially available antibody against PSCA) was purchased for validation experiments. Two cell lines Daudi (T-cell line) and Panc-1 (VB1-213+ve) were immunoprecipitated with anti-PSCA and the eluates resolved on SDS-PAGE and Western blotting. The blots were probed both with anti-PSCA and VB1-213. As can be seen in FIG. 20, positive bands at the same positions (56 kDa) were seen reacting to both antibodies. A single band at 56 kDa was detected when probed with VB1-213 or anti-PSCA, as opposed to two bands at ~13 kDa or ~42 kDa, suggesting that HnRNPG and PSCA together form a complex instead of binding to VB1-213 independent of each other. Daudi (previously negative for 213) showed the reactive band at ~56 kDa with both antibodies. MS analysis of the protein band from Daudi did not yield usable results, with only remants of the antibodies being identified.

An experiment was designed to test the presence of HnRNPG on the cell surface. DU-145 cells were treated with trypsin for 30 minutes and the supernatant containing proteins released from the cell surface was concentrated and used for MS analysis. Only PSCA, and other extra-cellular matrix proteins and serum proteins were detected. There were no peptides belonging to HnRNPG in the supernatant. Therefore, mutant HnRNPG is found in the cell membrane preparation but is localized on the cytoplasmic side. The data suggest that HnRNPG and PSCA are co-expressed in tumour and that they may be associated at the cell membrane level and/or co-migrate in gels after immunoprecipitation.

Example 8

Epitope Mapping-Binding Experiments

Methods and Reagents
Peptides:

Synthetic peptides were custom synthesized by Global Peptides LLC (Fort Collins, Colo. USA). The amino acid sequence of HP1 (Biotin YSCKAQVSNED—1467.76 amu; SEQ ID NO: 23) was derived from PSCA and was hypothesized to be the peptide to which VB1-213 binds on PSCA since this peptide was 81% homologous (only 2 amino acids different) to a peptide on variant HnRNPG (SEQ ID NO 111), an antigen that also binds VB1-213. Another peptide, PSpep3 (Biotin LCNASGAHALQ—1306.59 amu; SEQ ID NO: 24), was derived from PSCA; and two other peptides that are part of the immunogen of the commercial anti-PSCA antibodies, namely PSpep1 (Biotin TARIRAVGLLTVISK—1823.9 amu; SEQ ID NO: 25) and PSpep2 (Biotin LCNASGAHALQ—1306.59 amu; SEQ ID NO: 26) were also synthesized and used in the epitope studies. (Table 9)

Solubilizing Peptides:

All peptides were solubilized in PBS. The pH of the solution was adjusted with 0.01N HCl or 0.01N NaOH if any difficulty in solubility was observed. The peptide was stored in stock solutions (1000 nM) at −20° C.

Coating the Peptides on an ELISA Plate:

Peptide solutions were diluted 1-in-100 with Hank's buffered saline solution (HBSS) containing 0.5% formaldehyde. 100 μL of diluted peptide solution was distributed to each well in a 96-well plate. The plates were incubated at room temperature for 1 hour. The supernatant was removed and the plates were placed uncovered in a 37° C. incubator for 16-18 hours. The peptide-coated plates were placed in plastic bags and stored at 2-8° C. until required.

Alternatively, the peptides were diluted in carbonate/bicarbonate buffer pH 9.6 and coated on the plates. All the other steps with the exception of a change in the coating buffer were the same.

Following overnight incubation of the peptide-coated plates, 300 μL of wash buffer (PBS containing 0.5% Tween20) was manually added to each plate, with the help of a repeater pipette equipped with an 8-channel adaptor. The contents of the plates were discarded; the plates were inverted and patted on 3-4 inches of paper towel to remove excess liquid. The above steps were repeated two more times.

Blocking:

The peptide-coated plates were blocked with 300 μL/well with blocking buffer (PBS containing 1% BSA). The plates were incubated for 30-60 minutes at room temperature. The block buffer was discarded after the incubation.

Binding of VB1-213 to the Peptide-Coated ELISA Plates:

Aliquots equivalent to 75 μg/mL of VB1-213 were added to each of the wells and incubated at 37° C. for two hours. The plates were washed as previously described with the wash buffer (PBS containing 0.5% Tween 20). The plates were incubated with 1:6000 dilution of anti-human IgG-HRP for one hour at room temperature. The plates were washed as previously described. 100 μL of TMB substrate (TMB peroxidase substrate KPL cat#50-76-00) was added to each well and incubated for 5-10 minutes in the dark. The reaction was terminated by adding 100 μL of 1M phosphoric acid to each well. The optical density was measured at 450 nm using an ELISA plate reader.

Results

Figure 21:
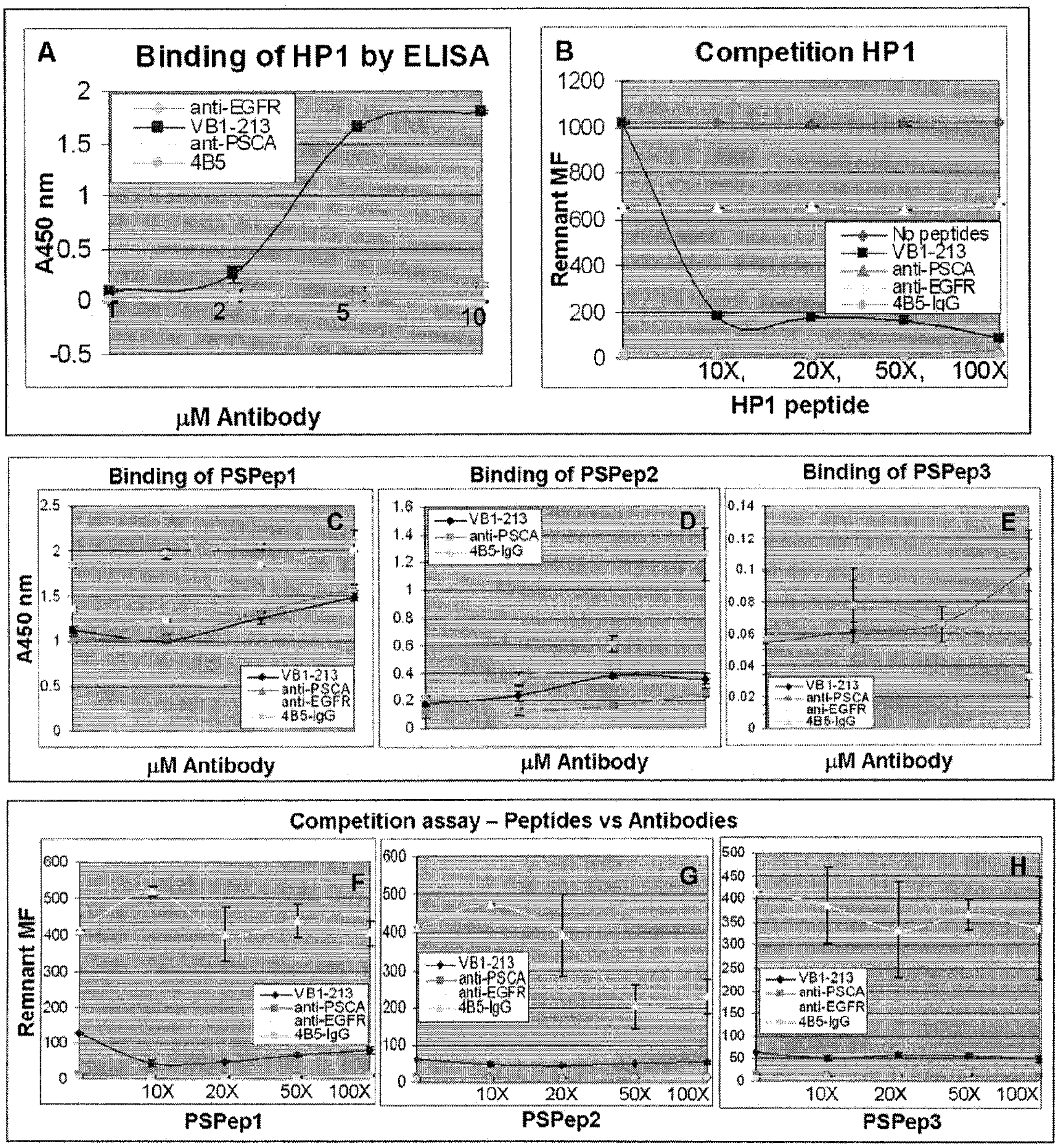
FIG. 21 shows VB1-213 binding to synthetic peptides derived from PSCA sequences in comparison with a unrelated antibody (anti-EGFR) and with commercially available antibodies to PSCA by ELISA and competition assay. 10 mM concentration of the appropriate peptide was coated on each well of the 96-well plate. The peptide concentration in each experiment was confirmed by measuring biotin levels prior to the assay. VB1-213 bound very strongly to HP-1 but the other three antibodies, namely, 4B5-IgG (isotype-matched control), anti-EGFR (unrelated antibody) and commercial anti-PSCA showed no binding to peptide HP1 (A).

Except for VB1-213 which bound very strongly to HP1 (at 10 μg/m L) with an OD of 1.8, no other antibody showed any binding whatsoever to HP1 (FIG. 21A). Furthermore, VB1-213 demonstrated no significant binding to PSPep1, PSPep2 or PSPep3 (FIGS. 21 C, D and E). The results are summarized in Table 9. Both the isotope-matched control, 4B5-IgG and the unrelated antibody, anti-EGFR showed very high level of background binding. 4B5-IgG showed preferential binding to all peptides, except HP1.

Example 9

Epitope Mapping—Competition Experiments

Methods and Reagents
Growth and Maintenance of Tumor Cell Lines:

Cell lines that are VB1-213-positive, i.e., DU-145, were cultured and maintained according to ATCC guidelines.

Synthetic Peptides:

All peptides were solubilized in PBS and stored at 1.428 mM (2 mg/mL) and as 100 μM solutions at −20° C.

Competition Assay:

VB1-213 (75 mg/mL)—0.5 μM concentration, was used as the non-competed control. Molar excesses, i.e., 20×, 40×, 100× and 200× of peptides were used to compete with VB1-213. The peptides/VB1-213 mixtures were incubated on ice for 10 minutes prior to binding by flow. Anti-PSCA was used as an antigen-matched control, 4B5-IgG was used as the isotype-matched control and anti-EGFR was used as the unrelated antibody. These three antibodies were processed exactly the same as VB1-213.

Binding of VB1-213:

The binding of VB1-213, along with the anti-PSCA, anti-EGFR and 4B5-IgG antibodies to DU-145 cells was assessed by flow cytometry; and was performed according to the optimized protocol previously described in Example 5. Cells treated with peptides and those that were untreated were processed similarly.

Results

As shown in FIG. 21B, HP1 competed 92% of VB1-213 binding. No significant displacement of binding was observed with the negative peptide, PSPep3. HP1 failed to inhibit the binding of anti-EGFR, 4B5-IgG or anti-PSCA. FIGS. 21F, 21G and 21H demonstrate the failure of PSPep1, PSPep2 and PSpep3 to inhibit the binding of all of the antibodies screened in the study.

Results from synthetic peptide studies for VB1-213, anti-EGFR (unrelated antibody), 4B5-IgG (isotype-matched control) and anti-PSCA (commercially available antibody) is summarized in the Table 10. The results are clearly indicative of PSCA as the cell surface antigen and the HP1, (YSCKAQVSNED) as an epitope for VB1-213. The binding and competing profiles of PSPep1, PSPep2 and PSPep3 are characteristic of non-specific interactions.

Example 10

Cytotoxicity of VB6-213 Immunotoxin

Molecular Engineering of VB6-213-Fab-PE Engineering

The VB6-213-Fab-PE construct was engineered by creating the EcoRI-PelB-$V_H$213-ApaI and SfiI-6×His-$V_L$213-$C_L$-XhoI fragments which were inserted into the EcoRI-ApaI-$C_H$-PE-PelB-SfiI-XhoI/pING3302 plasmid. The engineered fragments were cloned directly into the pING3302 Xoma vector under the control of the arabinose-inducible araBAD promoter. Upon induction by L-(+) arabinose, the presence of the PelB leader sequence, adjacent to the gene of interest resulted in the secretion of the protein into the culture supernatant. A histidine affinity tag, placed at the N-terminal end of the $V_L$-$C_L$ domain permitted purification using a $Ni^{2+}$-chelating capture method.

The EcoRI-PelB-$V_H$213-ApaI fragment was assembled by the Splice Overlapping Extension Polymerase Chain Reaction method using the PelB and VB1-213-$V_H$ DNA plasmids as templates and the following primers:

```
                                          (SEQ ID NO: 27)
5' PelB: 5' GAA TTC CCT GCA GGT CTA TGG AAC GAT
AAA TGC

                                          (SEQ ID NO: 28)
3' PelB-VH213: 5' CCC AGA CTC CAA CAG CTG
CAC CTC CGC CAT GGC TGG TTG GGC AGC GAG

                                          (SEQ ID NO: 29)
5' PelB-VH213: 5' ATG GCG GAG GTG CAG CTG
TTG GAG TCT GGG GGA GGC

                                          (SEQ ID NO: 30)
3' VH213-ApaI: 5' CGA TGG GCC CTT GGT GGA
GGC TGC GGA'GAC GGT GAC CGT GGT
```

A two-step Splice Overlapping Extension PCR approach was undertaken using all 4 primers listed above to construct and amplify EcoRI-PelB-$V_H$213-ApaI. The EcoRI and ApaI restriction sites (bolded) were added to facilitate the cloning of PelB-$V_H$213 into the EcoRI-ApaI-$C_H$-PE-PelB-SfiI-XhoI/3302 vector. The PCR reaction included a 50 μL reaction volume containing:

| | |
|---|---|
| 10X PCR buffer | 5 μL |
| 2 mM dNTPs | 5 μL |
| 50 mM $MgCl_2$ | 2 μL |
| Primer 5' | 20 pmol |
| Primer 3' | 20 pmol |
| Taq DNA Polymerase | 2.5 U |
| DNA template | 50 ng |

The cycling conditions for PCR were: 94° C. for 1 min., 62° C. for 1 min., and 72° C. for 1.5 min., for a total of 20 cycles followed by a final extension of 10 min. at 72° C.

Step 1

The first PCR reaction involved primers 1 and 2 and the PelB template. This yielded fragment containing in the 5' end the PelB region with a EcoRI restriction site, and in the 3' end the PelB leader signal.

Figure 22:
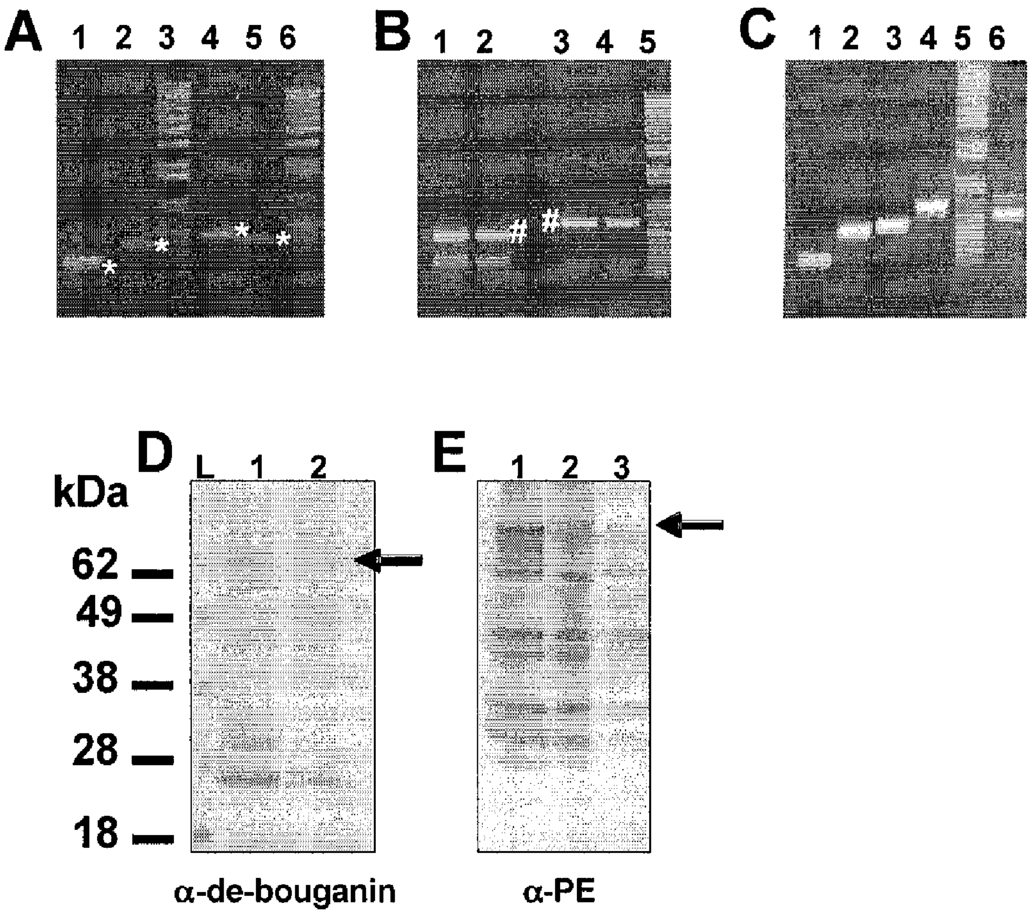
FIG. 22 shows agarose gels used to verify the fragments created by PCR reactions and used for the engineering of a VB1-213 based immunotoxin and Western blots used to verify the production of the assembled immunotoxin by *E-coli*. The DNA was detected using ethidium bromide under a UV lamp. A and B) SOE-PCR VB6-213-Fab-PE. A) The first PCR reaction of the EcoRI-PelB-$V_H$213, $V_H$213-ApaI, SfiI-6×His-$V_L$213 and $C_L$-XhoI fragments were loaded on lane 1, 2, 4 and 5 respectively. The 1 Kb ladder was loaded on lanes 3 and 6. The stars indicate the PCR product at the expected size. B) The fragments of the first PCR reaction were used to generate the fragment EcoRI-PelB-$V_H$213-ApaI (FIG. 22B, lane 1 and 2) and SfiI-6×His-$V_L$213-$C_L$~XhoI (lanes 3 and 4) at the predicted size as indicated by the # symbol. C) SOE-PCR VB6-213-$C_L$-de-bouganin. The first PCR reaction of the EcoRI-PelB-6×His-$V_H$213, $V_H$213-ApaI, ApaI-$C_H$-PelB-SfiI and SfiI-$V_L$213-$C_L$-XhoI fragments, lane 1, 2, 3 and 4, respectively were analyzed on agarose gel. Lane 5 is the 1 kB ladder. The EcoRI-PelB-6×His-$V_H$213-ApaI fragment was generated from the first PCR reaction (FIG. 22C, lane 6). D) Western blot of VB6-213-$C_L$-de-bouganin. Supernatant of VB6-213-$C_L$-de-bouganin (lane 2) and VB6-170 clone (lane 1) were loaded under non-reducing conditions on a SDS-PAGE gel and immunoblotted with a rabbit anti-bouganin antibody followed by a goat anti-rabbit HRP. The arrow indicates the full-length protein migrating approximately at 65 kDa. L is the ladder. E) Western blot of VB6-213-Fab-PE. Lane 1 corresponds to VB6-011-Fab-PE supernatant, lane 2 to VB6-213-Fab-PE and lane 3 to VB6-213-Fab-PE. The arrow indicates the full-length protein migrating approximately at 75 kDa.

In a separate PCR reaction, primers 3 and 4 along with the 213 $V_H$ template were used to amplify $V_H$213 flanked at the 5' end by the PelB leader signal and the start of the $V_H$ domain and at the 3' end 21 nucleotides of the $C_H$ domain with ApaI site. (FIG. 22A)

Step 2

In the next PCR reaction, primers 1 and 4 were used with 1 μL from each PCR product to produce EcoRI-PelB-$V_H$213-ApaI. (FIG. 22B)

The SfiI-6×His-$V_L$213-$C_L$ fragment was assembled by the Splice Overlapping Extension Polymerase Chain Reaction method using VB6-213 and VB1-213 light chain DNA plasmids as templates and the following primers:

```
                                          (SEQ ID NO: 31)
5' SfiI-6xHis-VL-213: 5' CTC GCG GCC CAA CCG GCC
ATG GCG CAT CAC CAT CAC CAT CAC TCC TAT GAG CTG
ACT CAG CCA CCC
```

-continued

```
                                          (SEQ ID NO: 32)
3' VL-CL: 5' GAC CGA GGG GGC AGC CTT GGG CTG ACT
TAG GAC GGT CAG CTT GGT CCC

                                          (SEQ ID NO: 33)
5' Lambda constant: 5' CAG CCC AAG GCT GCC CCC
TCG GTC ACT CTG TTC

                                          (SEQ ID NO: 34)
3' End-XhoI lambda constant: 5' CTC GAG TCA CTA
TGA ACA TTC TGT AGG GGC CAC TGT
```

A two-step Splice Overlapping Extension PCR approach was undertaken using all 4 primers listed above to construct and amplify SfiI-6×His-$V_L$213-$C_L$~XhoI. The SfiI and XhoI restriction sites (bolded) were added to facilitate the cloning of SfiI-6×His-$V_L$213-$C_L$-XhoI into the EcoRI-ApaI-$C_H$-PE-PelB-SfiI-XhoI/3302 vector.

Step 1

In the first PCR reaction, primers 1 and 2 along with the VB1-213 light chain template were used to amplify SfiI-6×His-$V_L$213 flanked at the 5' end with the SfiI restriction site and the 6×His and in the 3' end the first 21 nucleotides of the $C_L$ domain. (FIG. 22A)

The second PCR reaction was performed with primers 3 and 4 along with $C_L$ template and yielded the lambda constant light chain containing in the 3' end the XhoI restriction site.

Step 2

In the next PCR reaction, primers 1 and 4 were used with 1 μL from each PCR product to produce SfiI-6×His-$V_L$213-$C_L$~XhoI fragment. (FIG. 22B)

Once the sequences were verified, the PelB-$V_H$213 fragment was digested with the EcoRI and ApaI restriction enzymes and ligated into the EcoRI-ApaI-$C_H$-PE-PelB-SfiI-XhoI/3302 vector pre-digested with same enzymes. 10F competent cells were transformed with the ligation reaction and plated onto LB-agar plates supplemented with tetracycline. The presence of the insert was confirmed by restriction mapping of the plasmid PelB-$V_H$213-$C_H$-PE-PelB-SfiI-XhoI/3302. The SfiI-6×His-$V_L$213-$C_L$~XhoI fragment was then digested with the SfiI and XhoI restriction enzymes and ligated into PelB-$V_H$213-$C_H$-PE-PelB-SfiI-XhoI/3302 vector pre-digested with same enzymes to engineer VB6-213-Fab-PE (FIG. 24, SEQ ID NO: 43 and FIG. 30 SEQ ID NO 50 and 51). Once the presence of the correct insert was confirmed by restriction mapping, the construct was transformed into *E. coli* E104 cells for small-scale expression studies.

Molecular Engineering of VB6-213-$C_L$-be-bouganin

The VB6-213-$C_L$-de-bouganin construct was engineered by creating three fragments, EcoRI-PelB-6×His-$V_H$213-ApaI, ApaI-$C_H$-PelB-SfiI and SfiI-$V_L$213-$C_L$-XhoI fragments which were inserted in the VB6-213-$C_L$-de-bouganin/pING3302 plasmid. The conserved SmaI restriction site in the constant light chain of VB6-213-$C_L$-de-bouganin was used for sub-cloning.

The EcoRI-PelB-6×His-$V_H$213-ApaI was assembled by SOE-PCR as described previously except primers 2 and 3 were replaced in order to introduce the 6×His tag:

```
                                          (SEQ ID NO: 35)
3' PelB6xHis-VH213: 5' GTG ATG GTG ATG GTG ATG CGC
CAT GGC TGG TTG GGC AGC GAG

                                          (SEQ ID NO: 36)
5' PelB-VH213: 5' CAT CAC CAT CAC CAT CAC GAG GTG
CAG CTG TTG GAG TCT GGG
```

The ApaI-$C_H$-PelB-SfiI was created by one step PCR using the following primers:

```
                                    (SEQ ID NO: 37)
5' ApaI-CH: 5' GCC TCC ACC AAG GGC CCA TCG GTC
TTC CCC

                                    (SEQ ID NO: 38)
3' PelB-SfiI: 5' CGC CAT GGC CGG TTG GGC CGC GAG
TAA TAA CAA
```

The SfiI-$V_L$213-$C_L$-XhoI fragment was also created with one step PCR using the following primers:

```
                                    (SEQ ID NO: 39)
5' SfiI-VL213: 5' GCG GCC CAA CCG GCC ATG GCG TCC
TAT GAG CTG ACT CAG CCA CCCTCA GTG

                                    (SEQ ID NO: 40)
3' End-XhoI lambda constant: 5' CTC GAG TCA CTA
TGA ACA TTC TGT AGG GGC CAC TGT
```

Once the sequences were verified, (FIG. 22C) the SfiI-$V_L$213-$C_L$-XhoI fragment was digested with the EcoRI (from the pcR2.1 vector) and SmaI restriction enzymes and ligated into the VB6-213-$C_L$-de-bouganin/3302 vector pre-digested with same enzymes. 10F competent cells were transformed with the ligation reaction and plated onto LB-agar plates supplemented with tetracycline. This step created the following insert EcoRI-SfiI-$V_L$213-$C_L$-de-bouganin in the 3302 vector. The 3302 vector was then digested with EcoRI and SfiI restriction and ligated simultaneously with the EcoRI-PelB-6xHis-$V_H$213-ApaI, and ApaI-$C_H$-PelB-SfiI inserts digested with EcoRI/ApaI and ApaI/SfiI, respectively to create VB6-213-$C_L$-de-bouganin. (FIG. 23, SEQ ID NO: 42 and FIG. 29 SEQ ID NO: 48 and 49)

Small-Scale Expression of VB6-213-Fab-PE and VB6-213-$C_L$-de-bouganin

An over-night culture of VB6-213-Fab-PE/E104 and VB6-213-$C_L$-de-bouganin/E104 cells (1% innoculum at $OD_{600}$=3) was used to inoculate 30 mL of TB medium in a 250 mL shake flask. The culture was incubated at 37° C. and shaken at 225 rpm until an optical density ($OD_{600}$) of 2 was achieved. Expression was then induced with 0.1% L-(+) arabinose and the culture was further incubated at 25° C. At 16 hours post-induction, the culture supernatant and pellet were separated by centrifugation at 14,000 rpm for 5 min. An aliquot of the VB6-213-Fab-PE and VB6-213-$C_L$-de-bouganin supernatants, 16 mL, were loaded on a SDS-PAGE acrylamide gel under non-reducing conditions and analyzed by Western blot using a rabbit anti-PE antibody and a rabbit anti-bouganin, respectively followed by a goat anti-rabbit coupled to HRP to confirm the identity and size of the recombinant protein. E104 cells harboring the VB6-213-Fab-PE/3302 plasmid or VB6-011-Fab-PE or VB6-170-$C_L$-de-bouganin were also induced using the same conditions and the supernatants containing soluble protein were used as a positive control on Western blot. See FIGS. 22D and E.

Purification of VB6-213-$C_L$-de-bouganin

One vial from the Master Cell Bank is thawed and used to inoculate 250 mL of 2xYT medium supplemented with 25 mg/L tetracycline in a 2.0 L Erlenmeyer flask. This culture is incubated at 37.0° C. and shaken at 225 rpm for 6-7 hours to attain an $OD_{600}$ of 2.0+/−0.5. Subsequently, 15 L fermentor, containing 13 L TB medium, is inoculated with 1% inoculum of the seed. The culture is grown at 25° C. and when an $OD_{600}$ of 20 is achieved, expression is induced with continuous pulse of L-(+) arabinose. At 30 hours post-induction, the bacterial culture is centrifuged and the supernatant collected and concentrated 20 to 30 times using a 30 kDa mwco membrane. The concentrated supernatant containing VB6-213 is diafiltered against a solution of 20 mM $NaPO_4$ pH 6.9. The sample is then loaded onto CM-sepharose column equilibrated with 20 mM $NaPO_4$ pH 6.9. The column is washed with 20 mM $NaPO_4$, 25 mM NaCl pH 6.9 and bound proteins are eluted with 20 mM $NaPO_4$, 150 mM NaCl pH 7.5. The eluate of the CM-sepharose column is then applied onto a Nickel-chelating affinity column pre-charged with 0.1M $NiCl_2$ in water. The column is then washed with three successive buffers starting with 20 mM $NaPO_4$, 150 mM NaCl, 0.25% triton-$X_{100}$ pH 7.5, followed with 20 mM $NaPO_4$, 150 mM NaCl pH 7.5 and finally with 20 mM $NaPO_4$, 150 mM NaCl, 10 mM imidazole pH 7.5. The bound material is eluted from the column using 20 mM $NaPO_4$, 250 mM Imidazole, pH 7.2. The eluate is applied onto a SEC column equilibrated with 20 mM $NaPO_4$, 150 mM NaCl pH 7.5 and 10 mL fractions collected. All fractions are analyzed on a SDS-PAGE gel and stained with Coomassie blue. Fractions containing intact product are pooled and concentrated using centriplus concentrator, sterile filtered, aliquoted and stored at −20° C.

Detection of VB6-213-$C_L$-de-bouganin Binding by Flow Cytometry

Human prostate DU-145 and human T-cell Daudi cell lines are grown in their respective media as per ATCC protocols. Cells are harvested at 30 to 40% confluency with viability greater than 90%. DU-145 and Daudi are used as positive and negative cell lines, respectively.

The biological activity of VB6-213 is be determined by flow cytometry and VB1-213 is used as a positive control. Briefly, VB6-213 and VB1-213 are incubated with $0.45\times10^6$ tumor cells for 1.5 hours on ice. After washing, cell surface bound VB6-213 and VB1-213 is detected with rabbit anti-de-bouganin and biotinylated goat anti-human H&L chain, respectively for an hour on ice. The cells are washed and incubated with FITC-conjugated anti-rabbit IgG or streptavidin-FITC for 30 minutes on ice. Subsequently, the cells are washed, resuspended in PBS 5% FCS containing propidium iodide for assessment of Fab binding by flow cytometry.

Cytotoxicity of VB6-213-$C_L$-de-bouganin

The cytotoxicity of VB6-213 is measured by an MTS assay. Briefly, DU-145 and Daudi cells are seeded at 1000 cells per well and incubated at 37° C. for 3 hours. Subsequently, equimolar concentrations of VB6-213 and bouganin are added to the cells and after 5 days, the cell viability is determined.

Example 11

Measurement of Anti-Epitope-Peptide Antibody in Serum

Antibodies to an antigen disclosed herein may be present in the sera/plasma of a subject, indicating the possibility of expression or overexpression of one or more antigen of the invention and, thus the presence of cancer cells. In one example, a sample of the sera/plasma from a subject is tested by ELISA techniques as described below and adapted from previously described (M. Tanaka et al., *Oncol Rep* 18, 161 (2007) to determine the presence and titer of anti-peptide-epitope antibodies in the subject's sera. In another example, the sera sample may be tested by flow cytometry using, for example, peptide-loaded beads. Peptide-loaded carboxylate beads can be prepared as follows:

The peptides of interest, that can include the epitopes disclosed herein YSCKAQVSN (SEQ ID NO: 41), YSCK- AQYSNRD (SEQ ID NO: 111) and YSCKAQVSNED (SEQ ID NO:23) are synthesized using known methods. The peptides are dissolved in dimethyl sulfoxide (DMSO), stored at −80° C., and diluted with saline just before use. The peptides are coupled with carboxylate beads (xMAP; Luminex Corporation, Austin, Tex., USA) according to the modified manufacturer's instructions. One hundred ml of the xMAP beads are washed with 0.1 M MES buffer, pH 7.0 followed by mixing with 1000 peptide (1 mg/ml in 0.1 M MES buffer. pH 7.0). The peptide-loaded beads are then incubated with EDC (1 mg/ml) at room temperature for 30 min in darkness, then incubated twice more under the same conditions, and the beads are washed with 0.05% Tween-20 PBS (PBST). Finally, the beads are treated with 2-aminoethanol for 15 min at room temperature in darkness, then washed twice and resuspended with 1 ml 0.05% $NaN_3$ in Block Ace. The beads can be prepared to present only one type (sequence) of peptide or two or more types of peptide. For instance, a batch of beads can be prepared using only one peptide epitope of the invention or multiple peptide epitopes of the invention. Likewise for non-binding peptides, beads can be prepared with only one such peptide sequence or several different non-binding sequences.

The presence of peptide-specific immunoglobulin levels in the sample can then be measured by flow cytometry. An aliquot of the subject's sample is incubated with 170 μl of the peptide-coded beads for 2 h at room temperature in a 96-well filter plate on a plate shaker. After incubation, the plate is washed using a vacuum manifold apparatus and incubated with 100 μl biotinylated goat anti-human IgG (gamma chain-specific) for 1 h at room temperature on a plate shaker. The plate is then washed, 100 μl streptavidin-PE are added to the wells, and the plate is incubated for 40 min at room temperature on a plate shaker. The bound beads are washed three times followed by the addition of 100 μl PBST into each well, and the plate is then placed for 3 min on a plate shaker. The PE fluorescence is measured with an excitation wavelength of 488 nm and an emission wavelength of 575 nm using an ELISA plate reader.

Alternatively, the subject plasma or serum sample can be tested using ELISA plates on which the peptides have been immobilized. For the preparation of the peptide immobilized ELISA plate for the antibody absorption test, the peptides (SEQ ID NO: 23, 41 and 111) are diluted in 0.1 M carbonate buffer containing a chemical cross-linker, disuccinimidyl suberate (Pierce). ELISA plates are coated overnight at 4° C. with the target peptides (20 μg/well). The wells are rinsed three times with 0.05% PEST. The plates are blocked overnight at 4° C. with Block Ace. To test the specificity of the anti-peptide IgG, 100 μl/well of plasma samples (1:1000 dilution with 0.05% PBST) are absorbed with the immobilized peptide (20 μg/well) in wells kept for 2 h at room temperature. The absorption is repeated three times, and then the level of the peptide-specific immunoglobulin in the resultant supernatant is measured.

Example 12

Ability of Epitope-Bearing Peptide to Induce Cytotoxic T-Lymphocytes

Peptides derived from PSCA bearing a different epitopes have previously been shown to be immunogenic and to induce cytotoxic T-lymphocytes from the peripheral blood mononuclear cells (PBMC) (US2002000498075). Antibodies corresponding to different immunogenic peptides from wild-type HnRNPG have been isolated from dogs with systemic lupus erythematosus (Soulard et al, 2002).

The epitope-bearing peptide (SEQ ID NO: 23, 41, and 111) is used in T-cell proliferation assays with PBMCs (peripheral blood mononuclear cells) from healthy donors. PBMC samples from approximately 20 donors are used to get an adequate coverage of MHC class II allotypes.

Buffy coats from human blood stored for less than 12 hours are obtained from the National Blood Service (Addenbrooks Hospital, Cambridge, UK). Ficoll-paque is obtained from Amersham Pharmacia Biotech (Amersham, UK). Serum free AIM V media for the culture of primary human lymphocytes and containing L-glutamine, 50 ug/ml streptomycin, 10 ug/ml gentomycin and 0.1% human serum albumin is from Gibco-BRL (Paisley, UK).

Erythrocytes and leukocytes are separated from plasma and platelets by gentle centrifugation of buffy coats. The top phase (containing plasma and platelets) is removed and discarded. Erythrocytes and leukocytes are diluted 1:1 in phosphate buffered saline (PBS) before layering onto 15 ml ficollpaque (Amersham Pharmacia, Amersham UK). Centrifugation is done according to the manufacturers recommended conditions and PBMCs are harvested from the serum+PBS/ficoll paque interface. PBMCs are mixed with PBS (1:1) and collected by centrifugation. The supernatant is removed and discarded and the PBMC pellet resuspended in 50 ml PBS. Cells are again pelleted by centrifugation and the PBS supernatant discarded. Cells are resuspended using 50 ml AIM V media and at this point counted and viability assessed using trypan blue dye exclusion. Cells are again collected by centrifugation and the supernatant discarded. Cells are resuspended for cryogenic storage at a density of $3\times10^7$ per ml. The storage medium is 90% (v/v) heat inactivated AB human serum (Sigma, Poole, UK) and 10% (v/v) DMSO (Sigma, Poole, UK). Cells are transferred to a regulated freezing container (Sigma) and placed at −70° C. overnight. When required for use, cells are thawed rapidly in a water bath at 37° C. before transferring to 10 ml pre-warmed AIM V medium.

Synthetic peptides such as those for epitopes YSCKAQVSN (SEQ ID NO: 41), YSCKAQYSNRD (SEQ ID NO: 111) and YSCKAQVSNED (SEQ ID NO:23) are prepared. The peptides are dissolved in DMSO to a final concentration of 10 mM, these stock solutions are then diluted 1/500 in AIM V media (final concentration 20 uM). Peptides are added to a flat bottom 96 well plate to give a final concentration of 1 and 5 uM in 100 μl.

The viability of thawed PBMCs is assessed by trypan blue dye exclusion, cells are then resuspended at a density of $2\times10^6$ cells/ml, and 100 μl ($2\times10^5$ PBMC/well) is transferred to each well containing peptides. Triplicate well cultures are assayed at each peptide concentration. Plates are incubated for 7 days in a humidified atmosphere of 5% $CO_2$ at 37° C. Proliferation is assessed by $^3$H-thymidine ($^3$H-Thy; Amersham-Pharmacia, Amersham, UK) incorporation. Cells are pulsed for 18-21 hours with 1 uCi $^3$H-Thy/well before harvesting onto filter mats. CPM values are determined using a Wallac microplate beta top plate counter (Perkin Elmer). Stimulation indices (S.I.) are calculated as the amount of $^3$H incorporated, divided by the amount of $^3$H incorporated in mock-stimulated control cells.

Example 13

Ability of VB1-213 to Induce Antibody Dependent Cell-Mediated Cytotoxicity (ADCC)

PBMC is enriched by Ficoll-hypaque gradient centrifugation, washed in 1×PBS and counted. Two approaches can be used to measure cytotoxicity: flow cytometry and an ELISA assay. Briefly, with the flow cytometry approach, target tumor cells, DU-145 are incubated with 0.2 μM of calcein for 25 minutes at 37° C. After one wash, DU-145 cells are mixed with PMBC at a ratio of 1:20 in presence of various concentrations of antibody ranging from 10 to 100 μg/mL for 3.5 hours at 37° C. A solution of propidium iodide at a final concentration of 1 μg/mL are added and analyzed using a FACSCalibur. DU-145 cells treated with 0.1% Triton X-100 and the amount of calcein released as a result of this treatment is considered to represent the maximal % of lysis. The percentage of cytotoxicity is determined by the ratio of target tumor cells with no calcein (no green color) and PI stained divided the maximal lysis (triton-X treated). For the ELISA assay, target tumor cells are seeded on a 96-well plate in presence of PBMC and antibody with the same ratio as previously described. The measurement of, for example, lactate dehydrogenase protein released in the supernatant from the damage cell by ELISA quantifies the cytotoxic activity of the antibody. The IgG 4B5 which does not bind DU-145 is used as a negative control.

Example 14

Tumor Associated Expression of HnRNPG and Localization as a Tumor Diagnostic Wild type HnRNPG is expressed in the cell nucleus. However, as described in Example 1 the inventors have isolated a variant of this protein from membrane fractions of tumor cells and have localized it as associated with the intracellular side of the membrane. This aberrant cellular localization of the variant can therefore be used as a diagnostic method for cancer. There are several methods known in the art that can be used to detect the cellular localization of HnRNPG or variant HnRNPG, including western blotting, immunohistochemistry or flow cytometry.

Example 15

Detection of Genomic DNA Sequence as an Indication of Cancer

The gene coding for the human Mammalian HnRNPG protein has been located to chromosome X q26.3. The gene sequence for the cancer associated variant can be determined using gene sequencing techniques known in the art such as exon-specific PCR amplification or direct DNA sequencing initiating from primers to the known sequence.

Once the sequence of the mutated gene is identified, then diagnostic tests based on its detection can be used to evaluate patients. For example, DNA chip arrays can be created by attaching oligonucleotides corresponding to the sense and anti-sense sequences of both wild type and the mutated gene. Genomic DNA can be isolated from the peripheral whole blood or from tumor tissues The gene of interest is then amplified using PCR with primers corresponding both to the wild type sequence and to the expected mutations and labeled with an appropriate probe (usually fluorescent). The DNA is then hybridized to the oligonucleotides on the chip and the pattern of fluorescence determined with a fluorescent reader. By comparing the pattern of fluorescence to a map of the known locations of the oligonucleotides sequences the sequence of the patient's gene with can be established as either wild type or variant. (Cooper et al 2004) Arrays for common mutations in the p53 gene (Affymetrix) among others are already commercially available and custom array services are also available.

Example 16

The binding of VB1-213 in conjunction with aldefluor (ALDH1) staining was used to assess cancer stem cell reactivity. In general, tumor cells with high ALDH staining represent the cancer stem cell fraction which is capable of self-renewal and of generating tumors in xenograft implants. High ALDH1 activity is believed to impart resistance to certain chemotherapeutics leading to the outgrowth of new tumors and the subsequent relapse in patients (120, 121). Two color flow cytometry was used to measure VB1-213 binding to the ALDH1+ cells of the ovarian cell line C-33-A and prostate tumor cell line DU-145. VB1-213 binding to the ALDH1+ C-33-A and DU-145 subpopulation highlights its potential utility against cancer stem cells.

Experimental design: Briefly, $2\times10^5$ cells were incubated with the aldefluor reagent for 30 minutes at 37° C. Then, cells were washed and incubated at 4° C. in presence of 25 μg/mL of VB1-213 for 2 hours. VB1-213 bound to cells was detected using a biotinylated goat anti-human H&L followed by streptavidin Cy5. VB1-4B5, a human IgG anti-Id was used as a negative control. As well, the specificity of the aldefluor staining was demonstrated in presence of DEAB, an inhibitor of the reaction.

Figure 33:
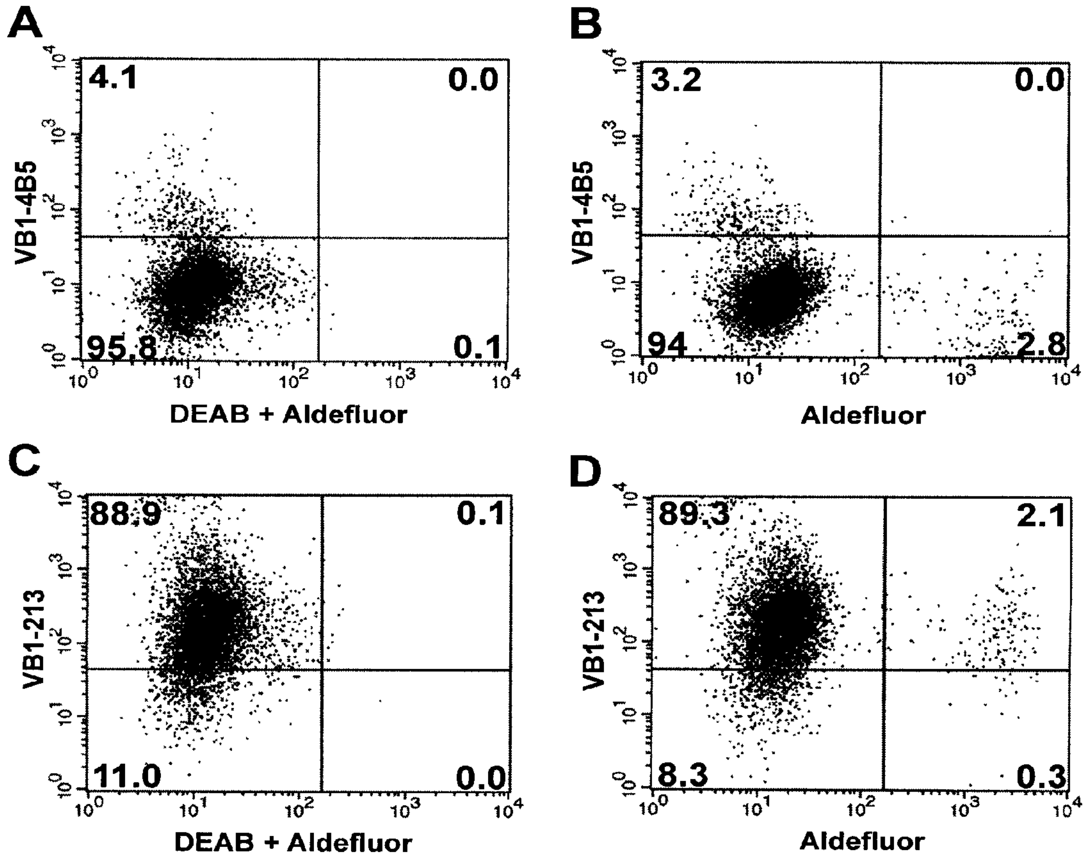
FIG. 33 is the flow cytometry results showing the binding of VB1-213 or the control antibody VB1-4B5 in conjunction to aldefluor on C33-A cells
Figure 34:
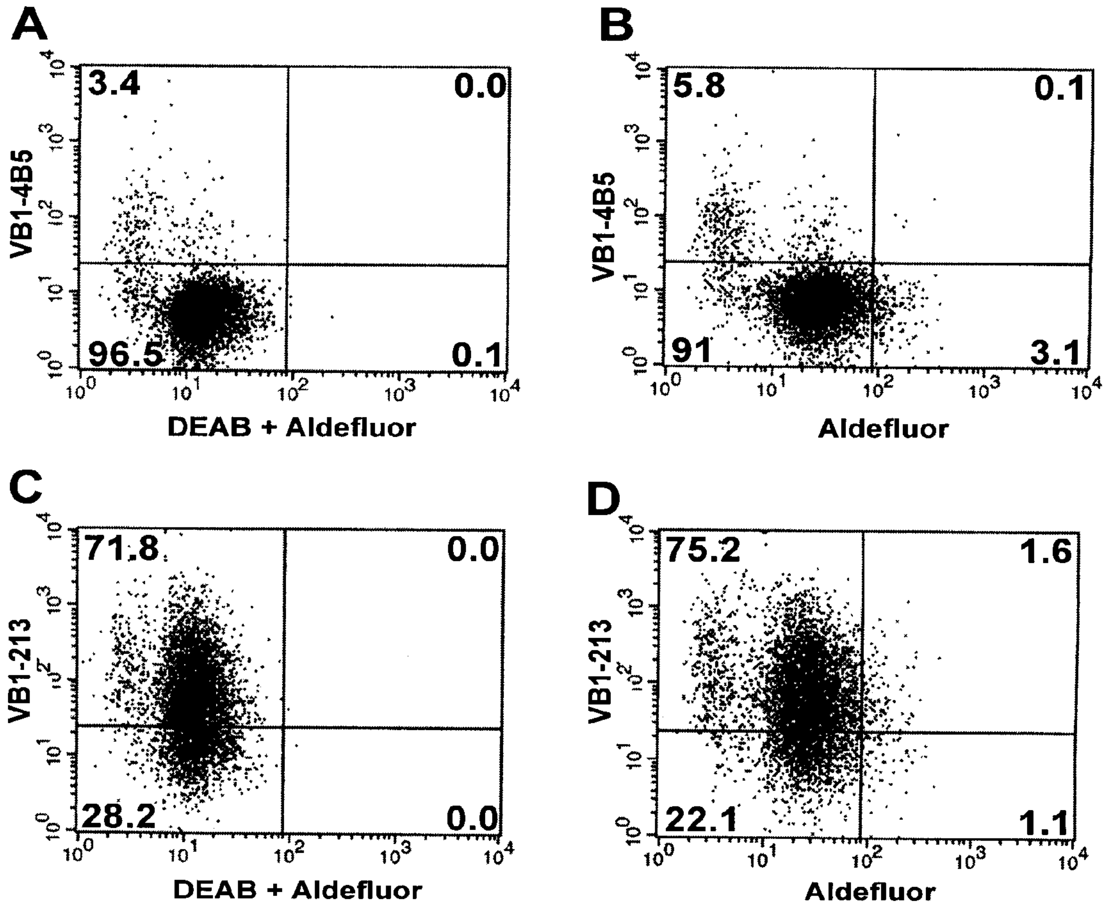
FIG. 34 is the flow cytometry results showing the binding of VB1-213 or the control antibody VB1-4B5 in conjunction to aldefluor on DU-145 cells

Result: The analysis of the data showed that 2.8 and 3.1% of cancer stem cells are detected in C-33-A (FIG. 33) and DU-145 (FIG. 33), respectively (Lower right, FIGS. 33B and 34B). As well, VB1-213 binds C-33-A and DU-145 cells with 90 and 75% of the cells, respectively shifting to the upper left quadrant (FIGS. 33C and 34C). FIGS. 33D and 34D showed the ALDH1+ cancer stem cells of C33-A (2.1%) and DU-145 (1.6%) shifted to the upper right quadrant in presence of VB1-213. This data suggest that VB1-213 binds the cancer stem cell fraction.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

CDR Sequences.

| | L-chain | | H-chain | |
|---|---|---|---|---|
| CDR1 | SGNKLGDKYAC | SEQ ID NO: 7 | SYAMS | SEQ ID NO: 10 |
| CDR2 | QDSKRPS | SEQ ID NO: 8 | TISGRGVTTYYADSVKG | SEQ ID NO: 11 |
| CDR3 | QAWDNSTAV | SEQ ID NO: 9 | DRTRYYGMDV | SEQ ID NO: 12 |

TABLE 2

| Comparison of tumor cell surface binding amongst different clinical indications. | | | |
|---|---|---|---|
| Clinical Indication | Representative Tumor Cell lines | MF | Average MF$^2$ |
| Lung | A-549 | 92.85 | 80.47 |
| | NCI-H460 | 68.1 | |
| Prostate | DU-145$^{a,b,c}$ | 18.65 | 49.36 |
| | PC-3$^{a,b,d}$ | 37.25 | |
| | LNCaP$^{a,b,d}$ | 92.2 | |
| Melanoma | A-375 | 40.45 | 38.27 |
| | SK-MEL-28 | 36.1 | |
| Breast | MDA-MB-231 | 10 | 25.06 |
| | MDA-MB-231 | 31.8 | |
| | SK-BR3 | 33.4 | |

MF indicates the mean-fold increase in median fluorescence over the control antibody from two independent experiments.
[2]MF: Values indicate the mean calculated from the sum of the mean-fold increase in median fluorescence over the control antibody from all cell lines in each indication. A zero value indicates no measurable reactivity relative to the control antibody.
[a]Indicates orthotopic models offered by AntiCancer Inc.
[b]Indicates cell lines available as GFP (green fluorescent protein)-transfectants.
[c]Androgen-responsive.
[d]Androgen-unresponsive.

TABLE 3

| LD array of critical normal tissue for VB1-213. | | | | |
|---|---|---|---|---|
| Normal Tissue Type | Number of Samples | Samples with membrane staining | Score Range* | Percent of Tissue Stained |
| Brain | 4 | 0 | — | — |
| Colon | 4 | 0 | — | — |
| Heart | 5 | 0 | — | — |
| Kidney | 5 | 0 | — | — |
| Liver | 5 | 0 | — | — |
| Lung | 5 | 5 | 1-2+ | 20% |
| Pancreas | 5 | 1 | 1+ | 10% |
| Stomach | 4 | 0 | — | — |

*Scoring was evaluated on a 0-3+ scale, with 0 = no staining and trace being less than 1+ but greater than 0. Grades 1+ to 3+ represent increased intensity of staining, with 3+ being strong, dark brown staining. In general, a single specimen of 5 different patients was screened. Where fewer than 5 patients were screened indicates cores were either missing or were not representative of the tissue to be stained.
"Percentage of Tissue Stained" indicate the highest percentage of cells stained in the scored range.

TABLE 4

| HD tumor TMA for VB1-213. | | | | |
|---|---|---|---|---|
| Tumour Type | Number of Samples | Samples with membrane staining | Score Range* | Percent of Tumour Stained |
| Breast | 9 | 3 | 2+ | 20% |
| Colon | 8 | 0 | — | — |
| Liver | 9 | 4 | 1-2+ | 30% |
| Lung | 9 | 7 | 1+ | 20% |
| Skin | 9 | 3 | 1-3+ | 90% (also positive membrane staining with IgG control) |
| Prostate | 9 | 4 | 1+ | 20% |
| Ovary | 7 | 0 | — | — |
| Pancreas | 6 | 1 | 1+ | 10% |
| Kidney | 8 | 0 | — | — |
| Head & Neck | 8 | 2 | 1+ | 10% |

Scoring was evaluated on a 0-3+ scale, with 0 = no staining and trace being less than 1+ but greater than 0. Grades 1+ to 3+ represent increased intensity of staining, with 3+ being strong, dark brown staining. In general, 2 specimens of 8 different patients were screened. Where fewer than 9 samples (each sample is from a different patient) were screened, cores were either missing or were not representative of the tissue to be stained. Head & neck cancers included carcinomas of the trachea, larynx, tonsil, throat, soft palate, tongue, mouth and lips.
"Percent of Tumour Stained" indicate the highest percentage of cells stained in the scored range.

TABLE 5

| Increase in median fluorescence for VB1-213 over an isotype-matched control for each cell line used in the study. | | | |
|---|---|---|---|
| Tumor Type | Cell lines | MF increase | Average MF (per type) |
| Prostate | DU-145 | 90.6 | 90.6 |
| Ovarian | SKOV-3 | 84.1 | 84.1 |
| Breast | MB-435S | 53.7 | 46.3 |
| | SKBR-3 | 38.9 | |
| Pancreas | Panc-1 | 5.14 | 4.68 |
| | CFPAC-1 | 4.22 | |
| B-Lymphocyte | Daudi | 0.99 | 0.99 |

TABLE 6

| Peptides Recovered from Analysis of Band from 2D Gel Corresponding to HnRNPG | | | | |
|---|---|---|---|---|
| Start | End | Peptide mass | Description (Sequence) | SEQ ID NO: |
| 1 | 9 | 1002.1540 | MVEADRPGK.L | SEQ ID NO: 53 |
| 10 | 22 | 1435.5970 | K.LFIGGLNTETNEK.A | SEQ ID NO: 54 |
| 23 | 30 | 833.9830 | K.ALEAVFGK.Y | SEQ ID NO: 55 |
| 102 | 107 | 668.6610 | R.SRGPPR.G | SEQ ID NO: 56 |
| 173 | 180 | 737.7860 | R.SSSGMGGR.A | SEQ ID NO: 57 |
| 181 | 185 | 528.6090 | R.APVSR.G | SEQ ID NO: 58 |
| 186 | 195 | 1061.1190 | R.GRDSYGGPPR.R | SEQ ID NO59 |
| 197 | 202 | 697.7890 | R.EPLPSR.R | SEQ ID NO: 60 |
| 204 | 210 | 848.7298 | R.DVYLSPR.D | SEQ ID NO: 61 |
| 264 | 268 | 566.5710 | R.DGYGR.D | SEQ ID NO: 62 |
| 271 | 282 | 1340.3280 | R.DYSDHPSGGSYR.D | SEQ ID NO: 63 |
| 283 | 292 | 1177.1490 | R.DSYESYGNSR.S | SEQ ID NO: 64 |
| 293 | 298 | 627.6980 | R.SAPPTR.G | SEQ ID NO: 65 |
| 310 | 317 | 991.9670 | R.YDDYSSSR.D | SEQ ID NO: 66 |
| 318 | 324 | 710.7010 | R.DGYGGSR.D | SEQ ID NO: 67 |
| 325 | 331 | 800.7800 | R.DSYSSSR.S | SEQ ID NO: 68 |
| 332 | 339 | 883.9130 | R.SDLYSSGR.D | SEQ ID NO: 69 |
| 212 | 224 | 1481.9584 | R.DGYSCKAQYSNRD | SEQ ID NO: 70 |

TABLE 7

Recovered Peptides from In-solution Digests Corresponding to PSCA

| Start | End | Peptide mass | Description (Sequence) | SEQ ID NO: |
|---|---|---|---|---|
| 3 | 27 | 2534.1720 | K.AVLLALLMAGLALQPGTALLCYSCK.A | SEQ ID No: 18 |
| 28 | 52 | 2826.0800 | K.AQVSNEDCLQVENCTQLGEQCWTAR.I | SEQ ID No 19 |
| 55 | 64 | 1000.2470 | R.AVGLLTVISK.G | SEQ ID No 20 |
| 65 | 81 | 1866.0040 | K.GCSLNCVDDSQDYYVGK.K | SEQ ID No 21 |
| 83 | 123 | 4100.8210 | K.NITCCDTDLCNASGAHALQPAAAILALL PALGLLLWGPGQL. | SEQ ID No 22 |

TABLE 8

Recovered Peptides From In-solution Digests Corresponding to HnRNPG

| Start | End | Peptide mass | Description (Sequence) | SEQ ID NO: |
|---|---|---|---|---|
| 10 | 22 | 1435.5970 | K.LFIGGLNTETNEK.A | SEQ ID No: 72 |
| 23 | 30 | 833.9830 | K.ALEAVFGK.Y | SEQ ID No: 73 |
| 34 | 41 | 944.2410 | R.IVEVLLMK.D | SEQ ID No: 74 |
| 50 | 63 | 1486.6440 | R.GFAFVTFESPADAK.D | SEQ ID No: 75 |
| 68 | 72 | 563.6260 | R.DMNGK.S | SEQ ID No: 76 |
| 73 | 77 | 518.5670 | K.SLDGK.A | SEQ ID No: 77 |
| 81 | 93 | 1435.5570 | K.VEQATKPSFESGR.R | SEQ ID No: 78 |
| 95 | 101 | 716.8380 | R.GPPPPPR.S | SEQ ID No: 79 |
| 114 | 120 | 590.5940 | R.GGSGGTR.G | SEQ ID No: 80 |
| 121 | 125 | 512.5660 | R.GPPSR.G | SEQ ID No: 81 |
| 126 | 144 | 2050.1790 | R.GGHMDDGGYSMNFNMSS SR.G | SEQ ID No: 82 |
| 145 | 150 | 609.7670 | R.GPLPVK.R | SEQ ID No: 83 |
| 145 | 163 | 2089.86 | R.GPLPVKRGPPPRSGGPPP K.R | SEQ ID NO 84 |
| 152 | 156 | 522.6050 | R.GPPPR.S | SEQ ID No: 85 |
| 157 | 163 | 638.7210 | R.SGGPPPK.R | SEQ ID No: 86 |
| 165 | 172 | 769.8560 | R.SAPSGPVR.S | SEQ ID No: 87 |
| 173 | 180 | 737.7860 | R.SSSGMGGR.A | SEQ ID No: 88 |
| 181 | 185 | 528.6090 | R.APVSR.G | SEQ ID No: 89 |
| 186 | 195 | 1061.1190 | R.GRDSYGGPPR.R | SEQ ID No: 90 |
| 188 | 195 | 847.8830 | R.DSYGGPPR.R | SEQ ID No: 91 |
| 197 | 202 | 697.7890 | R.EPLPSR.R | SEQ ID No: 92 |
| 204 | 210 | 848.9540 | R.DVYLSPR.D | SEQ ID No: 93 |
| 211 | 224 | 1481.9584 | R.DGYSCKAQYSNRD | SEQ ID No: 70 |
| 224 | 229 | 723.7400 | R.DYPSSR.D | SEQ ID No: 94 |
| 233 | 239 | 814.8960 | R.DYAPPPR.D | SEQ ID No: 95 |
| 240 | 244 | 716.7480 | R.DYTYR.D | SEQ ID No: 96 |

TABLE 8-continued

Recovered Peptides From In-solution Digests Corresponding to HnRNPG

| Start | End | Peptide mass | Description (Sequence) | SEQ ID NO: |
|---|---|---|---|---|
| 245 | 252 | 907.8950 | R.DYGHSSSR.D | SEQ ID No: 97 |
| 253 | 258 | 751.7510 | R.DDYPSR.G | SEQ ID No: 98 |
| 259 | 263 | 596.5970 | R.GYSDR.D | SEQ ID No: 99 |
| 264 | 268 | 566.5710 | R.DGYGR.D | SEQ ID No: 100 |
| 271 | 282 | 1340.3280 | R.DYSDHPSGGSYR.D | SEQ ID No: 101 |
| 283 | 292 | 1177.1490 | R.DSYESYGNSR.S | SEQ ID No: 102 |
| 293 | 298 | 627.6980 | R.SAPPTR.G | SEQ ID No: 103 |
| 310 | 317 | 991.9670 | R.YDDYSSSR.D | SEQ ID No: 104 |
| 318 | 324 | 710.7010 | R.DGYGGSR.D | SEQ ID No: 105 |
| 325 | 331 | 800.7800 | R.DSYSSSR.S | SEQ ID No: 106 |
| 332 | 339 | 883.9130 | R.SDLYSSGR.D | SEQ ID No: 107 |
| 348 | 355 | 886.0340 | R.GLPPSMER.G | SEQ ID No: 108 |
| 356 | 361 | 685.7810 | R.GYPPPR.D | SEQ ID No: 109 |
| 362 | 369 | 887.8580 | R.DSYSSSSR.G | SEQ ID No: 110 |

TABLE 9

Summary of the peptides synthesized for VB1-213 epitope mapping studies.

| Peptides | Sequence - molecular weight | Outcome |
|---|---|---|
| HP1: | Biotin YSCKAQVSNED - 1467.76 amu | Positive |
| PSPep1: | Biotin TARIRAVGLLTVISK - 1823.9 amu | Non-specific |
| PSPep2: | Biotin SLNCVDDSQDYYVGK - 1929.34 amu | Non-specific |
| PSPep3 (Negative): | Biotin LCNASGAHALQ - 1306.59 amu | Negative |

TABLE 10

Comparative profiling of the binding affinities of different antibodies relative to PSCA peptides; the highlighted portion represents binding and competing specificity in the experiments.

| Peptides | VB1-213 | anti-PSCA | anti-EGFR | 4B5-IgG | comments |
|---|---|---|---|---|---|
| HP1 | 1.798 | 0.014 | 0.153 | -0.002 | specific |
| Competition | 92% | 2% | none | none | specific |
| PSPep1 | 1.492 | 1.589 | 1.995 | 2.112 | non-specific |
| Competition | 35% | 45% | 40% | 52% | non-specific |
| PSPep2 | 0.359 | 0.258 | — | 1.258 | non-specific |
| Competition | 30% | 30% | — | 40% | non-specific |
| Negative | no binding | no binding | no binding | no binding | negative |
| Competition | negative | negative | negative | negative | non-specific |

REFERENCES

1. Altschul, S. F., Gish, W., Miller, W., Myers, E. W., and Lipman, D. J. (1990). Basic local alignment search tool. J. Mol. Biol. 215, 403-410.

2. Altschul, S. F., Madden, T. L., Schaffer, A. A., Zhang, J., Zhang, Z., Miller, W., and Lipman, D. J. (1997). Gapped BLAST and PSI-BLAST: a new generation of protein database search programs. Nucleic Acids Res 25, 3389-3402.

3. Amara, N., Palapattu, G. S., Schrage, M., Gu, Z., Thomas, G. V., Dorey, F., Said, J., and Reiter, R. E. (2001). Prostate stem cell antigen is overexpressed in human transitional cell carcinoma. Cancer Res. 61, 4660-4665.

4. Andrianov, A. K., Jenkins, S. A., Payne, L., and Roberts, B. PHOSPHAZENE POLYELECTROLYTES AS IMMUNOADJUVANTS. Virus Research Institute. PCT/US94/07665 WO 95/02415, 1-49. Us. Dec. 7, 1993. Ref Type: Patent 5. Baker, M., Carr, F., Hellendoorn, K., Cizeau, J, MacDonald G. C, Entwistle, J., Bosc, D, and Glover, N. Modified Bouganin Proteins, Cytotoxins and Methods and Uses Thereof. Merck and Viventia Biotech. PCT/CA2005/000410 WO05090579A1. Mar. 18, 2005. Ref Type: Patent 6. Baldari, C., Murray, J. A., Ghiara, P., Cesareni, G., and Galeotti, C. L. (1987). A novel leader peptide which allows efficient secretion of a fragment of human interleukin 1 beta in *Saccharomyces cerevisiae*. EMBO J. 6, 229-234.

7. Benedict, C. A., MacKrell, A. J., and Anderson, W. F. (1997). Determination of the binding affinity of an anti-CD34 single-chain antibody using a novel, flow cytometry based assay. J. Immunol. Methods 201, 223-231.

8. Brinster, R. L., Chen, H. Y., Trumbauer, M. E., Yagle, M. K., and Palmiter, R. D. (1985). Factors affecting the efficiency of introducing foreign DNA into mice by microinjecting eggs. Proc Natl. Acad. Sci. U.S. A 82, 4438-4442.

9. Carrillo, H. and Lipman, D. (1988). The Multiple Sequence Alignment Problem in Biology. SIAM. J. Appl. Math. 48, 1073-1082.

10. Chahal, F. C. Method and System for Identification of Antigens. Viventia Biotech. WO06105653A1. Oct. 12, 2006. Apr. 4, 2006. Ref Type: Patent 11. Clackson, T., Hoogenboom, H. R., Griffiths, A. D., and Winter, G. (1991). Making antibody fragments using phage display libraries. Nature 352, 624-628.
12. Clements, J. D. and Dickinson, B. L. Mutant Enterotoxin Effective as a Non-Toxic Oral Adjuvant. PCT/US95/09005 WO 96/06627, 1-49. US. Nov. 6, 1995. Ref Type: Patent
13. Colcher, D., Esteban, J., and Mornex, F. (1986). Use of monoclonal antibodies as radiopharmaceuticals for the localization of human carcinoma xenografts in athymic mice. Methods Enzymol. 121, 802-816.
14. Cooper, M., Li, S. Q., Bhardwaj, T., Rohan, T., and Kandel, R. A. (2004). Evaluation of oligonucleotide arrays for sequencing of the p53 gene in DNA from formalin-fixed, paraffin-embedded breast cancer specimens. Clin Chem 50, 500-508.
15. Cullen, D., Gray, G. L., Wilson, L. J., Hayenga, K. J., Lamsa, M. H., Rey, M. W., Norton, S., and Berka, R. M. (1987). Controlled Expression and Secretion of Bovine Chymosin in *Aspergillus Nidulans*. Nat Biotech 5, 369-376.
16. Dannull, J., Diener, P. A., Prikler, L., Furstenberger, G., Cerny, T., Schmid, U., Ackermann, D. K., and Groettrup, M. (2000). Prostate stem cell antigen is a promising candidate for immunotherapy of advanced prostate cancer. Cancer Res. 60, 5522-5528.
17. David, G. S, and Reisfeld, R. A. (1974). Protein iodination with solid state lactoperoxidase. Biochemistry 13, 1014-1021.
18. Davies, D. R., Padlan, E. A., and Sheriff, S. (1990). Antibody-antigen complexes. Annu. Rev. Biochem. 59, 439-473.
19. Davies, D. R. and Cohen, G. H. (1996). Interactions of protein antigens with antibodies. Proc Natl. Acad. Sci. U.S. A 93, 7-12.
20. Demeure, M. J., Damsky, C. H., Elfman, F., Goretzki, P. E., Wong, M. G., and Clark, O. H. (1992). Invasion by cultured human follicular thyroid cancer correlates with increased beta 1 integrins and production of proteases. World J. Surg. 16, 770-776.
21. Devereux, J., Haeberli, P., and Smithies, O. (1984). A comprehensive set of sequence analysis programs for the VAX. Nucleic Acids Res 12, 387-395.
22. Dubey, P., Wu, H., Reiter, R. E., and Witte, O. N. (2001). Alternative pathways to prostate carcinoma activate prostate stem cell antigen expression. Cancer Res. 61, 3256-3261.
23. Epand, R. M., Bottega, R., and Huang, L. Method for delivering nucleic acids into cells. University of Tennessee. [U.S. Pat. No. 5,283,185], 1-16. Jan. 1, 1994. US. Ref Type: Patent
24. Frische, K., Meldal, M., Werdelin, O., Mouritsen, S., Jensen, T., Galli-Stampino, L., and Bock, K. (1996). Multiple column synthesis of a library of T-cell stimulating Tn-antigenic glycopeptide analogues for the molecular characterization of T-cell-glycan specificity. J Pept. Sci, 2, 212-222.
25. Gajewcysk, D., Boux, H., Novak, A., and Klein, M. Proteinaceous Adjuvants. Connaught Laboratories Limited. PCT/CA95/00341 WO 95/34323, 1-30. Canada. Oct. 6, 1994. Ref Type: Patent
26. Gennaro, A. R. (2000). Remington's Pharmaceutical Sciences. (Easton, Pa.: Mack Publishing Company).
27. Giudicelli, V., Chaume, D., and Lefranc, M. P. (2004). IMGT/V-QUEST, an integrated software program for immunoglobulin and T cell receptor V-J and V-D-J rearrangement analysis. Nucleic Acids Res 32, W435-W440.
28. Goeddel, D. V. (1990). Systems for heterologous gene expression. Methods Enzymol. 185, 3-7.
29. Goodson, J. M. (1984). Dental Applications. In Medical Applications of Controlled Release, (Boca Raton, Fla.: CRC Press), pp. 115-138.
30. Griffin, H. G. and Griffin, A. M. (1994). PCR technology: current innovations. (Boca Raton: CRC Press).
31. Gu, Z., Yamashiro, J., Kono, E., and Reiter, R. E. (2005). Anti-prostate stem cell antigen monoclonal antibody 1G8 induces cell death in vitro and inhibits tumor growth in vivo via a Fc-independent mechanism. Cancer Res. 65, 9495-9500.
32. Gudas, J., Jakobovits, A., Jia, X-C., Morrison, R., Morrsion, K., Shao, H., Challita-Eid, P., and Raitano, A. ANTIBODIES AND RELATED MOLECULES THAT BIND TO PSCA PROTEINS. AGENSYS, INC. US0017412 [U.S. Pat. No. 5,118,864], 1-282. Dec. 15, 2005. WO. May 17, 2005. Ref Type: Patent
33. Haensler, J., Trannoy, E., and Ronco. J. Adjuvant for a Vaccine Composition. Pasteur Merieux. PTC/FR95/01495 WO 96/14831, 1-30. France. Ref Type: Patent
34. Hammer, R. E., Brinster, R. L., Rosenfeld, M. G., Evans, R. M., and Mayo, K. E. (1985). Expression of human growth hormone-releasing factor in transgenic mice results in increased somatic growth. Nature 315, 413-416.
35. Harvey, B. R., Georgiou, G., Hayhurst, A., Jeong, K. J., Iverson, B. L., and Rogers, G. K. (2004). Anchored periplasmic expression, a versatile technology for the isolation of high-affinity antibodies from *Escherichia coli-expressed* libraries. Proc Natl. Acad. Sci. U. S. A 101, 9193-9198.
36. Hawkins, R. E., Russell, S. J., and Winter, G. (1992). Selection of phage antibodies by binding affinity. Mimicking affinity maturation. J. Mol. Biol. 226, 889-896.
37. Henikoff, S, and Henikoff, J. G. (1992). Amino acid substitution matrices from protein blocks. Proc Natl. Acad. Sci. U.S. A 89, 10915-10919.
38. Hinnen, A., Hicks, J. B., and Fink, G. R. (1978). Transformation of yeast. Proc Natl. Acad. Sci. U.S. A 75, 1929-1933.
39. Ho, M., Kreitman, R. J., Onda, M., and Pastan, I. (2005). In vitro antibody evolution targeting germline hot spots to increase activity of an anti-CD22 immunotoxin. J. Biol. Chem. 280, 607-617.
40. Hunter, W. M. and Greenwood, F. C. (1962). Preparation of iodine-131 labelled human growth hormone of high specific activity. Nature 194, 495-496.
41. Huse, W. D., Sastry, L., Iverson, S. A., Kang, A. S., ting-Mees, M., Burton, D. R., Benkovic, S. J., and Lerner, R. A. (1989). Generation of a large combinatorial library of the immunoglobulin repertoire in phage lambda. Science 246, 1275-1281.
42. Ito, H., Fukuda, Y., Murata, K., and Kimura, A. (1983). Transformation of intact yeast cells treated with alkali cations. J. Bacteriol. 153, 163-168.
43. Itoh, Kyogo. Tumor antigens. ITOH, K. Y. O. G. 000498075[25130899], 1-27. Jun. 16, 2005. US. Dec. 10, 2002. Ref Type: Patent
44. John Wiley & Sons (2006). Current Protocols in Molecular Biology. (New York, N.Y.: John Wiley & Sons).
45. Karlin, S, and Altschul, S. F. (1990). Methods for assessing the statistical significance of molecular sequence features by using general scoring schemes. Proc Natl. Acad. Sci. U.S. A 87, 2264-2268.
46. Karlin, S, and Altschul, S. F. (1993). Applications and statistics for multiple high-scoring segments in molecular sequences. Proc Natl. Acad. Sci. U.S. A 90, 5873-5877.

47. Kaufman, R. J., Murtha, P., and Davies, M. V. (1987). Translational efficiency of polycistronic mRNAs and their utilization to express heterologous genes in mammalian cells. EMBO J. 6, 187-193.

48. Kensil, C., Marciani, D., and Beltz, G. SAPONIN ADJUVANT. Cambridge Bioscience. PCT/US88/01842 WO 88/09336, 1-85. US. Ref Type: Patent 49. Kohler, G. and Milstein, C. (1975). Continuous cultures of fused cells secreting antibody of predefined specificity. Nature 256, 495-497.

50. Kozbor, D. and Rodor, J. C. (1983). The Production of Monoclonal Antibodies from Human Lymphocytes. Immunol. Today 4, 72-79.

51. Kurjan, J. and Herskowitz, I. (1982). Structure of a yeast pheromone gene (MF alpha): a putative alpha-factor precursor contains four tandem copies of mature alpha-factor. Cell 30, 933-943.

52. Lam, J. S., Yamashiro, J., Shintaku, I. P., Vessella, R. L., Jenkins, R. B., Horvath, S., Said, J. W., and Reiter, R. E. (2005). Prostate stem cell antigen is overexpressed in prostate cancer metastases. Clin. Cancer Res. 11, 2591-2596.

53. Leder, P. and Stewart, T. A. Transgenic Non Human Mammals. President and Fellows of Harvard College. [U.S. Pat. No. 4,736,866], 1-8. Apr. 12, 1988. US. Jun. 22, 1984. Ref Type: Patent 54. Lesk, A. (1988). Computational Molecular Biology: Sources and Methods for Sequence Analysis. (New York, N.Y.: Oxford University Press).

55. Li, J., Hawkins, I. C., Harvey, C. D., Jennings, J. L., Link, A. J., and Patton, J. G. (2003). Regulation of alternative splicing by SRrp86 and its interacting proteins. Mol. Cell. Biol. 23, 7437-7447.

56. Low, N. M., Holliger, P. H., and Winter, G. (1996). Mimicking somatic hypermutation: affinity maturation of antibodies displayed on bacteriophage using a bacterial mutator strain. J. Mol. Biol. 260, 359-368.

57. Luckow, V. A. and Summers, M. D. (1989). High level expression of nonfused foreign genes with *Autographa californica* nuclear polyhedrosis virus expression vectors. Virology 170, 31-39.

58. Mackay, A. R., Gomez, D. E., Nason, A. M., and Thorgeirsson, U. P. (1994). Studies on the effects of laminin, E-8 fragment of laminin and synthetic laminin peptides PA22-2 and YIGSR on matrix metalloproteinases and tissue inhibitor of metalloproteinase expression. Lab Invest 70, 800-806.

59. Maione, T. E., Gray, G. S., Hunt, A. J., and Sharpe, R. J. (1991). Inhibition of tumor growth in mice by an analogue of platelet factor 4 that lacks affinity for heparin and retains potent angiostatic activity. Cancer Res 51, 2077-2083.

60. McCafferty, J., Griffiths, A. D., Winter, G., and Chiswell, D. J. (1990). Phage antibodies: filamentous phage displaying antibody variable domains. Nature 348, 552-554.

61. McHeyzer-Williams, M. G. (2003). B-cell Signalling Mechanisms and Activation. In Fundamental Immunology, W. E. Paul, ed. (Baltimore: Lippincott, Williams & Watkins), pp. 195-225.

62. Merrifield, R. B. (1964). Solid Phase Peptide Synthesis 3: An Improved Synthesis of Bradykinin. Biochemistry 3, 1385-1390.

63. Min, L. (2000). Applications of display technology in protein analysis. Nat Biotech 18, 1251-1256.

64. Moore, D. H., Allison, B., Look, K. Y., Sutton, G. P., and Bigsby, R. M. (1997). Collagenase expression in ovarian cancer cell lines. Gynecol. Oncol 65, 78-82.

65. Myers, E. W. and Miller, W. (1988). Optimal alignments in linear space. Comput. Appl. Biosci. 4, 11-17.

66. Najib, S., Martin-Romero, C., Gonzalez-Yanes, C., and Sanchez-Margalet, V. (2005). Role of Sam68 as an adaptor protein in signal transduction. Cell Mol. Life. Sci. 62, 36-43.

67. Nandabalan, K., Yang, M., and Schulz, V. P. 53BP2 complexes. CuraGen Corporation. 000338123 [U.S. Pat. No. 6,627,405], 1-78. Sep. 30, 2003. U.S. Pat. No. 6,184,205. Jun. 22, 1999. Ref Type: Patent 68. Needleman, S. B. and Wunsch, C. D. (1970). A general method applicable to the search for similarities in the amino acid sequence of two proteins. J. Mol. Biol. 48, 443-453.

69. Neuberger, M. S, and Milstein, C. (1995). Somatic hypermutation. Curr. Opin. Immunol. 7, 248-254.

70. Nygren, H. (1982). Conjugation of horseradish peroxidase to Fab fragments with different homobifunctional and heterobifunctional cross-linking reagents. A comparative study. J Histochem. Cytochem. 30, 407-412.

71. Olafsen, T., Gu, Z., Sherman, M. A., Leyton, J. V., Witkosky, M. E., Shively, J. E., Raubitschek, A. A., Morrison, S. L., Wu, A. M., and Reiter, R. E. (2007). Targeting, imaging, and therapy using a humanized antiprostate stem cell antigen (PSCA) antibody. J Immunother. 30, 396-405.

72. Pain, D. and Surolia, A. (1981). Preparation of protein A-peroxidase monoconjugate using a heterobifunctional reagent, and its use in enzyme immunoassays. J. Immunol. Methods 40, 219-230.

73. Palmiter, R. D., Norstedt, G., Gelinas, R. E., Hammer, R. E., and Brinster, R. L. (1983). Metallothionein-human GH fusion genes stimulate growth of mice. Science 222, 809-814.

74. Palmiter, R. D. and Brinster, R. L. (1985). Transgenic mice. Cell 41, 343-345.

75. Rappuoli, R. Non Toxic Mucosal Adjuvant. PCT/IB95/00013 WO 95/17211, 1-30. Ref Type: Patent 76. Reiter, R. E., Gu, Z., Watabe, T., Thomas, G., Szigeti, K., Davis, E., Wahl, M., Nisitani, S., Yamashiro, J., Le Beau, M. M., Loda, M., and Witte, O. N. (1998). Prostate stem cell antigen: a cell surface marker overexpressed in prostate cancer. Proc. Natl. Acad. Sci. U.S. A 95, 1735-1740.

77. Reiter, R. E. and Witte, O. N. PSCA: prostate stem cell antigen and uses thereof. The Regents of the University of California. 000934773 [U.S. Pat. No. 6,825,326], 1-126. Nov. 30, 2004. U.S. Pat. Nos. 5,693,762, 5,856,136, 6,258,939. Aug. 21, 2001. Ref Type: Patent 78. Roder, J. C., Cole, S. P., and Kozbor, D. (1986). The EBV-hybridoma technique. Methods Enzymol. 121, 140-167.

79. Saffran, D. C., Raitano, A. B., Hubert, R. S., Witte, O. N., Reiter, R. E., and Jakobovits, A. (2001). Anti-PSCA mAbs inhibit tumor growth and metastasis formation and prolong the survival of mice bearing human prostate cancer xenografts. Proc. Natl. Acad. Sci. U.S. A 98, 2658-2663.

80. Sage, E. H., Bassuk, J. A., Yost, J. C., Folkman, M. J., and Lane, T. F. (1995). Inhibition of endothelial cell proliferation by SPARC is mediated through a Ca(2+)-binding EF-hand sequence. J Cell Biochem. 57, 127-140.

81. Salvatore, G., Beers, R., Margulies, I., Kreitman, R. J., and Pastan, I. (2002). Improved cytotoxic activity toward cell lines and fresh leukemia cells of a mutant anti-CD22 immunotoxin obtained by antibody phage display. Clin Cancer Res 8, 995-1002.

82. Sambrook, J., MacCallum, P., and Russell, D. (2001). Molecular Cloning: A Laboratory Manual. Cold Spring Harbor Laboratory Press).

83. Schier, R., McCall, A., Adams, G. P., Marshall, K. W., Merritt, H., Yim, M., Crawford, R. S., Weiner, L. M., Marks, C., and Marks, J. D. (1996). Isolation of picomolar affinity anti-c-erbB-2 single-chain Fv by molecular evolution of the complementarity determining regions in the center of the antibody binding site. J. Mol. Biol. 263, 551-567.
84. Schneider, J. C., Chew, L. C., Badgley, A. K., and Ramseier, T. M. Protein expression systems. Dow Global Technologies. US2004000994138, 1-75. 2005. US. Aug. 25, 2005. Ref Type: Patent
85. Schultz, L. D., Tanner, J., Hofmann, K. J., Emini, E. A., Condra, J. H., Jones, R. E., Kieff, E., and Ellis, R. W. (1987). Expression and secretion in yeast of a 400-kDa envelope glycoprotein derived from Epstein-Barr virus. Gene 54, 113-123.
86. Seed, B. (1987). An LFA-3 cDNA encodes a phospholipid-linked membrane protein homologous to its receptor CD2. Nature 329, 840-842.
87. Sherman, M. A., Wu, A. M., and Reiter, R. E. Humanized anti-prostate stem cell antigen monoclonal antibody. 000432304 [26269557], 1-35. Nov. 30, 2006. US. May 10, 2006. Ref Type: Patent
88. Shi, Y. E., Torri, J., Yieh, L., Wellstein, A., Lippman, M. E., and Dickson, R. B. (1993). Identification and characterization of a novel matrix-degrading protease from hormone-dependent human breast cancer cells. Cancer Res 53, 1409-1415.
89. Shin, K. H., Kang, M. K., Kim, R. H., Christensen, R., and Park, N. H. (2006). Heterogeneous nuclear ribonucleoprotein G shows tumor suppressive effect against oral squamous cell carcinoma cells. Clin. Cancer Res. 12, 3222-3228.
90, Shin, K. H., Kim, R. H., Kang, M. K., Kim, R. H., Kim, S. G., Lim, P. K., Yochim, J. M., Baluda, M, A., and Park, N. H. (2007). p53 promotes the fidelity of DNA end-joining activity by, in part, enhancing the expression of heterogeneous nuclear ribonucleoprotein G. DNA Repair (Amst) 6, 830-840.
91. Sinkar, V. P., White, F. F., and Gordon, M. P. (1987). Molecular Biology of the RI Plasmid—A Review. J. Biosci. 11, 47-57.
92. Smith, G. E., Summers, M. D., and Fraser, M. J. (1983). Production of human beta interferon in insect cells infected with a baculovirus expression vector. Mol. Cell. Biol. 3, 2156-2165.
93. Smith, T. F. and Waterman, M. S. (1981). Comparions of Biosequences. Advances in Applied Mathematics 2, 482-489.
94. Soulard, M., Della, V., V, and Larsen, C. J. (2002). Autoimmune antibodies to hnRNPG protein in dogs with systemic lupus erythematosus: epitope mapping of the antigen. J. Autoimmun. 18, 221-229.
95. Spiess, E., Bruning, A., Gack, S., Ulbricht, B., Spring, H., Trefz, G., and Ebert, W. (1994). Cathepsin B activity in human lung tumor cell lines: ultrastructural localization, pH sensitivity, and inhibitor status at the cellular level. J Histochem. Cytochem. 42, 917-929.
96. Tanaka, M., Komatsu, N., Terakawa, N., Yanagimoto, Y., Oka, M., Sasada, T., Mine, T., Gouhara, S., Shichijo, S., Okuda, S., and Itoh, K. (2007). Increased levels of IgG antibodies against peptides of the prostate stem cell antigen in the plasma of pancreatic cancer patients. Oncol Rep 18, 161-166,
97. Therasse, P., Arbuck, S. G., Eisenhauer, E. A., Wanders, J., Kaplan, R. S., Rubinstein, L., Verweij, J., Van, G. M., van Oosterom, A. T., Christian, M. C., and Gwyther, S. G. (2000). New guidelines to evaluate the response to treatment in solid tumors. European Organization for Research and Treatment of Cancer, National Cancer Institute of the United States, National Cancer Institute of Canada. J. Natl. Cancer Inst. 92, 205-216.
98. Thompson, E. W., Yu, M., Bueno, J., Jin, L., Maiti, S. N., Palao-Marco, F. L., Pulyaeva, H., Tamborlane, J. W., Tirgari, R., Wapnir, I., and (1994). Collagen induced MMP-2 activation in human breast cancer. Breast Cancer Res Treat. 31, 357-370.
99. Thompson, J. D., Higgins, D. G., and Gibson, T. J. (1994). CLUSTAL W: improving the sensitivity of progressive multiple sequence alignment through sequence weighting, position-specific gap penalties and weight matrix choice. Nucleic Acids Res 22, 4673-4680.
100. Tolsma, S. S., Volpert, O. V., Good, D. J., Frazier, W. A., Polyerini, P. J., and Bouck, N. (1993). Peptides derived from two separate domains of the matrix protein thrombospondin-1 have anti-angiogenic activity. J. Cell Biol. 122, 497-511.
101. Tomlinson, I. M., Cox, J. P., Gherardi, E., Lesk, A. M., and Chothia, C. (1995). The structural repertoire of the human V kappa domain. EMBO J. 14, 4628-4638.
102. Tomlinson, I. M., Walter, G., Jones, P. T., Dear, P. H., Sonnhammer, E. L., and Winter, G. (1996). The imprint of somatic hypermutation on the repertoire of human germline V genes. J. Mol. Biol. 256, 813-817.
103. Trakht, I. Development of human monoclonal antibodies and uses thereof. The Trustees of Columbia University in the City of New York. 000040833 [U.S. Pat. No. 6,197, 582], 1-23, Mar. 6, 2001. U.S. Pat. No. 4,714,681. Mar. 18, 1998. Ref Type: Patent
104. Trakht, I. Development of human monoclonal antibodies and uses thereof. The Trustees of Columbia University in the City of New York. 000767578 [U.S. Pat. No. 7,220, 559], 1-24. May 22, 2007. U.S. Pat. Nos. 4,574,116, 4,613, 576, 4,618,577, 4,634,664, 4,634,666, 4,668,629, 4,689, 299, 4,714,681, 4,720,459, 4,744,982, 4,761,377, 4,800, 155, 4,916,072, 4,950,595, 4,954,449, 4,997,762, 5,001, 065, 5,003,046, 5,006,470, 5,093,261, 5,126,259, 5,196, 337, 5,215,913, 5,252,480, 5,298,419, 5,426,046, 5,459, 060, 5,506,132, 5,576,184, 5,652,114, 6,197,582. Jan. 23, 2001. Ref Type: Patent
105. Venables, J. P., Elliott, D. J., Makarova, O. V., Makarov, E. M., Cooke, H. J., and Eperon, I. C. (2000). RBMY, a probable human spermatogenesis factor, and other hnRNP G proteins interact with Tra2beta and affect splicing. Hum. Mol. Genet. 9, 685-694.
106. Wagner, S. D., Milstein, C., and Neuberger, M. S. (1995). Codon bias targets mutation. Nature 376, 732.
107. Wansch, E. ed. (1987). Houben-Weyl: Methods of Organic Chemistry. (Stuttgart: Thieme).
108. Ward, E. S., Gussow, D., Griffiths, A. D., Jones, P. T., and Winter, G. (1989). Binding activities of a repertoire of single immunoglobulin variable domains secreted from *Escherichia coli*. Nature 341, 544-546.
109. Wensel, T. G. and Meares, C. F. (1983). Bifunctional Chelating Agents for Binding Metal Ion to Proteins. In Radioimmunoimaging and Radioimmunotherapy, S. W. Burchiel and B. A. Rhodes, eds. (New York, N.Y.: Elsevier Science Publishing), pp. 185-196.
110. Wente, M. N., Jain, A., Kono, E., Berberat, P. O., Giese, T., Reber, H. A., Friess, H., Buchler, M. W., Reiter, R. E., and Hines, O. J. (2005). Prostate stem cell antigen is a putative target for immunotherapy in pancreatic cancer. Pancreas 31, 119-125.
111. Wong, S. S. (1991). Chemistry of Protein Conjugation and Crosslinking. (Boca Raton, Fla.: CRC Press).

112. World Health Organization (2003). World Cancer Report. (Geneva, Switzerland: WHO Press).

113. Yang, W. P., Green, K., Pinz-Sweeney, S., Briones, A. T., Burton, D. R., and Barbas, C. F., III (1995). CDR walking mutagenesis for the affinity maturation of a potent human anti-HIV-1 antibody into the picomolar range. J. Mol. Biol. 254, 392-403.

114. Young, T. N., Rodriguez, G. C., Rinehart, A. R., Bast, R. C., Jr., Pizzo, S. V., and Stack, M. S. (1996). Characterization of gelatinases linked to extracellular matrix invasion in ovarian adenocarcinoma: purification of matrix metalloproteinase 2. Gynecol. Oncol 62, 89-99.

115. Zambryski, P., Herrerra-Estrella, L., DeBlock, M., and Van Montagu, M. (1984). In Genetic Engineering: Principles and Methods, J. Setlow and A. Hollaender, eds. (New York, N.Y.: Plenum Press), pp. 253-278.

116. Zhang, Z., Gildersleeve, J., Yang, Y. Y., Xu, R., Loo, J. A., Uryu, S., Wong, C. H., and Schultz, P. G. (2004). A new strategy for the synthesis of glycoproteins. Science 303, 371-373.

117. Zhigang, Z. and Wenlv, S. (2004). Prostate stem cell antigen (PSCA) expression in human prostate cancer tissues and its potential role in prostate carcinogenesis and progression of prostate cancer. World J. Surg. Oncol. 2, 13.

118. Zhigang, Z. and Wenlv, S. (2004). Prostate stem cell antigen (PSCA) expression in human prostate cancer tissues: implications for prostate carcinogenesis and progression of prostate cancer. Jpn. J. Clin. Oncol. 34, 414-419.

119. Zolla-Pazner, S., Gorny, M. K., and Vitetta, E. S. METHOD OF TREATING HIV INFECTIONS USING IMMUNOTOXINS. New York University and University of Texas Board of Regents. PCT/US90/01396, WO 90/10457, 1-44. US. Ref Type: Patent 120. Wicha M S, Liu S and Dontu G. 2006. Cancer Stem Cells: An old idea—a paradigm shift. Cancer Res. 66, 1883-1890.

121 Ginestier C, Hur M H, Charafe-Jauffret E et al. 2007. ALDH1 is a marker of normal and malignant human stem cells and a predictor of poor clinical outcome. Cell Stem Cell, 1, 555-567.

We claim:

1. An antibody or an antigen binding fragment thereof that specifically binds to prostate stem cell antigen (PSCA) or a variant heterogeneous ribonucleoprotein G (HnRNPG), said antibody comprising a heavy chain variable region comprising complementarity determining regions (CDRs) comprising the amino acid sequences of SEQ ID NOs: 10, 11, and 12 and a light chain variable region comprising CDRs comprising the amino acid sequences of SEQ ID NOs: 7, 8, and 9.

2. The antibody of claim 1, wherein said PSCA comprises SEQ ID NO: 17.

3. The antibody of claim 1, wherein said variant of HnRNPG comprises an amino acid sequence selected from SEQ ID NO: 71 and SEQ ID NO: 113 with one or more amino acid substitutions at positions 216, 218, 219, and/or 222 thereof.

4. The antibody of claim 1, wherein said antibody specifically binds to an epitope of said PSCA or variant HnRNPG comprising an amino acid sequence selected from SEQ ID NO: 23, SEQ ID NO: 41, SEQ ID NO: 111, and SEQ ID NO: 112.

5. The antibody of claim 1, wherein said antibody is a monoclonal antibody.

6. The antigen binding fragment of the antibody of claim 1, wherein said fragment is a Fab, Fab', or F(ab')2.

7. The antibody of claim 1, wherein said antibody is a recombinant antibody.

8. The antibody of claim 7, wherein said antibody is a scFv, dsFv, ds-scFv, dimer, minibody, diabody, bispecific antibody, or multimer.

9. The antibody of claim 7, wherein said antibody is chimeric or humanized.

10. A composition comprising the antibody of claim 7 and a pharmaceutically acceptable excipient, carrier, buffer, or stabilizer.

11. An immunoconjugate comprising the antibody of claim 7 and a therapeutic agent.

12. The immunoconjugate of claim 11, wherein said therapeutic agent is a cytotoxin.

13. The immunoconjugate of claim 12, wherein said cytotoxin is a ribosome inactivating polypeptide.

14. The immunoconjugate of claim 12, wherein said cytotoxin is selected from the group consisting of gelonin, bouganin, saporin, ricin, ricin A chain, bryodin, diphtheria, restrictocin and *Pseudomonas* exotoxin A.

15. The immunoconjugate of claim 12, wherein said cytotoxin is bouganin.

16. The immunoconjugate of claim 12, wherein said cytotoxin is a modified bouganin having the amino acid sequence of SEQ ID NO: 52.

17. The immunoconjugate of claim 12, wherein said cytotoxin is a truncated form of *Pseudomonas* exotoxin A consisting of amino acids 252-608 thereof.

18. The immunoconjugate of claim 12, wherein said immunotoxin binds to a PSCA or variant HnRNPG on or in a cancer cell.

19. The immunoconjugate of claim 12, wherein said immunotoxin is internalized by a cancer cell expressing PSCA or variant HnRNPG.

20. The immunoconjugate of claim 12, wherein said immunotoxin comprises SEQ ID NO: 49.

21. The immunoconjugate of claim 12, wherein said immunotoxin comprises SEQ ID NO: 51.

22. The immunoconjugate of claim 20, wherein said immunotoxin is encoded by a nucleic acid molecule comprising SEQ ID NO: 48.

23. The immunoconjugate of claim 21, wherein said immunotoxin is encoded by a nucleic acid molecule comprising SEQ ID NO: 50.

24. A composition comprising the immunoconjugate of claim 11 and a pharmaceutically acceptable excipient, carrier, buffer, or stabilizer.

25. A nucleic acid molecule encoding an antibody according to claim 1.

26. A vector comprising a nucleic acid molecule according to claim 25.

27. An isolated host cell comprising a vector according to claim 26.

28. A method of preparing an antibody or an antigen binding fragment thereof that specifically binds to PSCA or a variant HnRNPG, said method comprising culturing a host cell according to claim 27, wherein said antibody comprises a heavy chain variable region comprising CDRs comprising the amino acid sequences of SEQ ID NOs: 10, 11, and 12 and a light chain variable region comprising CDRs comprising the amino acid sequences of SEQ ID NOs: 7, 8, and 9.

29. A nucleic acid molecule encoding an immunoconjugate according to claim 11.

30. The nucleic acid molecule of claim 29 comprising SEQ ID NO: 48.

31. The nucleic acid molecule of claim 29 comprising SEQ ID NO: 50.

32. A vector comprising a nucleic acid molecule according to claim 29.

33. An isolated host cell comprising a vector according to claim 32.

34. A method of preparing an immunoconjugate comprising an antibody or an antigen binding fragment thereof that specifically binds to PSCA or a variant HnRNPG and a therapeutic agent, said method comprising culturing a host cell according to claim 33, wherein said antibody comprises a heavy chain variable region comprising CDRs comprising the amino acid sequences of SEQ ID NOs: 10, 11, and 12 and a light chain variable region comprising CDRs comprising the amino acid sequences of SEQ ID NOs: 7, 8, and 9.

35. A kit comprising an antibody or antigen binding fragment thereof according to claim 1.

36. A kit comprising an immunoconjugate according to claim 11.

37. A detectably labeled antibody or an antigen binding fragment thereof that specifically binds to prostate stem cell antigen (PSCA) or a variant heterogeneous ribonucleoprotein G (HnRNPG), said antibody comprising a heavy chain variable region comprising CDRs comprising the amino acid sequences of SEQ ID NOs: 10, 11, and 12 and a light chain variable region comprising CDRs comprising the amino acid sequences of SEQ ID NOs: 7, 8, and 9.

38. The detectably labeled antibody or antigen binding fragment thereof according to claim 37, wherein said antibody or antigen binding fragment thereof is labeled with a radioisotope, a fluorescent compound, a chemiluminescent compound, an enzyme, an imaging agent or a metal ion.

39. A kit comprising a detectably labeled antibody or antigen binding fragment thereof according to claim 37.

* * * * *

SEQUENCE LISTING

```
<160> NUMBER OF SEQ ID NOS: 113

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1

ctcaccatgg agtttgggct gagctgggtt                                        30


<210> SEQ ID NO 2
<211> LENGTH: 36
<212> TYPE: DNA
<213> ORGANISM: Artificial Sequence
<220> FEATURE:
<223> OTHER INFORMATION: Primer

<400> SEQUENCE: 2

caggcagccc agggccgctg tgcccccaga ggtgct                                 36


<210> SEQ ID NO 3
<211> LENGTH: 27
<212> TYPE: DNA
<213> ORGANISM: Artificial Sequence
<220> FEATURE:
<223> OTHER INFORMATION: Primer

<400> SEQUENCE: 3

atgrcctgsw cycctctcyt yctswyc                                           27


<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4

atgrcctgsw cycctctcyt yctswyc                                           27


<210> SEQ ID NO 5
```

-continued

<211> LENGTH: 27
<212> TYPE: DNA
<213> ORGANISM: Artificial Sequence
<220> FEATURE:
<223> OTHER INFORMATION: Primer

<400> SEQUENCE: 5
atgrcctgsw cycctctcyt yctswyc 27

<210> SEQ ID NO 6
<211> LENGTH: 39
<212> TYPE: DNA
<213> ORGANISM: Artificial Sequence
<220> FEATURE:
<223> OTHER INFORMATION: Primer

<400> SEQUENCE: 6
ggtggtctcc actcccgcct tgacggggct gccatctgc 39

<210> SEQ ID NO 7
<211> LENGTH: 11
<212> TYPE: PRT
<213> ORGANISM: Homo sapiens

<400> SEQUENCE: 7

Ser Gly Asn Lys Leu Gly Asp Lys Tyr Ala Cys
1 5 10

<210> SEQ ID NO 8
<211> LENGTH: 7
<212> TYPE: PRT
<213> ORGANISM: Homo sapiens

<400> SEQUENCE: 8

Gln Asp Ser Lys Arg Pro Ser
1 5

<210> SEQ ID NO 9
<211> LENGTH: 9
<212> TYPE: PRT
<213> ORGANISM: Homo sapiens

<400> SEQUENCE: 9

Gln Ala Trp Asp Asn Ser Thr Ala Val
1 5

<210> SEQ ID NO 10
<211> LENGTH: 5
<212> TYPE: PRT
<213> ORGANISM: Homo sapiens

<400> SEQUENCE: 10

Ser Tyr Ala Met Ser
1 5

<210> SEQ ID NO 11
<211> LENGTH: 17
<212> TYPE: PRT
<213> ORGANISM: Homo sapiens

<400> SEQUENCE: 11

Thr Ile Ser Gly Arg Gly Val Thr Thr Tyr Tyr Ala Asp Ser Val Lys
1 5 10 15

Gly

-continued

<210> SEQ ID NO 12
<211> LENGTH: 10
<212> TYPE: PRT
<213> ORGANISM: Homo sapiens

<400> SEQUENCE: 12

```
Asp Arg Thr Arg Tyr Tyr Gly Met Asp Val
1               5                   10
```

<210> SEQ ID NO 13
<211> LENGTH: 357
<212> TYPE: DNA
<213> ORGANISM: Homo sapiens

<400> SEQUENCE: 13

```
gaggtgcagc tgttggagtc tgggggaggc ttggtacagc ctggggggtc cctgagactc      60

tcctgtgcag cctcgggatt cacctttaga agctatgcca tgagctgggt ccgccaggct     120

ccagggaagg ggctggaatg ggtctcaact attagtggtc gtggtgttac cacatactac     180

gcagactccg tgaagggccg gttcaccatc tccagagaca attccaagaa cacactgtat     240

ttgcaaatga acagcctgag agccgacgac acggccctat attactgtgc gaaagatcgt     300

acccgctact acggtatgga cgtctggggc caagggacca cggtcaccgt ctcctca        357
```

<210> SEQ ID NO 14
<211> LENGTH: 119
<212> TYPE: PRT
<213> ORGANISM: Homo sapiens

<400> SEQUENCE: 14

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Thr Ile Ser Gly Arg Gly Val Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Leu Tyr Tyr Cys
                85                  90                  95

Ala Lys Asp Arg Thr Arg Tyr Tyr Gly Met Asp Val Trp Gly Gln Gly
            100                 105                 110

Thr Thr Val Thr Val Ser Ser
        115
```

<210> SEQ ID NO 15
<211> LENGTH: 321
<212> TYPE: DNA
<213> ORGANISM: Homo sapiens

<400> SEQUENCE: 15

```
tcctatgagc tgactcagcc accctcagtg tccgtgtccc caggacagac agccagcatc      60

acctgctctg gaaataaatt gggggataaa tatgcttgct ggtatcagca gaagtcaggc     120

cagtcccctg tgctggtcat ctatcaagat tccaagcggc cctcagggat ccctgagcga     180

ttctctggct ccaactctgg gaacacagcc actctgacca tcagcgggac ccaggctttg     240

gatgaggctg actattactg tcaggcgtgg gacaacagca ctgcggtatt cggcggaggg     300
```

accaagctga ccgtcctagg t 321

<210> SEQ ID NO 16
<211> LENGTH: 107
<212> TYPE: PRT
<213> ORGANISM: Homo sapiens

<400> SEQUENCE: 16

```
Ser Tyr Glu Leu Thr Gln Pro Pro Ser Val Ser Val Ser Pro Gly Gln
1               5                   10                  15

Thr Ala Ser Ile Thr Cys Ser Gly Asn Lys Leu Gly Asp Lys Tyr Ala
            20                  25                  30

Cys Trp Tyr Gln Gln Lys Ser Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Leu
65                  70                  75                  80

Asp Glu Ala Asp Tyr Tyr Cys Gln Ala Trp Asp Asn Ser Thr Ala Val
                85                  90                  95

Phe Gly Gly Gly Thr Lys Leu Thr Val Leu Gly
            100                 105
```

<210> SEQ ID NO 17
<211> LENGTH: 123
<212> TYPE: PRT
<213> ORGANISM: Homo sapiens

<400> SEQUENCE: 17

```
Met Lys Ala Val Leu Leu Ala Leu Leu Met Ala Gly Leu Ala Leu Gln
1               5                   10                  15

Pro Gly Thr Ala Leu Leu Cys Tyr Ser Cys Lys Ala Gln Val Ser Asn
            20                  25                  30

Glu Asp Cys Leu Gln Val Glu Asn Cys Thr Gln Leu Gly Glu Gln Cys
        35                  40                  45

Trp Thr Ala Arg Ile Arg Ala Val Gly Leu Leu Thr Val Ile Ser Lys
    50                  55                  60

Gly Cys Ser Leu Asn Cys Val Asp Asp Ser Gln Asp Tyr Tyr Val Gly
65                  70                  75                  80

Lys Lys Asn Ile Thr Cys Cys Asp Thr Asp Leu Cys Asn Ala Ser Gly
                85                  90                  95

Ala His Ala Leu Gln Pro Ala Ala Ala Ile Leu Ala Leu Leu Pro Ala
            100                 105                 110

Leu Gly Leu Leu Leu Trp Gly Pro Gly Gln Leu
        115                 120
```

<210> SEQ ID NO 18
<211> LENGTH: 27
<212> TYPE: PRT
<213> ORGANISM: Homo sapiens

<400> SEQUENCE: 18

```
Lys Ala Val Leu Leu Ala Leu Leu Met Ala Gly Leu Ala Leu Gln Pro
1               5                   10                  15

Gly Thr Ala Leu Leu Cys Tyr Ser Cys Lys Ala
            20                  25
```

<210> SEQ ID NO 19
<211> LENGTH: 27

<212> TYPE: PRT
<213> ORGANISM: Homo sapiens

<400> SEQUENCE: 19

Lys Ala Gln Val Ser Asn Glu Asp Cys Leu Gln Val Glu Asn Cys Thr
1 5 10 15

Gln Leu Gly Glu Gln Cys Trp Thr Ala Arg Ile
20 25

<210> SEQ ID NO 20
<211> LENGTH: 12
<212> TYPE: PRT
<213> ORGANISM: Homo sapiens

<400> SEQUENCE: 20

Arg Ala Val Gly Leu Leu Thr Val Ile Ser Lys Gly
1 5 10

<210> SEQ ID NO 21
<211> LENGTH: 19
<212> TYPE: PRT
<213> ORGANISM: Homo sapiens

<400> SEQUENCE: 21

Lys Gly Cys Ser Leu Asn Cys Val Asp Asp Ser Gln Asp Tyr Tyr Val
1 5 10 15

Gly Lys Lys

<210> SEQ ID NO 22
<211> LENGTH: 42
<212> TYPE: PRT
<213> ORGANISM: Homo sapiens

<400> SEQUENCE: 22

Lys Asn Ile Thr Cys Cys Asp Thr Asp Leu Cys Asn Ala Ser Gly Ala
1 5 10 15

His Ala Leu Gln Pro Ala Ala Ala Ile Leu Ala Leu Leu Pro Ala Leu
20 25 30

Gly Leu Leu Leu Trp Gly Pro Gly Gln Leu
35 40

<210> SEQ ID NO 23
<211> LENGTH: 11
<212> TYPE: PRT
<213> ORGANISM: Homo sapiens

<400> SEQUENCE: 23

Tyr Ser Cys Lys Ala Gln Val Ser Asn Glu Asp
1 5 10

<210> SEQ ID NO 24
<211> LENGTH: 11
<212> TYPE: PRT
<213> ORGANISM: Homo sapiens

<400> SEQUENCE: 24

Leu Cys Asn Ala Ser Gly Ala His Ala Leu Gln
1 5 10

<210> SEQ ID NO 25
<211> LENGTH: 15
<212> TYPE: PRT
<213> ORGANISM: Homo sapiens

<400> SEQUENCE: 25

Thr Ala Arg Ile Arg Ala Val Gly Leu Leu Thr Val Ile Ser Lys
1 5 10 15

<210> SEQ ID NO 26
<211> LENGTH: 11
<212> TYPE: PRT
<213> ORGANISM: Homo sapiens

<400> SEQUENCE: 26

Leu Cys Asn Ala Ser Gly Ala His Ala Leu Gln
1 5 10

<210> SEQ ID NO 27
<211> LENGTH: 33
<212> TYPE: DNA
<213> ORGANISM: Artificial Sequence
<220> FEATURE:
<223> OTHER INFORMATION: Primer

<400> SEQUENCE: 27
gaattccctg caggtctatg gaacgataaa tgc 33

<210> SEQ ID NO 28
<211> LENGTH: 48
<212> TYPE: DNA
<213> ORGANISM: Artificial Sequence
<220> FEATURE:
<223> OTHER INFORMATION: Primer

<400> SEQUENCE: 28
cccagactcc aacagctgca cctccgccat ggctggttgg gcagcgag 48

<210> SEQ ID NO 29
<211> LENGTH: 36
<212> TYPE: DNA
<213> ORGANISM: Artificial Sequence
<220> FEATURE:
<223> OTHER INFORMATION: Primer

<400> SEQUENCE: 29
atggcggagg tgcagctgtt ggagtctggg ggaggc 36

<210> SEQ ID NO 30
<211> LENGTH: 42
<212> TYPE: DNA
<213> ORGANISM: Artificial Sequence
<220> FEATURE:
<223> OTHER INFORMATION: Primer

<400> SEQUENCE: 30
cgatgggccc ttggtggagg ctgcggagac ggtgaccgtg gt 42

<210> SEQ ID NO 31
<211> LENGTH: 66
<212> TYPE: DNA
<213> ORGANISM: Artificial Sequence
<220> FEATURE:
<223> OTHER INFORMATION: Primer

<400> SEQUENCE: 31
ctcgcggccc aaccggccat ggcgcatcac catcaccatc actcctatga gctgactcag 60
ccaccc 66

<210> SEQ ID NO 32

<211> LENGTH: 48
<212> TYPE: DNA
<213> ORGANISM: Artificial Sequence
<220> FEATURE:
<223> OTHER INFORMATION: Primer

<400> SEQUENCE: 32
gaccgagggg gcagccttgg gctgacttag gacggtcagc ttggtccc 48

<210> SEQ ID NO 33
<211> LENGTH: 33
<212> TYPE: DNA
<213> ORGANISM: Artificial Sequence
<220> FEATURE:
<223> OTHER INFORMATION: Primer

<400> SEQUENCE: 33
cagcccaagg ctgccccctc ggtcactctg ttc 33

<210> SEQ ID NO 34
<211> LENGTH: 36
<212> TYPE: DNA
<213> ORGANISM: Artificial Sequence
<220> FEATURE:
<223> OTHER INFORMATION: Primer

<400> SEQUENCE: 34
ctcgagtcac tatgaacatt ctgtaggggc cactgt 36

<210> SEQ ID NO 35
<211> LENGTH: 42
<212> TYPE: DNA
<213> ORGANISM: Homo sapiens

<400> SEQUENCE: 35
gtgatggtga tggtgatgcg ccatggctgg ttgggcagcg ag 42

<210> SEQ ID NO 36
<211> LENGTH: 42
<212> TYPE: DNA
<213> ORGANISM: Homo sapiens

<400> SEQUENCE: 36
catcaccatc accatcacga ggtgcagctg ttggagtctg gg 42

<210> SEQ ID NO 37
<211> LENGTH: 30
<212> TYPE: DNA
<213> ORGANISM: Homo sapiens

<400> SEQUENCE: 37
gcctccacca agggcccatc ggtcttcccc 30

<210> SEQ ID NO 38
<211> LENGTH: 33
<212> TYPE: DNA
<213> ORGANISM: Homo sapiens

<400> SEQUENCE: 38
cgccatggcc ggttgggccg cgagtaataa caa 33

<210> SEQ ID NO 39
<211> LENGTH: 51
<212> TYPE: DNA
<213> ORGANISM: Homo sapiens -continued

<400> SEQUENCE: 39
gcggcccaac cggccatggc gtcctatgag ctgactcagc caccctcagt g 51

<210> SEQ ID NO 40
<211> LENGTH: 36
<212> TYPE: DNA
<213> ORGANISM: Homo sapiens

<400> SEQUENCE: 40
ctcgagtcac tatgaacatt ctgtaggggc cactgt 36

<210> SEQ ID NO 41
<211> LENGTH: 9
<212> TYPE: PRT
<213> ORGANISM: Homo sapiens

<400> SEQUENCE: 41

Tyr Ser Cys Lys Ala Gln Val Ser Asn
1 5

<210> SEQ ID NO 42
<211> LENGTH: 2392
<212> TYPE: DNA
<213> ORGANISM: Artificial Sequence
<220> FEATURE:
<223> OTHER INFORMATION: Immunoconjugate

<400> SEQUENCE: 42
gaattcctgc aggtctatgg aacgataaat gcccatgaaa attctatttc aaggagacag 60
tcataatgaa atacctattg cctacggcag ccgctggatt gttattactc gctgcccaac 120
cagcgatggc gcaccatcat caccatcacg aggtgcagct gttggagtct gggggaggct 180
tggtacagcc tggggggtcc ctgagactct cctgtgcagc ctcgggattc acctttagaa 240
gctatgccat gagctgggtc cgccaggctc cagggaaggg gctggaatgg gtctcaacta 300
ttagtggtcg tggtgttacc acatactacg cagactccgt gaagggccgg ttcaccatct 360
ccagagacaa ttccaagaac acactgtatt tgcaaatgaa cagcctgaga gccgacgaca 420
cggccctata ttactgtgcg aaagatcgta cccgctacta cggtatggac gtctggggcc 480
aagggaccac ggtcaccgtc tcctcagctt ccaccaaggg cccatcggtc ttcccccctgg 540 caccctcctc caagagcacc tctgggggca cagcggccct gggctgcctg gtcaaggact 600
acttccccga accggtgacg gtgtcgtgga actcaggcgc cctgaccagc ggcgtgcaca 660
ccttcccggc tgtcctacag tcctcaggac tctactccct cagcagcgtg gtgaccgtgc 720
cctccagcag cttgggcacc cagacctaca tctgcaacgt gaatcacaag cccagcaaca 780
ccaaggtgga caagaaagtt gagcccaaat cttgttagtg atctagagtc gacctgcagg 840
tctatggaac gataaatgcc catgaaaatt ctatttcaag gagacagtca taatgaaata 900
cctattgcct acggcagccg ctggattgtt attactcgct gcccaaccag cgatggcgtc 960
ctatgagctg actcagccac cctcagtgtc cgtgtcccca ggacagacag ccagcatcac 1020
ctgctctgga aataaattgg gggataaata tgcttgctgg tatcagcaga agtcaggcca 1080
gtcccctgtg ctggtcatct atcaagattc caagcggccc tcagggatcc ctgagcgatt 1140
ctctggctcc aactctggga acacagccac tctgaccatc agcgggaccc aggctttgga 1200
tgaggctgac tattactgtc aggcgtggga caacagcact gcggtattcg gcggagggac 1260
caagctgacc gtcctaggtc agcccaaggc tgccccctcg gtcactctgt tcccgccctc 1320
ctctgaggag ctccaagcca acaaggccac actagtgtgt ctgatcagtg acttctaccc 1380

-continued

```
gggagctgtg acagtggcct ggaaggcaga tagcagcccc gtcaaggcgg gagtggagac   1440
caccacaccc tccaaacaga gcaacaacaa gtacgcggcc agcagctacc tgagcctgac   1500
gcccgagcag tggaagtccc acagaagcta cagctgccag gtcacgcatg aagggagcac   1560
cgtggagaag acagtggccc ctacagaatg ttcaaccagg cacaggcagc ccagaggctg   1620
ggagcagctc tacaacaccg tgtcatttaa ccttggagaa gcttatgagt accccacttt   1680
tatacaagat ttgcgcaatg aattggctaa gggcacacca gtatgtcaac ttccagtgac   1740
actacaaacc atagccgatg acaagcgatt tgttctagtt gatatcacta cgacctcgaa   1800
gaaaacagtt aaggttgcta tagatgtgac agatgtgtat gttgtgggtt atcaagacaa   1860
atgggatggc aaagatcgag ctgttttcct tgacaaggtt cctactgttg caactagtaa   1920
acttttccca ggggtgacta atcgtgtaac gttaacattt gatggcagct atcagaaact   1980
tgtgaatgct gccaaagctg atagaaaggc tctcgaactg gggggttaaca aattggaatt   2040
ttccattgaa gcaatccatg gtaaaacgat aaatggtcaa gaggcagcca agttctttct   2100
tattgtcatc caaatggttt cagaggcagc tcggttcaaa tatattgaga ctgaggtggt   2160
tgatagagga ttatatggat cattcaaacc taattttaaa gtattgaact tggagaacaa   2220
ttggggcgac atctctgatg ccattcacaa atcatcccca caatgtacca ctattaatcc   2280
ggcacttcag ttgataagcc cctcaaatga cccatgggtt gtaaataaag tgagtcaaat   2340
tagtcccgat atgggtatcc ttaagtttaa aagctccaaa tagtgactcg ag           2392
```

<210> SEQ ID NO 43
<211> LENGTH: 2761
<212> TYPE: DNA
<213> ORGANISM: Artificial Sequence
<220> FEATURE:
<223> OTHER INFORMATION: Immunoconjugate

<400> SEQUENCE: 43

```
gaattcctgc aggtctatgg aacgataaat gcccatgaaa attctatttc aaggagacag     60
tcataatgaa atacctattg cctacggcag ccgctggatt gttattactc gctgcccaac    120
cagcgatggc ggaggtgcag ctgttggagt ctgggggagg cttggtacag cctggggggt    180
ccctgagact ctcctgtgca gcctcgggat tcacctttag aagctatgcc atgagctggg    240
tccgccaggc tccagggaag gggctggaat gggtctcaac tattagtggt cgtggtgtta    300
ccacatacta cgcagactcc gtgaagggcc ggttcaccat ctccagagac aattccaaga    360
acacactgta tttgcaaatg aacagcctga gagccgacga cacggcccta tattactgtg    420
cgaaagatcg tacccgctac tacggtatgg acgtctgggg ccaagggacc acggtcaccg    480
tctcctcagc ttccaccaag ggcccatcgg tcttcccct ggcaccctcc tccaagagca    540
cctctggggg cacagcggcc ctgggctgcc tggtcaagga ctacttcccc gaaccggtga    600
cggtgtcgtg gaactcaggc gccctgacca gcggcgtgca caccttcccg gctgtcctac    660
agtcctcagg actctactcc ctcagcagcg tggtgaccgt gccctccagc agcttgggca    720
cccagaccta catctgcaac gtgaatcaca agcccagcaa caccaaggtg gacaagaaag    780
ttgagcccaa atcttgtgaa tttggtggcg cgccggagtt cccgaaaccg tccaccccgc    840
cgggttcttc tggtcttgag ggcggcagcc tggccgcgct gaccgcgcac caggcctgcc    900
acctgccgct ggagactttc acccgtcatc gccagccgcg cggctgggaa caactggagc    960
agtgcggcta tccggtgcag cggctggtcg ccctctacct ggcggcgcga ctgtcatgga   1020
accaggtcga ccaggtgatc cgcaacgccc tggccagccc cggcagcggc ggcgacctgg   1080
```

-continued

```
gcgaagcgat ccgcgagcag ccggagcagg cacgtctcgc tctgaccctg gccgccgccg   1140

agagcgagcg cttcgtccgg cagggcaccg gcaacgacga ggcaggcgct gcaagcgccg   1200

acgtggtgag cctgacctgc ccggtcgccg ccggtgaatg cgcgggcccg gcggacagcg   1260

gcgacgccct gctggagcgc aactatccca ctggcgcgga gttcctcggc gacggtggcg   1320

acgtcagctt cagcacccgc ggcacgcaga actggacggt ggagcggctg ctccaggcgc   1380

accgccaact ggaggagcgc ggctatgtgt tcgtcggcta ccacggcacc ttcctcgaag   1440

cggcgcaaag catcgtcttc ggcggggtgc gcgcgcgcag ccaggatctc gacgcgatct   1500

ggcgcggttt ctatatcgcc ggcgatccgg cgctggccta cggctacgcc caggaccagg   1560

aacccgacgc gcgcggccgg atccgcaacg gtgccctgct gcgggtctat gtgccgcgct   1620

ccagcctgcc gggcttctac cgcaccggcc tgaccctggc cgcgccggag gcggcgggcg   1680

aggtcgaacg gctgatcggc catccgctgc cgctgcgcct ggacgccatc accggccccg   1740

aggaggaagg cgggcgcctg gagaccattc tcggctggcc gctggccgag cgcaccgtgg   1800

tgattccctc ggcgatcccc accgacccgc gcaacgtcgg tggcgacctc gacccgtcca   1860

gcatccccga caaggaacag gcgatcagcg ccctgccgga ctacgccagc cagcccggca   1920

aaccgccgca tcaccaccat caccataaag acgaactgta gtgactcgac ctgcaggtct   1980

atggaacgat aaatgcccat gaaaattcta tttcaaggag acagtcataa tgaaatacct   2040

attgcctacg gcagccgctg gattgttatt actcgctgcc caaccagcga tggcgcatca   2100

ccatcaccat cactcctatg agctgactca gccaccctca gtgtccgtgt ccccaggaca   2160

gacagccagc atcacctgct ctggaaataa attgggggat aaatatgctt gctggtatca   2220

gcagaagtca ggccagtccc ctgtgctggt catctatcaa gattccaagc ggccctcagg   2280

gatccctgag cgattctctg gctccaactc tgggaacaca gccactctga ccatcagcgg   2340

gacccaggct ttggatgagg ctgactatta ttgtcaggcg tgggacaaca gcactgcggt   2400

attcggcgga gggaccaggc tgaccgtcct aggtcagccc aaggctgccc cctcggtcac   2460

tctgttcccg ccctcctctg aggagctcca agccaacaag gccacactag tgtgtctgat   2520

cagtgacttc tacccgggag ctgtgacagt ggcctggaag gcagatagca gccccgtcaa   2580

ggcgggagtg gagaccacca caccctccaa acagagcaac aacaagtacg cggccagcag   2640

ctacctgagc ctgacgcccg agcagtggaa gtcccacaga agctacagct gccaggtcac   2700

gcatgaaggg agcaccgtgg agaagacagt ggcccctaca gaatgttcat agtgactcga   2760

g                                                                   2761
```

<210> SEQ ID NO 44
<211> LENGTH: 228
<212> TYPE: PRT
<213> ORGANISM: Artificial Sequence
<220> FEATURE:
<223> OTHER INFORMATION: Immunoconjugate

<400> SEQUENCE: 44

```
His His His His His His Glu Val Gln Leu Leu Glu Ser Gly Gly Gly
1               5                   10                  15

Leu Val Gln Pro Gly Gly Ser Leu Arg Leu Ser Cys Ala Ala Ser Gly
            20                  25                  30

Phe Thr Phe Arg Ser Tyr Ala Met Ser Trp Val Arg Gln Ala Pro Gly
        35                  40                  45

Lys Gly Leu Glu Trp Val Ser Thr Ile Ser Gly Arg Gly Val Thr Thr
    50                  55                  60
```

Tyr Tyr Ala Asp Ser Val Lys Gly Arg Phe Thr Ile Ser Arg Asp Asn
65 70 75 80

Ser Lys Asn Thr Leu Tyr Leu Gln Met Asn Ser Leu Arg Ala Asp Asp
85 90 95

Thr Ala Leu Tyr Tyr Cys Ala Lys Asp Arg Thr Arg Tyr Tyr Gly Met
100 105 110

Asp Val Trp Gly Gln Gly Thr Thr Val Thr Val Ser Ser Ala Ser Thr
115 120 125

Lys Gly Pro Ser Val Phe Pro Leu Ala Pro Ser Ser Lys Ser Thr Ser
130 135 140

Gly Gly Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Gln Thr Tyr Ile Cys
195 200 205

Asn Val Asn His Lys Pro Ser Asn Thr Lys Val Asp Lys Lys Val Glu
210 215 220

Pro Lys Ser Cys
225

<210> SEQ ID NO 45
<211> LENGTH: 474
<212> TYPE: PRT
<213> ORGANISM: Artificial Sequence
<220> FEATURE:
<223> OTHER INFORMATION: Immunoconjugate

<400> SEQUENCE: 45

Ser Tyr Glu Leu Thr Gln Pro Pro Ser Val Ser Val Ser Pro Gly Gln
1 5 10 15

Thr Ala Ser Ile Thr Cys Ser Gly Asn Lys Leu Gly Asp Lys Tyr Ala
20 25 30

Cys Trp Tyr Gln Gln Lys Ser Gly Gln Ser Pro Val Leu Val Ile Tyr
35 40 45

Gln Asp Ser Lys Arg Pro Ser Gly Ile Pro Glu Arg Phe Ser Gly Ser
50 55 60

Asn Ser Gly Asn Thr Ala Thr Leu Thr Ile Ser Gly Thr Gln Ala Leu
65 70 75 80

Asp Glu Ala Asp Tyr Tyr Cys Gln Ala Trp Asp Asn Ser Thr Ala Val
85 90 95

Phe Gly Gly Gly Thr Lys Leu Thr Val Leu Gly Gln Pro Lys Ala Ala
100 105 110

Pro Ser Val Thr Leu Phe Pro Pro Ser Ser Glu Glu Leu Gln Ala Asn
115 120 125

Lys Ala Thr Leu Val Cys Leu Ile Ser Asp Phe Tyr Pro Gly Ala Val
130 135 140

Thr Val Ala Trp Lys Ala Asp Ser Ser Pro Val Lys Ala Gly Val Glu
145 150 155 160

Thr Thr Thr Pro Ser Lys Gln Ser Asn Asn Lys Tyr Ala Ala Ser Ser
165 170 175

Tyr Leu Ser Leu Thr Pro Glu Gln Trp Lys Ser His Arg Ser Tyr Ser
180 185 190

```
Cys Gln Val Thr His Glu Gly Ser Thr Val Glu Lys Thr Val Ala Pro
        195                 200                 205

Thr Glu Cys Ser Thr Arg His Arg Gln Pro Arg Gly Trp Glu Gln Leu
    210                 215                 220

Tyr Asn Thr Val Ser Phe Asn Leu Gly Glu Ala Tyr Glu Tyr Pro Thr
225                 230                 235                 240

Phe Ile Gln Asp Leu Arg Asn Glu Leu Ala Lys Gly Thr Pro Val Cys
                245                 250                 255

Gln Leu Pro Val Thr Leu Gln Thr Ile Ala Asp Asp Lys Arg Phe Val
            260                 265                 270

Leu Val Asp Ile Thr Thr Thr Ser Lys Lys Thr Val Lys Val Ala Ile
        275                 280                 285

Asp Val Thr Asp Val Tyr Val Val Gly Tyr Gln Asp Lys Trp Asp Gly
    290                 295                 300

Lys Asp Arg Ala Val Phe Leu Asp Lys Val Pro Thr Val Ala Thr Ser
305                 310                 315                 320

Lys Leu Phe Pro Gly Val Thr Asn Arg Val Thr Leu Thr Phe Asp Gly
                325                 330                 335

Ser Tyr Gln Lys Leu Val Asn Ala Ala Lys Ala Asp Arg Lys Ala Leu
            340                 345                 350

Glu Leu Gly Val Asn Lys Leu Glu Phe Ser Ile Glu Ala Ile His Gly
        355                 360                 365

Lys Thr Ile Asn Gly Gln Glu Ala Ala Lys Phe Phe Leu Ile Val Ile
    370                 375                 380

Gln Met Val Ser Glu Ala Ala Arg Phe Lys Tyr Ile Glu Thr Glu Val
385                 390                 395                 400

Val Asp Arg Gly Leu Tyr Gly Ser Phe Lys Pro Asn Phe Lys Val Leu
                405                 410                 415

Asn Leu Glu Asn Asn Trp Gly Asp Ile Ser Asp Ala Ile His Lys Ser
            420                 425                 430

Ser Pro Gln Cys Thr Thr Ile Asn Pro Ala Leu Gln Leu Ile Ser Pro
        435                 440                 445

Ser Asn Asp Pro Trp Val Val Asn Lys Val Ser Gln Ile Ser Pro Asp
    450                 455                 460

Met Gly Ile Leu Lys Phe Lys Ser Ser Lys
465                 470


<210> SEQ ID NO 46
<211> LENGTH: 609
<212> TYPE: PRT
<213> ORGANISM: Artificial Sequecne
<220> FEATURE:
<223> OTHER INFORMATION: Immunoconjugate

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Thr Ile Ser Gly Arg Gly Val Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Leu Tyr Tyr Cys
```

```
                85                  90                  95

Ala Lys Asp Arg Thr Arg Tyr Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Glu Phe
    210                 215                 220

Gly Gly Ala Pro Glu Phe Pro Lys Pro Ser Thr Pro Pro Gly Ser Ser
225                 230                 235                 240

Gly Leu Glu Gly Gly Ser Leu Ala Ala Leu Thr Ala His Gln Ala Cys
                245                 250                 255

His Leu Pro Leu Glu Thr Phe Thr Arg His Arg Gln Pro Arg Gly Trp
            260                 265                 270

Glu Gln Leu Glu Gln Cys Gly Tyr Pro Val Gln Arg Leu Val Ala Leu
        275                 280                 285

Tyr Leu Ala Ala Arg Leu Ser Trp Asn Gln Val Asp Gln Val Ile Arg
    290                 295                 300

Asn Ala Leu Ala Ser Pro Gly Ser Gly Gly Asp Leu Gly Glu Ala Ile
305                 310                 315                 320

Arg Glu Gln Pro Glu Gln Ala Arg Leu Ala Leu Thr Leu Ala Ala Ala
                325                 330                 335

Glu Ser Glu Arg Phe Val Arg Gln Gly Thr Gly Asn Asp Glu Ala Gly
            340                 345                 350

Ala Ala Ser Ala Asp Val Val Ser Leu Thr Cys Pro Val Ala Ala Gly
        355                 360                 365

Glu Cys Ala Gly Pro Ala Asp Ser Gly Asp Ala Leu Leu Glu Arg Asn
    370                 375                 380

Tyr Pro Thr Gly Ala Glu Phe Leu Gly Asp Gly Gly Asp Val Ser Phe
385                 390                 395                 400

Ser Thr Arg Gly Thr Gln Asn Trp Thr Val Glu Arg Leu Leu Gln Ala
                405                 410                 415

His Arg Gln Leu Glu Glu Arg Gly Tyr Val Phe Val Gly Tyr His Gly
            420                 425                 430

Thr Phe Leu Glu Ala Ala Gln Ser Ile Val Phe Gly Gly Val Arg Ala
        435                 440                 445

Arg Ser Gln Asp Leu Asp Ala Ile Trp Arg Gly Phe Tyr Ile Ala Gly
    450                 455                 460

Asp Pro Ala Leu Ala Tyr Gly Tyr Ala Gln Asp Gln Glu Pro Asp Ala
465                 470                 475                 480

Arg Gly Arg Ile Arg Asn Gly Ala Leu Leu Arg Val Tyr Val Pro Arg
                485                 490                 495

Ser Ser Leu Pro Gly Phe Tyr Arg Thr Gly Leu Thr Leu Ala Ala Pro
            500                 505                 510
```

```
Glu Ala Ala Gly Glu Val Glu Arg Leu Ile Gly His Pro Leu Pro Leu
        515                 520                 525

Arg Leu Asp Ala Ile Thr Gly Pro Glu Glu Glu Gly Gly Arg Leu Glu
    530                 535                 540

Thr Ile Leu Gly Trp Pro Leu Ala Glu Arg Thr Val Val Ile Pro Ser
545                 550                 555                 560

Ala Ile Pro Thr Asp Pro Arg Asn Val Gly Gly Asp Leu Asp Pro Ser
                565                 570                 575

Ser Ile Pro Asp Lys Glu Gln Ala Ile Ser Ala Leu Pro Asp Tyr Ala
            580                 585                 590

Ser Gln Pro Gly Lys Pro Pro His His His His His His Lys Asp Glu
        595                 600                 605

Leu
```

<210> SEQ ID NO 47
<211> LENGTH: 218
<212> TYPE: PRT
<213> ORGANISM: Artificial Sequence
<220> FEATURE:
<223> OTHER INFORMATION: Immunoconjugate

<400> SEQUENCE: 47

```
His His His His His His Ser Tyr Glu Leu Thr Gln Pro Pro Ser Val
1               5                   10                  15

Ser Val Ser Pro Gly Gln Thr Ala Ser Ile Thr Cys Ser Gly Asn Lys
            20                  25                  30

Leu Gly Asp Lys Tyr Ala Cys Trp Tyr Gln Gln Lys Ser Gly Gln Ser
        35                  40                  45

Pro Val Leu Val Ile Tyr Gln Asp Ser Lys Arg Pro Ser Gly Ile Pro
    50                  55                  60

Glu Arg Phe Ser Gly Ser Asn Ser Gly Asn Thr Ala Thr Leu Thr Ile
65                  70                  75                  80

Ser Gly Thr Gln Ala Leu Asp Glu Ala Asp Tyr Tyr Cys Gln Ala Trp
                85                  90                  95

Asp Asn Ser Thr Ala Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

<210> SEQ ID NO 48
<211> LENGTH: 2392
<212> TYPE: DNA
<213> ORGANISM: Artificial Sequence
<220> FEATURE:
<223> OTHER INFORMATION: Immunoconjugate

<400> SEQUENCE: 48

```
gaattcctgc aggtctatgg aacgataaat gcccatgaaa attctatttc aaggagacag     60
tcataatgaa atacctattg cctacggcag ccgctggatt gttattactc gctgcccaac    120
cagcgatggc gcaccatcat caccatcacg aggtgcagct gttggagtct gggggaggct    180
tggtacagcc tggggggtcc ctgagactct cctgtgcagc ctcgggattc acctttagaa    240
gctatgccat gagctgggtc cgccaggctc cagggaaggg gctggaatgg gtctcaacta    300
ttagtggtcg tggtgttacc acatactacg cagactccgt gaagggccgg ttcaccatct    360
ccagagacaa ttccaagaac acactgtatt tgcaaatgaa cagcctgaga gccgacgaca    420
cggccctata ttactgtgcg aaagatcgta cccgctacta cggtatggac gtctggggcc    480
aagggaccac ggtcaccgtc tcctcagctt ccaccaaggg cccatcggtc ttccccctgg    540
caccctcctc caagagcacc tctgggggca cagcggccct gggctgcctg gtcaaggact    600
acttccccga accggtgacg gtgtcgtgga actcaggcgc cctgaccagc ggcgtgcaca    660
ccttcccggc tgtcctacag tcctcaggac tctactccct cagcagcgtg gtgaccgtgc    720
cctccagcag cttgggcacc cagacctaca tctgcaacgt gaatcacaag cccagcaaca    780
ccaaggtgga caagaaagtt gagcccaaat cttgttagtg atctagagtc gacctgcagg    840
tctatggaac gataaatgcc catgaaaatt ctatttcaag gagacagtca taatgaaata    900
cctattgcct acggcagccg ctggattgtt attactcgct gcccaaccag cgatggcgtc    960
ctatgagctg actcagccac cctcagtgtc cgtgtcccca ggacagacag ccagcatcac   1020
ctgctctgga aataaattgg gggataaata tgcttgctgg tatcagcaga agtcaggcca   1080
gtcccctgtg ctggtcatct atcaagattc caagcggccc tcagggatcc ctgagcgatt   1140
ctctggctcc aactctggga acacagccac tctgaccatc agcgggaccc aggctttgga   1200
tgaggctgac tattactgtc aggcgtggga caacagcact gcggtattcg gcggagggac   1260
caagctgacc gtcctaggtc agcccaaggc tgccccctcg gtcactctgt tcccgccctc   1320
ctctgaggag ctccaagcca acaaggccac actagtgtgt ctgatcagtg acttctaccc   1380
gggagctgtg acagtggcct ggaaggcaga tagcagcccc gtcaaggcgg gagtggagac   1440
caccacaccc tccaaacaga gcaacaacaa gtacgcggcc agcagctacc tgagcctgac   1500
gcccgagcag tggaagtccc acagaagcta cagctgccag gtcacgcatg aagggagcac   1560
cgtggagaag acagtggccc ctacagaatg ttcaaccagg cacaggcagc ccagaggctg   1620
ggagcagctc tacaacaccg tgtcatttaa ccttggagaa gcttatgagt accccacttt   1680
tatacaagat ttgcgcaatg aattggctaa gggcacacca gtatgtcaac ttccagtgac   1740
actacaaacc atagccgatg acaagcgatt tgttctagtt gatatcacta cgacctcgaa   1800
gaaaacagtt aaggttgcta tagatgtgac agatgtgtat gttgtgggtt atcaagacaa   1860
atgggatggc aaagatcgag ctgttttcct tgacaaggtt cctactgttg caactagtaa   1920
acttttccca ggggtgacta atcgtgtaac gttaacattt gatggcagct atcagaaact   1980
tgtgaatgct gccaaagctg atagaaaggc tctcgaactg gggggttaaca aattggaatt  2040
ttccattgaa gcaatccatg gtaaaacgat aaatggtcaa gaggcagcca agttctttct   2100
tattgtcatc caaatggttt cagaggcagc tcggttcaaa tatattgaga ctgaggtggt   2160
tgatagagga ttatatggat cattcaaacc taattttaaa gtattgaact tggagaacaa   2220
ttggggcgac atctctgatg ccattcacaa atcatcccca caatgtacca ctattaatcc   2280
ggcacttcag ttgataagcc cctcaaatga cccatgggtt gtaaataaag tgagtcaaat   2340
```

-continued tagtcccgat atgggtatcc ttaagtttaa aagctccaaa tagtgactcg ag 2392

<210> SEQ ID NO 49
<211> LENGTH: 746
<212> TYPE: PRT
<213> ORGANISM: Artificial Sequence
<220> FEATURE:
<223> OTHER INFORMATION: Immunoconjugate

<400> SEQUENCE: 49

Met Lys Tyr Leu Leu Pro Thr Ala Ala Ala Gly Leu Leu Leu Leu Ala
1 5 10 15

Ala Gln Pro Ala Met Ala His His His His His His Glu Val Gln Leu
20 25 30

Leu Glu Ser Gly Gly Gly Leu Val Gln Pro Gly Gly Ser Leu Arg Leu
35 40 45

Ser Cys Ala Ala Ser Gly Phe Thr Phe Arg Ser Tyr Ala Met Ser Trp
50 55 60

Val Arg Gln Ala Pro Gly Lys Gly Leu Glu Trp Val Ser Thr Ile Ser
65 70 75 80

Gly Arg Gly Val Thr Thr Tyr Tyr Ala Asp Ser Val Lys Gly Arg Phe
85 90 95

Thr Ile Ser Arg Asp Asn Ser Lys Asn Thr Leu Tyr Leu Gln Met Asn
100 105 110

Ser Leu Arg Ala Asp Asp Thr Ala Leu Tyr Tyr Cys Ala Lys Asp Arg
115 120 125

Thr Arg Tyr Tyr Gly Met Asp Val Trp Gly Gln Gly Thr Thr Val Thr
130 135 140

Val Ser Ser Ala Ser Thr Lys Gly Pro Ser Val Phe Pro Leu Ala Pro
145 150 155 160

Ser Ser Lys Ser Thr Ser Gly Gly Thr Ala Ala Leu Gly Cys Leu Val
165 170 175

Lys Asp Tyr Phe Pro Glu Pro Val Thr Val Ser Trp Asn Ser Gly Ala
180 185 190

Leu Thr Ser Gly Val His Thr Phe Pro Ala Val Leu Gln Ser Ser Gly
195 200 205

Leu Tyr Ser Leu Ser Ser Val Val Thr Val Pro Ser Ser Ser Leu Gly
210 215 220

Thr Gln Thr Tyr Ile Cys Asn Val Asn His Lys Pro Ser Asn Thr Lys
225 230 235 240

Val Asp Lys Lys Val Glu Pro Lys Ser Cys Met Lys Tyr Leu Leu Pro
245 250 255

Thr Ala Ala Ala Gly Leu Leu Leu Leu Ala Ala Gln Pro Ala Met Ala
260 265 270

Ser Tyr Glu Leu Thr Gln Pro Pro Ser Val Ser Val Ser Pro Gly Gln
275 280 285

Thr Ala Ser Ile Thr Cys Ser Gly Asn Lys Leu Gly Asp Lys Tyr Ala
290 295 300

Cys Trp Tyr Gln Gln Lys Ser Gly Gln Ser Pro Val Leu Val Ile Tyr
305 310 315 320

Gln Asp Ser Lys Arg Pro Ser Gly Ile Pro Glu Arg Phe Ser Gly Ser
325 330 335

Asn Ser Gly Asn Thr Ala Thr Leu Thr Ile Ser Gly Thr Gln Ala Leu
340 345 350

Asp Glu Ala Asp Tyr Tyr Cys Gln Ala Trp Asp Asn Ser Thr Ala Val
355 360 365

-continued

Phe Gly Gly Gly Thr Lys Leu Thr Val Leu Gly Gln Pro Lys Ala Ala
370 375 380

Pro Ser Val Thr Leu Phe Pro Pro Ser Ser Glu Glu Leu Gln Ala Asn
385 390 395 400

Lys Ala Thr Leu Val Cys Leu Ile Ser Asp Phe Tyr Pro Gly Ala Val
405 410 415

Thr Val Ala Trp Lys Ala Asp Ser Ser Pro Val Lys Ala Gly Val Glu
420 425 430

Thr Thr Thr Pro Ser Lys Gln Ser Asn Asn Lys Tyr Ala Ala Ser Ser
435 440 445

Tyr Leu Ser Leu Thr Pro Glu Gln Trp Lys Ser His Arg Ser Tyr Ser
450 455 460

Cys Gln Val Thr His Glu Gly Ser Thr Val Glu Lys Thr Val Ala Pro
465 470 475 480

Thr Glu Cys Ser Thr Arg His Arg Gln Pro Arg Gly Trp Glu Gln Leu
485 490 495

Tyr Asn Thr Val Ser Phe Asn Leu Gly Glu Ala Tyr Glu Tyr Pro Thr
500 505 510

Phe Ile Gln Asp Leu Arg Asn Glu Leu Ala Lys Gly Thr Pro Val Cys
515 520 525

Gln Leu Pro Val Thr Leu Gln Thr Ile Ala Asp Asp Lys Arg Phe Val
530 535 540

Leu Val Asp Ile Thr Thr Thr Ser Lys Lys Thr Val Lys Val Ala Ile
545 550 555 560

Asp Val Thr Asp Val Tyr Val Val Gly Tyr Gln Asp Lys Trp Asp Gly
565 570 575

Lys Asp Arg Ala Val Phe Leu Asp Lys Val Pro Thr Val Ala Thr Ser
580 585 590

Lys Leu Phe Pro Gly Val Thr Asn Arg Val Thr Leu Thr Phe Asp Gly
595 600 605

Ser Tyr Gln Lys Leu Val Asn Ala Ala Lys Ala Asp Arg Lys Ala Leu
610 615 620

Glu Leu Gly Val Asn Lys Leu Glu Phe Ser Ile Glu Ala Ile His Gly
625 630 635 640

Lys Thr Ile Asn Gly Gln Glu Ala Ala Lys Phe Phe Leu Ile Val Ile
645 650 655

Gln Met Val Ser Glu Ala Ala Arg Phe Lys Tyr Ile Glu Thr Glu Val
660 665 670

Val Asp Arg Gly Leu Tyr Gly Ser Phe Lys Pro Asn Phe Lys Val Leu
675 680 685

Asn Leu Glu Asn Asn Trp Gly Asp Ile Ser Asp Ala Ile His Lys Ser
690 695 700

Ser Pro Gln Cys Thr Thr Ile Asn Pro Ala Leu Gln Leu Ile Ser Pro
705 710 715 720

Ser Asn Asp Pro Trp Val Val Asn Lys Val Ser Gln Ile Ser Pro Asp
725 730 735

Met Gly Ile Leu Lys Phe Lys Ser Ser Lys
740 745

<210> SEQ ID NO 50
<211> LENGTH: 2761
<212> TYPE: DNA
<213> ORGANISM: Artificial Sequence
<220> FEATURE:
<223> OTHER INFORMATION: Immunoconjugate

<400> SEQUENCE: 50

```
gaattcctgc aggtctatgg aacgataaat gcccatgaaa attctatttc aaggagacag     60
tcataatgaa atacctattg cctacggcag ccgctggatt gttattactc gctgcccaac    120
cagcgatggc ggaggtgcag ctgttggagt ctgggggagg cttggtacag cctggggggt    180
ccctgagact ctcctgtgca gcctcgggat tcacctttag aagctatgcc atgagctggg    240
tccgccaggc tccagggaag ggctggaat gggtctcaac tattagtggt cgtggtgtta    300
ccacatacta cgcagactcc gtgaagggcc ggttcaccat ctccagagac aattccaaga    360
acacactgta tttgcaaatg aacagcctga gagccgacga cacggcccta tattactgtg    420
cgaaagatcg tacccgctac tacggtatgg acgtctgggg ccaagggacc acggtcaccg    480
tctcctcagc ttccaccaag ggcccatcgg tcttcccccct ggcaccctcc tccaagagca    540
cctctggggg cacagcggcc ctgggctgcc tggtcaagga ctacttcccc gaaccggtga    600
cggtgtcgtg gaactcaggc gccctgacca gcggcgtgca caccttcccg gctgtcctac    660
agtcctcagg actctactcc ctcagcagcg tggtgaccgt gccctccagc agcttgggca    720
cccagaccta catctgcaac gtgaatcaca agcccagcaa caccaaggtg gacaagaaag    780
ttgagcccaa atcttgtgaa tttggtggcg cgccggagtt cccgaaaccg tccaccccgc    840
cgggttcttc tggtcttgag ggcggcagcc tggccgcgct gaccgcgcac caggcctgcc    900
acctgccgct ggagactttc acccgtcatc gccagccgcg cggctgggaa caactggagc    960
agtgcggcta tccggtgcag cggctggtcg ccctctacct ggcggcgcga ctgtcatgga   1020
accaggtcga ccaggtgatc cgcaacgccc tggccagccc cggcagcggc ggcgacctgg   1080
gcgaagcgat ccgcgagcag ccggagcagg cacgtctcgc tctgaccctg gccgccgccg   1140
agagcgagcg cttcgtccgg cagggcaccg gcaacgacga ggcaggcgct gcaagcgccg   1200
acgtggtgag cctgacctgc ccggtcgccg ccggtgaatg cgcgggcccg gcggacagcg   1260
gcgacgccct gctggagcgc aactatccca ctggcgcgga gttcctcggc gacggtggcg   1320
acgtcagctt cagcacccgc ggcacgcaga actggacggt ggagcggctg ctccaggcgc   1380
accgccaact ggaggagcgc ggctatgtgt tcgtcggcta ccacggcacc ttcctcgaag   1440
cggcgcaaag catcgtcttc ggcggggtgc gcgcgcgcag ccaggatctc gacgcgatct   1500
ggcgcggttt ctatatcgcc ggcgatccgg cgctggccta cggctacgcc caggaccagg   1560
aacccgacgc gcgcggccgg atccgcaacg gtgccctgct gcgggtctat gtgccgcgct   1620
ccagcctgcc gggcttctac cgcaccggcc tgaccctggc cgcgccggag gcggcgggcg   1680
aggtcgaacg gctgatcggc catccgctgc cgctgcgcct ggacgccatc accggccccg   1740
aggaggaagg cgggcgcctg gagaccattc tcggctggcc gctggccgag cgcaccgtgg   1800
tgattccctc ggcgatcccc accgacccgc gcaacgtcgg tggcgacctc gacccgtcca   1860
gcatccccga caaggaacag gcgatcagcg ccctgccgga ctacgccagc cagcccggca   1920
aaccgccgca tcaccaccat caccataaag acgaactgta gtgactcgac ctgcaggtct   1980
atggaacgat aaatgcccat gaaaattcta tttcaaggag acagtcataa tgaaatacct   2040
attgcctacg gcagccgctg gattgttatt actcgctgcc caaccagcga tggcgcatca   2100
ccatcaccat cactcctatg agctgactca gccaccctca gtgtccgtgt ccccaggaca   2160
gacagccagc atcacctgct ctggaaataa attgggggat aaatatgctt gctggtatca   2220
gcagaagtca ggccagtccc ctgtgctggt catctatcaa gattccaagc ggccctcagg   2280
gatccctgag cgattctctg gctccaactc tgggaacaca gccactctga ccatcagcgg   2340
```

```
gacccaggct ttggatgagg ctgactatta ttgtcaggcg tgggacaaca gcactgcggt   2400

attcggcgga gggaccaggc tgaccgtcct aggtcagccc aaggctgccc cctcggtcac   2460

tctgttcccg ccctcctctg aggagctcca agccaacaag gccacactag tgtgtctgat   2520

cagtgacttc tacccgggag ctgtgacagt ggcctggaag gcagatagca gccccgtcaa   2580

ggcgggagtg gagaccacca caccctccaa acagagcaac aacaagtacg cggccagcag   2640

ctacctgagc ctgacgcccg agcagtggaa gtcccacaga agctacagct gccaggtcac   2700

gcatgaaggg agcaccgtgg agaagacagt ggcccctaca gaatgttcat agtgactcga   2760

g                                                                    2761
```

<210> SEQ ID NO 51
<211> LENGTH: 871
<212> TYPE: PRT
<213> ORGANISM: Artificial Sequence
<220> FEATURE:
<223> OTHER INFORMATION: Immunoconjugate

<400> SEQUENCE: 51

```
Met Lys Tyr Leu Leu Pro Thr Ala Ala Ala Gly Leu Leu Leu Leu Ala
1               5                   10                  15

Ala Gln Pro Ala Met Ala Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Arg Ser Tyr Ala Met Ser Trp Val Arg Gln Ala Pro Gly
    50                  55                  60

Lys Gly Leu Glu Trp Val Ser Thr Ile Ser Gly Arg Gly Val Thr Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Asp Asp
            100                 105                 110

Thr Ala Leu Tyr Tyr Cys Ala Lys Asp Arg Thr Arg Tyr Tyr Gly Met
        115                 120                 125

Asp Val Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Glu Phe Gly Gly Ala Pro Glu Phe Pro Lys Pro Ser
                245                 250                 255

Thr Pro Pro Gly Ser Ser Gly Leu Glu Gly Gly Ser Leu Ala Ala Leu
            260                 265                 270

Thr Ala His Gln Ala Cys His Leu Pro Leu Glu Thr Phe Thr Arg His
        275                 280                 285
```

```
Arg Gln Pro Arg Gly Trp Glu Gln Leu Glu Gln Cys Gly Tyr Pro Val
    290                 295                 300

Gln Arg Leu Val Ala Leu Tyr Leu Ala Ala Arg Leu Ser Trp Asn Gln
305                 310                 315                 320

Val Asp Gln Val Ile Arg Asn Ala Leu Ala Ser Pro Gly Ser Gly Gly
                325                 330                 335

Asp Leu Gly Glu Ala Ile Arg Glu Gln Pro Glu Gln Ala Arg Leu Ala
            340                 345                 350

Leu Thr Leu Ala Ala Ala Glu Ser Glu Arg Phe Val Arg Gln Gly Thr
        355                 360                 365

Gly Asn Asp Glu Ala Gly Ala Ala Ser Ala Asp Val Val Ser Leu Thr
    370                 375                 380

Cys Pro Val Ala Ala Gly Glu Cys Ala Gly Pro Ala Asp Ser Gly Asp
385                 390                 395                 400

Ala Leu Leu Glu Arg Asn Tyr Pro Thr Gly Ala Glu Phe Leu Gly Asp
                405                 410                 415

Gly Gly Asp Val Ser Phe Ser Thr Arg Gly Thr Gln Asn Trp Thr Val
            420                 425                 430

Glu Arg Leu Leu Gln Ala His Arg Gln Leu Glu Glu Arg Gly Tyr Val
        435                 440                 445

Phe Val Gly Tyr His Gly Thr Phe Leu Glu Ala Ala Gln Ser Ile Val
    450                 455                 460

Phe Gly Gly Val Arg Ala Arg Ser Gln Asp Leu Asp Ala Ile Trp Arg
465                 470                 475                 480

Gly Phe Tyr Ile Ala Gly Asp Pro Ala Leu Ala Tyr Gly Tyr Ala Gln
                485                 490                 495

Asp Gln Glu Pro Asp Ala Arg Gly Arg Ile Arg Asn Gly Ala Leu Leu
            500                 505                 510

Arg Val Tyr Val Pro Arg Ser Ser Leu Pro Gly Phe Tyr Arg Thr Gly
        515                 520                 525

Leu Thr Leu Ala Ala Pro Glu Ala Ala Gly Glu Val Glu Arg Leu Ile
    530                 535                 540

Gly His Pro Leu Pro Leu Arg Leu Asp Ala Ile Thr Gly Pro Glu Glu
545                 550                 555                 560

Glu Gly Gly Arg Leu Glu Thr Ile Leu Gly Trp Pro Leu Ala Glu Arg
                565                 570                 575

Thr Val Val Ile Pro Ser Ala Ile Pro Thr Asp Pro Arg Asn Val Gly
            580                 585                 590

Gly Asp Leu Asp Pro Ser Ser Ile Pro Asp Lys Glu Gln Ala Ile Ser
        595                 600                 605

Ala Leu Pro Asp Tyr Ala Ser Gln Pro Gly Lys Pro Pro His His His
    610                 615                 620

His His His Lys Asp Glu Leu Met Lys Tyr Leu Leu Pro Thr Ala Ala
625                 630                 635                 640

Ala Gly Leu Leu Leu Leu Ala Ala Gln Pro Ala Met Ala His His His
                645                 650                 655

His His His Ser Tyr Glu Leu Thr Gln Pro Pro Ser Val Ser Val Ser
            660                 665                 670

Pro Gly Gln Thr Ala Ser Ile Thr Cys Ser Gly Asn Lys Leu Gly Asp
        675                 680                 685

Lys Tyr Ala Cys Trp Tyr Gln Gln Lys Ser Gly Gln Ser Pro Val Leu
    690                 695                 700

Val Ile Tyr Gln Asp Ser Lys Arg Pro Ser Gly Ile Pro Glu Arg Phe
```

```
705                 710                 715                 720

Ser Gly Ser Asn Ser Gly Asn Thr Ala Thr Leu Thr Ile Ser Gly Thr
                725                 730                 735

Gln Ala Leu Asp Glu Ala Asp Tyr Tyr Cys Gln Ala Trp Asp Asn Ser
            740                 745                 750

Thr Ala Val Phe Gly Gly Gly Thr Lys Leu Thr Val Leu Gly Gln Pro
        755                 760                 765

Lys Ala Ala Pro Ser Val Thr Leu Phe Pro Pro Ser Ser Glu Glu Leu
    770                 775                 780

Gln Ala Asn Lys Ala Thr Leu Val Cys Leu Ile Ser Asp Phe Tyr Pro
785                 790                 795                 800

Gly Ala Val Thr Val Ala Trp Lys Ala Asp Ser Ser Pro Val Lys Ala
                805                 810                 815

Gly Val Glu Thr Thr Thr Pro Ser Lys Gln Ser Asn Asn Lys Tyr Ala
            820                 825                 830

Ala Ser Ser Tyr Leu Ser Leu Thr Pro Glu Gln Trp Lys Ser His Arg
        835                 840                 845

Ser Tyr Ser Cys Gln Val Thr His Glu Gly Ser Thr Val Glu Lys Thr
    850                 855                 860

Val Ala Pro Thr Glu Cys Ser
865                 870


<210> SEQ ID NO 52
<211> LENGTH: 250
<212> TYPE: PRT
<213> ORGANISM: Bougainvillea spectabilis

<400> SEQUENCE: 52

Tyr Asn Thr Val Ser Phe Asn Leu Gly Glu Ala Tyr Glu Tyr Pro Thr
1               5                   10                  15

Phe Ile Gln Asp Leu Arg Asn Glu Leu Ala Lys Gly Thr Pro Val Cys
            20                  25                  30

Gln Leu Pro Val Thr Leu Gln Thr Ile Ala Asp Asp Lys Arg Phe Val
        35                  40                  45

Leu Val Asp Ile Thr Thr Thr Ser Lys Lys Thr Val Lys Val Ala Ile
    50                  55                  60

Asp Val Thr Asp Val Tyr Val Val Gly Tyr Gln Asp Lys Trp Asp Gly
65                  70                  75                  80

Lys Asp Arg Ala Val Phe Leu Asp Lys Val Pro Thr Val Ala Thr Ser
                85                  90                  95

Lys Leu Phe Pro Gly Val Thr Asn Arg Val Thr Leu Thr Phe Asp Gly
            100                 105                 110

Ser Tyr Gln Lys Leu Val Asn Ala Ala Lys Ala Asp Arg Lys Ala Leu
        115                 120                 125

Glu Leu Gly Val Asn Lys Leu Glu Phe Ser Ile Glu Ala Ile His Gly
    130                 135                 140

Lys Thr Ile Asn Gly Gln Glu Ala Ala Lys Phe Phe Leu Ile Val Ile
145                 150                 155                 160

Gln Met Val Ser Glu Ala Ala Arg Phe Lys Tyr Ile Glu Thr Glu Val
                165                 170                 175

Val Asp Arg Gly Leu Tyr Gly Ser Phe Lys Pro Asn Phe Lys Val Leu
            180                 185                 190

Asn Leu Glu Asn Asn Trp Gly Asp Ile Ser Asp Ala Ile His Lys Ser
        195                 200                 205

Ser Pro Gln Cys Thr Thr Ile Asn Pro Ala Leu Gln Leu Ile Ser Pro
```

```
    210                 215                 220

Ser Asn Asp Pro Trp Val Val Asn Lys Val Ser Gln Ile Ser Pro Asp
225                 230                 235                 240

Met Gly Ile Leu Lys Phe Lys Ser Ser Lys
                245                 250


<210> SEQ ID NO 53
<211> LENGTH: 10
<212> TYPE: PRT
<213> ORGANISM: Homo sapiens

<400> SEQUENCE: 53

Met Val Glu Ala Asp Arg Pro Gly Lys Leu
1               5                   10


<210> SEQ ID NO 54
<211> LENGTH: 15
<212> TYPE: PRT
<213> ORGANISM: Homo sapiens

<400> SEQUENCE: 54

Lys Leu Phe Ile Gly Gly Leu Asn Thr Glu Thr Asn Glu Lys Ala
1               5                   10                  15


<210> SEQ ID NO 55
<211> LENGTH: 10
<212> TYPE: PRT
<213> ORGANISM: Homo sapiens

<400> SEQUENCE: 55

Lys Ala Leu Glu Ala Val Phe Gly Lys Tyr
1               5                   10


<210> SEQ ID NO 56
<211> LENGTH: 8
<212> TYPE: PRT
<213> ORGANISM: Homo sapiens

<400> SEQUENCE: 56

Arg Ser Arg Gly Pro Pro Arg Gly
1               5


<210> SEQ ID NO 57
<211> LENGTH: 10
<212> TYPE: PRT
<213> ORGANISM: Homo sapiens

<400> SEQUENCE: 57

Arg Ser Ser Ser Gly Met Gly Gly Arg Ala
1               5                   10


<210> SEQ ID NO 58
<211> LENGTH: 7
<212> TYPE: PRT
<213> ORGANISM: Homo sapiens

<400> SEQUENCE: 58

Arg Ala Pro Val Ser Arg Gly
1               5


<210> SEQ ID NO 59
<211> LENGTH: 12
<212> TYPE: PRT
<213> ORGANISM: Homo sapiens
```

<400> SEQUENCE: 59

Arg Gly Arg Asp Ser Tyr Gly Gly Pro Pro Arg Arg
1 5 10

<210> SEQ ID NO 60
<211> LENGTH: 8
<212> TYPE: PRT
<213> ORGANISM: Homo sapiens

<400> SEQUENCE: 60

Arg Glu Pro Leu Pro Ser Arg Arg
1 5

<210> SEQ ID NO 61
<211> LENGTH: 9
<212> TYPE: PRT
<213> ORGANISM: Homo sapiens

<400> SEQUENCE: 61

Arg Asp Val Tyr Leu Ser Pro Arg Asp
1 5

<210> SEQ ID NO 62
<211> LENGTH: 7
<212> TYPE: PRT
<213> ORGANISM: Homo sapiens

<400> SEQUENCE: 62

Arg Asp Gly Tyr Gly Arg Asp
1 5

<210> SEQ ID NO 63
<211> LENGTH: 14
<212> TYPE: PRT
<213> ORGANISM: Homo sapiens

<400> SEQUENCE: 63

Arg Asp Tyr Ser Asp His Pro Ser Gly Gly Ser Tyr Arg Asp
1 5 10

<210> SEQ ID NO 64
<211> LENGTH: 12
<212> TYPE: PRT
<213> ORGANISM: Homo sapiens

<400> SEQUENCE: 64

Arg Asp Ser Tyr Glu Ser Tyr Gly Asn Ser Arg Ser
1 5 10

<210> SEQ ID NO 65
<211> LENGTH: 8
<212> TYPE: PRT
<213> ORGANISM: Homo sapiens

<400> SEQUENCE: 65

Arg Ser Ala Pro Pro Thr Arg Gly
1 5

<210> SEQ ID NO 66
<211> LENGTH: 10
<212> TYPE: PRT
<213> ORGANISM: Homo sapiens

<400> SEQUENCE: 66

Arg Tyr Asp Asp Tyr Ser Ser Ser Arg Asp

-continued 1 5 10

<210> SEQ ID NO 67
<211> LENGTH: 9
<212> TYPE: PRT
<213> ORGANISM: Homo sapiens

<400> SEQUENCE: 67

Arg Asp Gly Tyr Gly Gly Ser Arg Asp
1 5

<210> SEQ ID NO 68
<211> LENGTH: 9
<212> TYPE: PRT
<213> ORGANISM: Homo sapiens

<400> SEQUENCE: 68

Arg Asp Ser Tyr Ser Ser Ser Arg Ser
1 5

<210> SEQ ID NO 69
<211> LENGTH: 10
<212> TYPE: PRT
<213> ORGANISM: Homo sapiens

<400> SEQUENCE: 69

Arg Ser Asp Leu Tyr Ser Ser Gly Arg Asp
1 5 10

<210> SEQ ID NO 70
<211> LENGTH: 14
<212> TYPE: PRT
<213> ORGANISM: Homo sapiens

<400> SEQUENCE: 70

Arg Asp Gly Tyr Ser Cys Lys Ala Gln Tyr Ser Asn Arg Asp
1 5 10

<210> SEQ ID NO 71
<211> LENGTH: 437
<212> TYPE: PRT
<213> ORGANISM: Homo sapiens

<400> SEQUENCE: 71

Met Val Glu Ala Asp Arg Pro Gly Lys Leu Phe Ile Gly Gly Leu Asn
1 5 10 15

Thr Glu Thr Asn Glu Lys Ala Leu Glu Ala Val Phe Gly Lys Tyr Gly
20 25 30

Arg Ile Val Glu Val Leu Leu Met Lys Asp Arg Glu Thr Asn Lys Ser
35 40 45

Arg Gly Phe Ala Phe Val Thr Phe Glu Ser Pro Ala Asp Ala Lys Asp
50 55 60

Ala Ala Arg Asp Met Asn Gly Lys Ser Leu Asp Gly Lys Ala Ile Lys
65 70 75 80

Val Glu Gln Ala Thr Lys Pro Ser Phe Glu Ser Gly Arg Arg Gly Pro
85 90 95

Pro Pro Pro Pro Arg Ser Arg Gly Pro Pro Arg Gly Leu Arg Gly Gly
100 105 110

Arg Gly Gly Ser Gly Gly Thr Arg Gly Pro Pro Ser Arg Gly Gly His
115 120 125

Met Asp Asp Gly Gly Tyr Ser Met Asn Phe Asn Met Ser Ser Ser Arg
130 135 140

Gly Pro Leu Pro Val Lys Arg Gly Pro Pro Pro Arg Ser Gly Gly Pro
145 150 155 160

Pro Pro Lys Arg Ser Ala Pro Ser Gly Pro Val Arg Ser Ser Ser Gly
165 170 175

Met Gly Gly Arg Ala Pro Val Ser Arg Gly Arg Asp Ser Tyr Gly Gly
180 185 190

Pro Pro Arg Arg Glu Pro Leu Pro Ser Arg Arg Asp Val Tyr Leu Ser
195 200 205

Pro Arg Asp Asp Gly Tyr Ser Cys Lys Ala Gln Tyr Ser Asn Arg Asp
210 215 220

Tyr Pro Ser Ser Arg Asp Thr Arg Asp Tyr Ala Pro Pro Pro Arg Asp
225 230 235 240

Tyr Thr Tyr Arg Asp Tyr Gly His Ser Ser Ser Arg Asp Asp Tyr Pro
245 250 255

Ser Arg Gly Tyr Ser Asp Arg Asp Gly Tyr Gly Arg Asp Arg Asp Tyr
260 265 270

Ser Asp His Pro Ser Gly Gly Ser Tyr Arg Asp Ser Tyr Glu Ser Tyr
275 280 285

Gly Asn Ser Arg Ser Ala Pro Pro Thr Arg Gly Pro Pro Pro Ser Tyr
290 295 300

Gly Gly Ser Ser Arg Tyr Asp Asp Tyr Ser Ser Ser Arg Asp Gly Tyr
305 310 315 320

Gly Gly Ser Arg Asp Ser Tyr Ser Ser Ser Arg Ser Asp Leu Tyr Ser
325 330 335

Ser Gly Arg Asp Arg Val Gly Arg Gln Glu Arg Gly Leu Pro Pro Ser
340 345 350

Met Glu Arg Gly Tyr Leu Leu His Val Ile Pro Thr Ala Val Gln Ala
355 360 365

Ala Asp Ser Gln Glu Val Val Ala Val Glu Glu Ala Asp Leu Ile Glu
370 375 380

Gly Glu Ala Glu Ala Asp Thr Arg Asn Lys Gln Asn Phe Gly Pro Lys
385 390 395 400

Ser Gln Phe Lys Glu Thr Lys Ser Gly Asn Tyr Ser Ile Ile Thr Thr
405 410 415

Gln Gly Leu Leu Lys Gly Lys Ile Val Leu Leu Phe Leu Asn Ser Leu
420 425 430

Leu Ser Ser Pro Pro
435

<210> SEQ ID NO 72
<211> LENGTH: 15
<212> TYPE: PRT
<213> ORGANISM: Homo sapiens

<400> SEQUENCE: 72

Lys Leu Phe Ile Gly Gly Leu Asn Thr Glu Thr Asn Glu Lys Ala
1 5 10 15

<210> SEQ ID NO 73
<211> LENGTH: 10
<212> TYPE: PRT
<213> ORGANISM: Homo sapiens

<400> SEQUENCE: 73

Lys Ala Leu Glu Ala Val Phe Gly Lys Tyr
1 5 10

-continued

<210> SEQ ID NO 74
<211> LENGTH: 10
<212> TYPE: PRT
<213> ORGANISM: Homo sapiens

<400> SEQUENCE: 74

Arg Ile Val Glu Val Leu Leu Met Lys Asp
1               5                   10

<210> SEQ ID NO 75
<211> LENGTH: 16
<212> TYPE: PRT
<213> ORGANISM: Homo sapiens

<400> SEQUENCE: 75

Arg Gly Phe Ala Phe Val Thr Phe Glu Ser Pro Ala Asp Ala Lys Asp
1               5                   10                  15

<210> SEQ ID NO 76
<211> LENGTH: 7
<212> TYPE: PRT
<213> ORGANISM: Homo sapiens

<400> SEQUENCE: 76

Arg Asp Met Asn Gly Lys Ser
1               5

<210> SEQ ID NO 77
<211> LENGTH: 7
<212> TYPE: PRT
<213> ORGANISM: Homo sapiens

<400> SEQUENCE: 77

Lys Ser Leu Asp Gly Lys Ala
1               5

<210> SEQ ID NO 78
<211> LENGTH: 15
<212> TYPE: PRT
<213> ORGANISM: Homo sapiens

<400> SEQUENCE: 78

Lys Val Glu Gln Ala Thr Lys Pro Ser Phe Glu Ser Gly Arg Arg
1               5                   10                  15

<210> SEQ ID NO 79
<211> LENGTH: 9
<212> TYPE: PRT
<213> ORGANISM: Homo sapiens

<400> SEQUENCE: 79

Arg Gly Pro Pro Pro Pro Pro Arg Ser
1               5

<210> SEQ ID NO 80
<211> LENGTH: 9
<212> TYPE: PRT
<213> ORGANISM: Homo sapiens

<400> SEQUENCE: 80

Arg Gly Gly Ser Gly Gly Thr Arg Gly
1               5

<210> SEQ ID NO 81
<211> LENGTH: 7

<212> TYPE: PRT
<213> ORGANISM: Homo sapiens

<400> SEQUENCE: 81

Arg Gly Pro Pro Ser Arg Gly
1 5

<210> SEQ ID NO 82
<211> LENGTH: 21
<212> TYPE: PRT
<213> ORGANISM: Homo sapiens

<400> SEQUENCE: 82

Arg Gly Gly His Met Asp Asp Gly Gly Tyr Ser Met Asn Phe Asn Met
1 5 10 15

Ser Ser Ser Arg Gly
20

<210> SEQ ID NO 83
<211> LENGTH: 8
<212> TYPE: PRT
<213> ORGANISM: Homo sapiens

<400> SEQUENCE: 83

Arg Gly Pro Leu Pro Val Lys Arg
1 5

<210> SEQ ID NO 84
<211> LENGTH: 21
<212> TYPE: PRT
<213> ORGANISM: Homo sapiens

<400> SEQUENCE: 84

Arg Gly Pro Leu Pro Val Lys Arg Gly Pro Pro Pro Arg Ser Gly Gly
1 5 10 15

Pro Pro Pro Lys Arg
20

<210> SEQ ID NO 85
<211> LENGTH: 7
<212> TYPE: PRT
<213> ORGANISM: Homo sapiens

<400> SEQUENCE: 85

Arg Gly Pro Pro Pro Arg Ser
1 5

<210> SEQ ID NO 86
<211> LENGTH: 9
<212> TYPE: PRT
<213> ORGANISM: Homo sapiens

<400> SEQUENCE: 86

Arg Ser Gly Gly Pro Pro Pro Lys Arg
1 5

<210> SEQ ID NO 87
<211> LENGTH: 10
<212> TYPE: PRT
<213> ORGANISM: Homo sapiens

<400> SEQUENCE: 87

Arg Ser Ala Pro Ser Gly Pro Val Arg Ser
1 5 10

<210> SEQ ID NO 88
<211> LENGTH: 10
<212> TYPE: PRT
<213> ORGANISM: Homo sapiens

<400> SEQUENCE: 88

Arg Ser Ser Ser Gly Met Gly Gly Arg Ala
1 5 10

<210> SEQ ID NO 89
<211> LENGTH: 7
<212> TYPE: PRT
<213> ORGANISM: Homo sapiens

<400> SEQUENCE: 89

Arg Ala Pro Val Ser Arg Gly
1 5

<210> SEQ ID NO 90
<211> LENGTH: 12
<212> TYPE: PRT
<213> ORGANISM: Homo sapiens

<400> SEQUENCE: 90

Arg Gly Arg Asp Ser Tyr Gly Gly Pro Pro Arg Arg
1 5 10

<210> SEQ ID NO 91
<211> LENGTH: 10
<212> TYPE: PRT
<213> ORGANISM: Homo sapiens

<400> SEQUENCE: 91

Arg Asp Ser Tyr Gly Gly Pro Pro Arg Arg
1 5 10

<210> SEQ ID NO 92
<211> LENGTH: 8
<212> TYPE: PRT
<213> ORGANISM: Homo sapiens

<400> SEQUENCE: 92

Arg Glu Pro Leu Pro Ser Arg Arg
1 5

<210> SEQ ID NO 93
<211> LENGTH: 9
<212> TYPE: PRT
<213> ORGANISM: Homo sapiens

<400> SEQUENCE: 93

Arg Asp Val Tyr Leu Ser Pro Arg Asp
1 5

<210> SEQ ID NO 94
<211> LENGTH: 8
<212> TYPE: PRT
<213> ORGANISM: Homo sapiens

<400> SEQUENCE: 94

Arg Asp Tyr Pro Ser Ser Arg Asp
1 5

<210> SEQ ID NO 95
<211> LENGTH: 9

<212> TYPE: PRT
<213> ORGANISM: Homo sapiens

<400> SEQUENCE: 95

Arg Asp Tyr Ala Pro Pro Pro Arg Asp
1 5

<210> SEQ ID NO 96
<211> LENGTH: 7
<212> TYPE: PRT
<213> ORGANISM: Homo sapiens

<400> SEQUENCE: 96

Arg Asp Tyr Thr Tyr Arg Asp
1 5

<210> SEQ ID NO 97
<211> LENGTH: 10
<212> TYPE: PRT
<213> ORGANISM: Homo sapiens

<400> SEQUENCE: 97

Arg Asp Tyr Gly His Ser Ser Ser Arg Asp
1 5 10

<210> SEQ ID NO 98
<211> LENGTH: 8
<212> TYPE: PRT
<213> ORGANISM: Homo sapiens

<400> SEQUENCE: 98

Arg Asp Asp Tyr Pro Ser Arg Gly
1 5

<210> SEQ ID NO 99
<211> LENGTH: 7
<212> TYPE: PRT
<213> ORGANISM: Homo sapiens

<400> SEQUENCE: 99

Arg Gly Tyr Ser Asp Arg Asp
1 5

<210> SEQ ID NO 100
<211> LENGTH: 7
<212> TYPE: PRT
<213> ORGANISM: Homo sapiens

<400> SEQUENCE: 100

Arg Asp Gly Tyr Gly Arg Asp
1 5

<210> SEQ ID NO 101
<211> LENGTH: 14
<212> TYPE: PRT
<213> ORGANISM: Homo sapiens

<400> SEQUENCE: 101

Arg Asp Tyr Ser Asp His Pro Ser Gly Gly Ser Tyr Arg Asp
1 5 10

<210> SEQ ID NO 102
<211> LENGTH: 12
<212> TYPE: PRT
<213> ORGANISM: Homo sapiens

<400> SEQUENCE: 102

Arg Asp Ser Tyr Glu Ser Tyr Gly Asn Ser Arg Ser
1               5                   10

<210> SEQ ID NO 103
<211> LENGTH: 8
<212> TYPE: PRT
<213> ORGANISM: Homo sapiens

<400> SEQUENCE: 103

Arg Ser Ala Pro Pro Thr Arg Gly
1               5

<210> SEQ ID NO 104
<211> LENGTH: 10
<212> TYPE: PRT
<213> ORGANISM: Homo sapiens

<400> SEQUENCE: 104

Arg Tyr Asp Asp Tyr Ser Ser Ser Arg Asp
1               5                   10

<210> SEQ ID NO 105
<211> LENGTH: 9
<212> TYPE: PRT
<213> ORGANISM: Homo sapiens

<400> SEQUENCE: 105

Arg Asp Gly Tyr Gly Gly Ser Arg Asp
1               5

<210> SEQ ID NO 106
<211> LENGTH: 9
<212> TYPE: PRT
<213> ORGANISM: Homo sapiens

<400> SEQUENCE: 106

Arg Asp Ser Tyr Ser Ser Ser Arg Ser
1               5

<210> SEQ ID NO 107
<211> LENGTH: 10
<212> TYPE: PRT
<213> ORGANISM: Homo sapiens

<400> SEQUENCE: 107

Arg Ser Asp Leu Tyr Ser Ser Gly Arg Asp
1               5                   10

<210> SEQ ID NO 108
<211> LENGTH: 10
<212> TYPE: PRT
<213> ORGANISM: Homo sapiens

<400> SEQUENCE: 108

Arg Gly Leu Pro Pro Ser Met Glu Arg Gly
1               5                   10

<210> SEQ ID NO 109
<211> LENGTH: 8
<212> TYPE: PRT
<213> ORGANISM: Homo sapiens

<400> SEQUENCE: 109

Arg Gly Tyr Pro Pro Pro Arg Asp 1 5

<210> SEQ ID NO 110
<211> LENGTH: 10
<212> TYPE: PRT
<213> ORGANISM: Homo sapiens

<400> SEQUENCE: 110

Arg Asp Ser Tyr Ser Ser Ser Ser Arg Gly
1 5 10

<210> SEQ ID NO 111
<211> LENGTH: 11
<212> TYPE: PRT
<213> ORGANISM: Homo sapiens

<400> SEQUENCE: 111

Tyr Ser Cys Lys Ala Gln Tyr Ser Asn Arg Asp
1 5 10

<210> SEQ ID NO 112
<211> LENGTH: 11
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: X= Y or V
<220> FEATURE:
<221> NAME/KEY: MISC_FEATURE
<222> LOCATION: (10)..(10)
<223> OTHER INFORMATION: X= R or E

<400> SEQUENCE: 112

Tyr Ser Cys Lys Ala Gln Xaa Ser Asn Xaa Asp
1 5 10

<210> SEQ ID NO 113
<211> LENGTH: 391
<212> TYPE: PRT
<213> ORGANISM: Homo sapiens

<400> SEQUENCE: 113

Met Val Glu Ala Asp Arg Pro Gly Lys Leu Phe Ile Gly Gly Leu Asn
1 5 10 15

Thr Glu Thr Asn Glu Lys Ala Leu Glu Ala Val Phe Gly Lys Tyr Gly
20 25 30

Arg Ile Val Glu Val Leu Leu Met Lys Asp Arg Glu Thr Asn Lys Ser
35 40 45

Arg Gly Phe Ala Phe Val Thr Phe Glu Ser Pro Ala Asp Ala Lys Asp
50 55 60

Ala Ala Arg Asp Met Asn Gly Lys Ser Leu Asp Gly Lys Ala Ile Lys
65 70 75 80

Val Glu Gln Ala Thr Lys Pro Ser Phe Glu Ser Gly Arg Arg Gly Pro
85 90 95

Pro Pro Pro Pro Arg Ser Arg Gly Pro Pro Arg Gly Leu Arg Gly Gly
100 105 110

Arg Gly Gly Ser Gly Gly Thr Arg Gly Pro Pro Ser Arg Gly Gly His
115 120 125

Met Asp Asp Gly Gly Tyr Ser Met Asn Phe Asn Met Ser Ser Ser Arg
130 135 140

Gly Pro Leu Pro Val Lys Arg Gly Pro Pro Pro Arg Ser Gly Gly Pro
145 150 155 160

-continued

```
Pro Pro Lys Arg Ser Ala Pro Ser Gly Pro Val Arg Ser Ser Ser Gly
                165                 170                 175

Met Gly Gly Arg Ala Pro Val Ser Arg Gly Arg Asp Ser Tyr Gly Gly
            180                 185                 190

Pro Pro Arg Arg Glu Pro Leu Pro Ser Arg Arg Asp Val Tyr Leu Ser
        195                 200                 205

Pro Arg Asp Asp Gly Tyr Ser Thr Lys Asp Ser Tyr Ser Ser Arg Asp
    210                 215                 220

Tyr Pro Ser Ser Arg Asp Thr Arg Asp Tyr Ala Pro Pro Pro Arg Asp
225                 230                 235                 240

Tyr Thr Tyr Arg Asp Tyr Gly His Ser Ser Ser Arg Asp Asp Tyr Pro
                245                 250                 255

Ser Arg Gly Tyr Ser Asp Arg Asp Gly Tyr Gly Arg Asp Arg Asp Tyr
            260                 265                 270

Ser Asp His Pro Ser Gly Gly Ser Tyr Arg Asp Ser Tyr Glu Ser Tyr
        275                 280                 285

Gly Asn Ser Arg Ser Ala Pro Pro Thr Arg Gly Pro Pro Pro Ser Tyr
    290                 295                 300

Gly Gly Ser Ser Arg Tyr Asp Asp Tyr Ser Ser Ser Arg Asp Gly Tyr
305                 310                 315                 320

Gly Gly Ser Arg Asp Ser Tyr Ser Ser Ser Arg Ser Asp Leu Tyr Ser
                325                 330                 335

Ser Gly Arg Asp Arg Val Gly Arg Gln Glu Arg Gly Leu Pro Pro Ser
            340                 345                 350

Met Glu Arg Gly Tyr Pro Pro Pro Arg Asp Ser Tyr Ser Ser Ser Ser
        355                 360                 365

Arg Gly Ala Pro Arg Gly Gly Gly Arg Gly Gly Ser Arg Ser Asp Arg
    370                 375                 380

Gly Gly Gly Arg Ser Arg Tyr
385                 390
```